(12) United States Patent
Liu et al.

(10) Patent No.: US 7,795,468 B2
(45) Date of Patent: *Sep. 14, 2010

(54) FUNCTIONALIZED HIGHER DIAMONDOIDS

(75) Inventors: Shenggao Liu, Albany, CA (US); Robert M. Carlson, Petaluma, CA (US); Jeremy E. Dahl, Palo Alto, CA (US); Waqar R. Qureshi, Albany, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 1910 days.

This patent is subject to a terminal disclaimer.

(21) Appl. No.: 10/313,804

(22) Filed: Dec. 6, 2002

(65) Prior Publication Data

US 2003/0199710 A1  Oct. 23, 2003

Related U.S. Application Data

(63) Continuation-in-part of application No. 10/046,486, filed on Jan. 16, 2002, now Pat. No. 6,858,700.

(60) Provisional application No. 60/348,032, filed on Oct. 26, 2001, provisional application No. 60/262,842, filed on Jan. 19, 2001, provisional application No. 60/397,341, filed on Jul. 18, 2002, provisional application No. 60/336,722, filed on Dec. 7, 2001.

(51) Int. Cl.
| | |
|---|---|
| C07C 61/12 | (2006.01) |
| C07C 61/28 | (2006.01) |
| C07D 221/22 | (2006.01) |
| C07C 275/26 | (2006.01) |
| C07C 235/26 | (2006.01) |
| C07C 211/16 | (2006.01) |

(52) U.S. Cl. ............... 562/498; 546/26; 564/188; 564/452; 564/57; 568/669

(58) Field of Classification Search ............ 562/498; 546/26; 564/188, 452, 57; 568/669
See application file for complete search history.

(56) References Cited

U.S. PATENT DOCUMENTS

| | | | |
|---|---|---|---|
| 3,457,318 A | 7/1969 | Capaldi | |
| 3,832,332 A | 8/1974 | Thompson | |
| 4,001,223 A | 1/1977 | Sugimoto et al. | |
| 4,016,271 A | 4/1977 | Phillipps et al. | |
| 4,061,774 A | 12/1977 | Chakrabarti et al. | |
| 4,100,170 A | 7/1978 | Shetty | |
| 4,142,036 A | 2/1979 | Feinstein | |
| 4,273,704 A | 6/1981 | Mazur | |
| 4,288,609 A | 9/1981 | Rovati et al. | |
| 4,473,575 A | 9/1984 | Watthey | |
| 4,692,515 A | 9/1987 | Georgiev et al. | |
| 4,952,747 A | 8/1990 | Alexander et al. | |
| 4,952,748 A | 8/1990 | Alexander | |
| 4,952,749 A | 8/1990 | Alexander | |
| 4,952,757 A | 8/1990 | Purcell | |
| 4,982,049 A | 1/1991 | Alexander | |
| 5,015,758 A | 5/1991 | Pilgrim et al. | |
| 5,017,734 A | 5/1991 | Baum | |
| 5,019,660 A * | 5/1991 | Chapman et al. | ............... 585/22 |
| 5,019,665 A | 5/1991 | Partridge | |
| 5,053,434 A * | 10/1991 | Chapman | ............... 521/52 |
| 5,061,703 A | 10/1991 | Bormann et al. | |
| 5,238,705 A | 8/1993 | Hayashi et al. | |
| 5,245,104 A | 9/1993 | Cullick | |
| 5,256,391 A | 10/1993 | Chen et al. | |
| 5,268,513 A | 12/1993 | Shen | |
| 5,298,666 A | 3/1994 | Shen | |
| 5,306,851 A | 4/1994 | Wu | |
| 5,308,661 A | 5/1994 | Feng et al. | |
| 5,347,063 A | 9/1994 | Shen | |
| 5,367,051 A | 11/1994 | Narang et al. | |
| 5,369,213 A * | 11/1994 | Shen | ............... 585/352 |
| 5,380,947 A | 1/1995 | Chen | |
| 5,382,684 A | 1/1995 | Moini | |

(Continued)

FOREIGN PATENT DOCUMENTS

EP   0399851 B1   11/1996

(Continued)

OTHER PUBLICATIONS

Moiseev et al., Reactions of Adamantanes on Electrophilic Media, Russian Chemical Review, 68 (12), 1999, 1001-1020.*

(Continued)

*Primary Examiner*—Brian J. Davis
(74) *Attorney, Agent, or Firm*—Merchant & Gould

(57) ABSTRACT

This invention is directed to functionalized higher diamondoids having at least one functional group. Preferably these derivatives have the following Formula I:

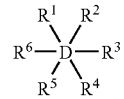

wherein D is a higher diamondoid nucleus and wherein $R^1$, $R^2$, $R^3$, $R^4$, $R^5$ and $R^6$ are independently selected from a group consisting of hydrogen and functional groups, provided that there is at least one functional group on the derivative. The functionalized higher diamondoid compounds may also be of the formula $D$—$L$—$(D)_n$ wherein D is a higher diamondoid nucleus and L is a linking group and n is 1 or more. The functionalized higher diamondoid compounds additionally may be of the formula $R^{38}$—$D$—$D$—$R^{39}$ wherein D is a higher diamondoid nucleus and $R^{38}$ and $R^{39}$ are substituents.

32 Claims, 19 Drawing Sheets

U.S. PATENT DOCUMENTS

| | | | |
|---|---|---|---|
| 5,397,488 | A | 3/1995 | Chen |
| 5,410,092 | A | 4/1995 | Shen |
| 5,414,189 | A * | 5/1995 | Chen et al. .................. 585/801 |
| 5,416,188 | A | 5/1995 | Chiang et al. |
| 5,430,193 | A | 7/1995 | Shen |
| 5,449,531 | A | 9/1995 | Zhu et al. |
| 5,455,072 | A | 10/1995 | Bension et al. |
| 5,461,184 | A | 10/1995 | Swanson |
| 5,462,680 | A | 10/1995 | Brois et al. |
| 5,462,776 | A | 10/1995 | Gruen |
| 5,498,812 | A | 3/1996 | Bradway |
| 5,576,355 | A | 11/1996 | Chen |
| 5,595,995 | A | 1/1997 | Chan et al. |
| 5,635,581 | A | 6/1997 | Chiang et al. |
| 5,695,847 | A | 12/1997 | Browne |
| 5,739,376 | A | 4/1998 | Bingel |
| 5,849,130 | A | 12/1998 | Browne |
| 5,861,135 | A | 1/1999 | Tanabe et al. |
| 5,874,175 | A | 2/1999 | Li |
| 5,880,154 | A | 3/1999 | Boukrinskaia |
| 6,057,364 | A | 5/2000 | Jasys et al. |
| 6,066,652 | A | 5/2000 | Zenner et al. |
| 6,080,470 | A | 6/2000 | Dorfman |
| 6,162,412 | A | 12/2000 | Fujimori |
| 6,187,427 | B1 | 2/2001 | Taylor-Smith |
| 6,201,024 | B1 | 3/2001 | Baxter et al. |
| 6,235,851 | B1 | 5/2001 | Ishii |
| 6,277,766 | B1 | 8/2001 | Ayers |
| 6,300,410 | B1 | 10/2001 | Shachat et al. |
| 6,319,935 | B1 | 11/2001 | Munk et al. |
| 6,344,590 | B1 | 2/2002 | Nakano et al. |
| 6,743,290 | B2 | 6/2004 | Dahl et al. |
| 6,812,370 | B2 * | 11/2004 | Dahl et al. .................. 585/352 |
| 6,812,371 | B2 | 11/2004 | Dahl et al. |
| 6,815,569 | B1 * | 11/2004 | Dahl et al. .................. 585/352 |
| 6,828,469 | B2 | 12/2004 | Dahl et al. |
| 6,831,202 | B2 * | 12/2004 | Dahl et al. .................. 585/352 |
| 6,843,851 | B2 * | 1/2005 | Dahl et al. .................... 117/68 |
| 6,844,477 | B2 | 1/2005 | Carlson et al. |
| 6,858,700 | B2 | 2/2005 | Dahl et al. |
| 6,861,569 | B2 | 3/2005 | Dahl et al. |
| 7,034,194 | B2 * | 4/2006 | Dahl et al. .................. 585/352 |
| 7,049,374 | B2 * | 5/2006 | Liu et al. .................... 525/437 |
| 2002/0137976 | A1 | 9/2002 | Dahl et al. |
| 2003/0097032 | A1 | 5/2003 | Dahl et al. |

FOREIGN PATENT DOCUMENTS

| | | | |
|---|---|---|---|
| WO | WO 92/13909 | * | 8/1992 |
| WO | WO 92/13909 | A1 | 8/1992 |
| WO | WO 95/11472 | A1 | 4/1995 |
| WO | WO02/057201 | A2 | 7/2002 |

OTHER PUBLICATIONS

McKervey et al., Synthetic Approaches to Large Diamondoid Hydrocarbons, Tetrahedron, 36, 1980, 971-992.*

Courtney et al., The Chemistry of Diamantane, Part 1. Synthesis and Some Functionalisation Reactions, J.C.S. Perkin I, 1972, 2691-2696.*

Aczel, et al., "Stability of Adamantane and its Derivatives to Coal-liquefaction Conditions, and its implications toward the organic structure of Coal", *Fuel*, vol. 58, pp. 228-230, (Mar. 1979).

Bagrii, Ye, et al., "Catalytic Breakdown of Paraffinic Hydrocarbons in the Presence of Adamantanes", *Petrol. Chem USSR*, vol. 30, No. 2, pp. 131-134, (1990).

Bagrii, et al., "Activiation of C—H Bonds and Functionalization of Hydrocarbons of the Adamantane Series", *Neftekhimiya*, 33(3), pp. 195-212 (1993).

Balaban, et al., Systemic Classification and Nomenclature of Diamond Hydrocarbons-I, *Tetrahedron*, 34, pp. 3599-3606 (1978).

Baughman, GL, "Dibromination of Adamantane", Publication Unknown, vol. 29, pp. 238-240 (Jan. 1964).

Bingham, RC, et al., "Recent Developments in the Chemistry of Adamantane and Related Polycyclic Hydrocarbons", *Chemistry of Adamantanes*, Ch. 18, pp. 1-101 (1970).

Bott, Von K., "Synthese von Adamantan-und Norbornan chloressigsauren mit Trichlorathylen", *Angew. Chem.*, vol. 79, pp. 943-945 (1967).

Bott, Von K., "Carbonsauresynthesen mit 1,1-Dichlorathylen", *Agnew. Chem.*, 78. Jahrg. ,pp. 932-936 (1966).

Cammas, S., et al., "Poly(β-malic acid): Obtaining High Molecular Weights by Improvement of the Synthesis Route", *Polymer*, vol. 37, No. 18, pp. 4215-4220 (1996).

Chung, et al., Recent Development in High-Energy Density Liquid Fuels, *Energy and Fuels*, 13, pp. 641-649, (1999).

Courtney, T., et al., "The Chemistry of Diamantane: Part I—Synthesis and Some Functionalisation Reactions", J.C.S.Perkin I, pp. 2691-2696 (1972).

Dahl, J., et al., Diamondoid Hydrocarbons as Indicators of Natural Oil Cracking, *Nature*, 399, pp. 54-57 (1999).

Drexler, Eric K., *Nanosystems: Molecular Machinery Manufacturing and Computation*, John Wiley & Sons, pp. 238-249 (1992).

Fort, Jr., et al., Adamantane: Consequences of the Diamondoid Structure, *Chem. Rev.*, 64, pp. 277-300 (1964).

Haaf, W., "Untersuchungen uber die Ritter-Reacktion", pp. 3359-3369 (1963).

Hala, V.S., et al., "Analyse Unds erwendung on Pyrolyseol", *Jahrgang*, pp. 85-87, (Feb. 1971) In German- English Abstract on p. 85.

Koch, H., "Direkte Syntese der Adamantan-carbonsaure-(1)", *Eingengangen Am.*, 29, p. Z 944 (1960).

Landa, S., "Adamantane and Its Homologues", *Current Science*, vol. 52, No. 11, pp. 485-489 (1963).

Liaw, Der-Jang, et al., "Synthesis and Characterization of new Polyamides and Polyimides Prepared from 2,2-bix[4-(4-aminophenoxy)phenyl]adamantane", *Macromol. Chem. Phys.*, 200, No. 6, pp. 1326-1332 (1999).

Lin, et al., Natrual Occurrence of Tetramantane ($C_{22}H_{36}$), Pentamantane ($C_{26}H_{32}$), and Hexamantane ($C_{30}H_{36}$) in a Deep Petroleum Reservoir, *Fuel*, 74:10, pp. 1512-1521 (1995).

Lippert, E., et al., "Darstellung und UV-Spektren eininger Fluorenon-Derivate", *Agnew. Chem.*, vol. 71, No. 13, pp. 429-430 (1959).

McKervey, "Synthetic Approaches to Large Diamondoid Hydrocarbonds", *Tetrahedron*, 36, pp. 971-992 (1980).

Machacek, V., et al., "Let Od Objeveni Adamantanu", *Chemicke Listy/svazek*, pp. 753-761, (1982) Russian—English Abstract on p. 761.

Moine, L., et al., "Polymers of Malic Acid Conjugated with the 1-adamantyl Moiety as Lipophilic Pendant Group", *Polymer*, vol. 38, No. 12, pp. 3121-3127 (1997).

Moiseev, IK, et al., "Reactions of Adamantanes in Electrophilic Media", *Russian Chem. Reviews*, vol. 68, No. 12, pp. 1001-1120 (1999).

Neavel, R., "Liquefaction of Coal in Hydrogen-Donor and Non-Donor Vehicles", *Fuel*, vol. 55, pp. 237-242 (1976).

Oya, A, et al., "Carbonization of Adamantanes to a Graphitizable Carbon", *Fuel*, vol. 60, pp. 667-669 (Aug. 1981).

Petrov, A., "Hydrocarbons of Adamantane Series as Indicies of Petroleum Catagenesis Process", *Advances in Organic Geo Chemistry*, 6th International Meeting on Organic Geochemistry, pp. 517-522 (1973).

Prusova, D., Liquid Chromatography of Adamantanes and Carbon Adsorbents, *J. Chrom*, 234, pp. 1-11 (1982).

Rollman, L., et al., "Adamantanes From Petroleum, with Zeolites", American Chemical Study, 210th ACS National Meeting, Abstract and paper, Aug. 20, 1995).

Sandia National Laboratories (2000), World's First Diamond Micromachines Created at Sandia, Press Release, (Feb. 22, 2000), www.Sandia.gov.

Schleyer, P., et al., "Nonacyclo[$11.7.1.1^{2,18}.0^{4,13}.0^{4,13}.0^{5,10}.0^{6,14}.0^{7,11}.0^{15,20}$]-Docosane, a Bastard Tetramantane", *J. of the Am. Chem. Soc.*, 90:8, letter to the editor, Aug. 28, 1968.

Schleyer, P., et al., "The Preparation and Reactivity of 2-Substituted Derivatives", *Frick Chemical Laboratory*, vol. 83, pp. 182-187 (1961).

Shen, M., et al., Finite $T_d$ Symmetry Models for Diamond: From Adamantane to Superadamantane ($C_{35}H_{36}$), *J. Am., Chem. Soc.*, vol. 114, No. 2, pp. 497-505 (1992).

Smith, G., et al., "Some Reactions of Adamantane and Adamantane Derivatives", *publication unknown*, vol. 26, pp. 2207-2212 (1961).

Stetter, et al., "Zur Kenntnis der Adamantan-carbonsaure-(1)", *Uber Verbidugen mit Urotropin-Struktur*, XVII, pp. 1161-1166 (1960).

Stetter, H., et al., "Monofunktionelle Adamantan-Derivate", *Angew. Chem.*, 71, pp. 429-430 (1959).

Stetter, H., et al., "Beitrage zur Chemie der Adamantyl-(1)-Derivate", *Publication Unknown*, pp. 226-230 (1959).

Supryadkina, NY, et al., "Catalytic Dealkylation of Alkyladamantanes", *Petrol. Chem., USSR*, vol. 28, No. 2, pp. 103-110 (1988).

Tominaga, K., et al., "Next-generation Fine Chemicals Raw Material-Adamantane", *Chem Econ & Eng. Review*, Vol. 17, No. 10, pp. 23-29 (Oct. 1985).

Vodicka, L, et al., "High Performance Liquid Chromatography of Halogeno Derivatives of Adamantane and Diamantane", *J. Chrom*, 270, pp. 199-205 (1983).

Wingert, W., "G.c.-m.s. Analysis of Diamondoid Hydrocarbons in Smackover Petroleums", *Fuel*, vol. 71, pp. 37-42 (Jan. 1992).

Broich, F., "Carbonsauresynthesen mit 1,1-Dichlorathylen", *Angew. chem.*, vol. 78, pp. 932-936 (1966) (English and German).

Chakrabarti et al., "Chemistry of Adamantane. Part II. Synthesis of 1-Adamantyloxyalkylamines", *Tetrahedron Letters* 60:6249-6252 (1968).

Gerzon, et al., "The Adamantyl Group in Medicinal Agents, 1. Hypoglycemic N-Arylsulfonyl-N-adamantylureas", *Journal of Medicinal Chemistry* 6(6):760-763 (1963).

Hass, et al., Adamantyoxycarbonyl, a New Blocking Group. Preparation of 1-Adamantyl Chloroformate, *Journal of the American Chemical Society* 88(9):1988-1992 (1966).

Lansbury, et al., "Some Reactions of α-Metalated Ethers", *The Journal of Organic Chemistry* 27(6):1933-1939 (1962).

Makarova, et al., "Psychotropic Activity of Some Aminoketones Belonging to the Adamantane Group" *Pharmaceutical Chemistry Journal* 34:6 (2000).

Marshall et al., "Further studies on N-Arylsulfonyl-N-alkylureas", *Journal of Medicinal Chemistry* 6:60-63 (1963).

Marshall et al., "N-Arylsulfonyl-N-alkylureas", *Journal of Organic Chemistry* 23:927-929 (1958).

Nordlander et al., "Solvolysis of 1-Adamantylcarbinyl and 3-Homoadamantyl Derivatives. Mechanism of the Neopentyl Cation Rearrangement", *Journal of the American Chemical Society* 88:19 (1966).

Reinhardt, "Biadamantane and some if its Derivatives", *Journal of Organic Chemistry* 27:3258-3261 (1962).

Sasaki et al., "Synthesis of Adamantane Derivatives. II. Preparation of Some Derivatives from Adamantylacetic Acid", *Bulletin of the Chemical Society of Japan* 41(1):238-240 (1968).

Sasaki et al., "Substitution Reaction of 1-Bromoadamantane in Dimethyl Sulfoxide: Simple Synthesis of 1-Azidoadamantane", *Journal of the American Chemical Society* 92:24 (1970).

Stetter, et al., "Ein Beitrag zur Frage der Reaktivitat von Bruckenkopf-Carboniumionen", *Uber Verbindungen mit Urotropin-Struktur XXVI, Chem. Ber.* 96:550-555 (1963).

Stetter, et al., "Neue Moglichkeiten der Direcktsubstitution am Adamantan", *Uber Verbindugen mit Urotropin-Struktur, XLII, Chem. Ber.* 102(10):3357-3363 (1969).

Stetter et al., "Uber Adamantan-phosphonsaure-(1)-dichlorid", *Uber Verbindungen mit Urotropin-Strukture XLIV, Chem. Ber.* 102(10):3364-3366 (1969).

Stetter, et al., "Herstellung von Derivaten des 1-Phenyl-adamantans", *Uber Verbindungen mit Urotropin-Strukture, XXXI, Chem. Ber.* 97(12):3488-3492 (1964).

von H.U. Daeniker, "206. 1-Hydrazinoadamantan", *Helvetica Chimica Acta* 50:2008-2010 (1967).

Stetter, Herman, and Claus Wulff, "Derivate des 1-Aminoadamantans", Über Verbindungen mit Urotropin-Struktur (XXIV), *Liebigs Ann. Chem.* Jahrg. 95:2302-2304 (1962).

McKervey, M. Anthony and John J. Rooney, "Chapter II. Catalytic Routes to Adamantane and Its Homologues", *Cage Hydrocarbons*, George A. Olah, ed., John Wiley & Sons, Inc., New York, 1990, pp. 39-64.

Geluk, H.W., and V.G. Keizer, "Adamantanone", *Organic Syntheses* 53:8-12 (1973).

* cited by examiner

Fig. 4A

| Higher Diamondoid | Compound Reference Number | M+ (m/z) (Equals Base Peak) | GC/MS Retention Times* (min.) | GC/MS Relative Retention Times** (min.) |
|---|---|---|---|---|
| Tetramantane #1 | 4-1 | 292 | 8.10 | 1.00 |
| Tetramantane #2 | 4-2 | 292 | 8.66 | 1.07 |
| Tetramantane #3 | 4-3 | 292 | 9.12 | 1.13 |
| Pentamantane #1 | 5-1 | 344 | 10.40 | 1.28 |
| Pentamantane #2 | 5-2 | 344 | 11.93 | 1.47 |
| Pentamantane #3 | 5-3 | 344 | 11.98 | 1.48 |
| Pentamantane #4 | 5-4 | 344 | 12.38 | 1.53 |
| Pentamantane #5 | 5-5 | 344 | 12.50 | 1.54 |
| Pentamantane #6 | 5-6 | 344 | 12.71 | 1.57 |
| Cyclohexamantane | C-6 | 342 | 12.34 | 1.52 |
| Hexamantane #1 | 6-1 | 396 | 14.46 | 1.78 |
| Hexamantane #2 | 6-2 | 396 | 14.61 | 1.80 |
| Hexamantane #3 | 6-3 | 396 | 14.97 | 1.85 |
| Hexamantane #4 | 6-4 | 396 | 14.99 | 1.85 |
| Hexamantane #5 | 6-5 | 396 | 15.04 | 1.86 |
| Hexamantane #6 | 6-6 | 396 | 15.13 | 1.87 |
| Hexamantane #7 | 6-7 | 396 | 15.22 | 1.88 |
| Hexamantane #8 | 6-8 | 396 | 15.32 | 1.89 |
| Hexamantane #9 | 6-9 | 396 | 15.42 | 1.90 |
| Hexamantane #10 | 6-10 | 396 | 15.45 | 1.91 |
| Hexamantane #11 | 6-11 | 396 | 15.49 | 1.91 |
| Hexamantane #12 | 6-12 | 396 | 15.54 | 1.92 |
| Hexamantane #13 | 6-13 | 396 | 15.60 | 1.93 |
| Hexamantane #14 | 6-14 | 396 | 15.81 | 1.95 |
| Hexamantane #15 | 6-15 | 396 | 15.89 | 1.96 |
| Hexamantane #16 | 6-16 | 396 | 16.05 | 1.98 |
| Hexamantane #17 | 6-17 | 396 | 16.08 | 1.99 |
| Heptamantane #1 | 7-1 | 394 | 14.96 | 1.85 |
| Heptamantane #2 | 7-2 | 394 | 15.53 | 1.92 |
| Heptamantane #3 | 7-3 | 448 | 17.34 | 2.14 |
| Heptamantane #4A | 7-4A | 448 | 17.70 | 2.18 |
| Heptamantane #4B | 7-4B | 448 | 17.70 | 2.18 |
| Heptamantane #5 | 7-5 | 448 | 17.71 | 2.19 |
| Heptamantane #6 | 7-6 | 448 | 17.79 | 2.20 |
| Heptamantane #7 | 7-7 | 448 | 17.82 | 2.20 |
| Heptamantane #8 | 7-8 | 448 | 17.99 | 2.22 |
| Heptamantane #9A | 7-9A | 448 | 18.13 | 2.24 |
| Heptamantane #9B | 7-9B | 448 | 18.13 | 2.24 |
| Heptamantane #9C | 7-9C | 448 | 18.13 | 2.24 |
| Heptamantane #10 | 7-10 | 448 | 18.15 | 2.24 |
| Heptamantane #11 | 7-11 | 448 | 18.20 | 2.25 |
| Heptamantane #12 | 7-12 | 448 | 18.21 | 2.25 |
| Heptamantane #13A | 7-13A | 448 | 18.29 | 2.26 |
| Heptamantane #13B | 7-13B | 448 | 18.29 | 2.26 |
| Heptamantane #13C | 7-13C | 448 | 18.29 | 2.26 |
| Heptamantane #14 | 7-14 | 448 | 18.32 | 2.26 |

Fig. 4A cont'd

| Higher Diamondoid | Compound Reference Number | M+ (m/z) (Equals Base Peak) | GC/MS Retention Times* (min.) | GC/MS Relative Retention Times** (min.) |
|---|---|---|---|---|
| Octamantane #1 | 8-1 | 446 | 17.30 | 2.14 |
| Octamantane #2 | 8-2 | 446 | 17.37 | 2.14 |
| Octamantane #3 | 8-3 | 446 | 17.42 | 2.15 |
| Octamantane #4 | 8-4 | 446 | 17.47 | 2.16 |
| Octamantane #5 | 8-5 | 446 | 17.71 | 2.19 |
| Octamantane #6 | 8-6 | 446 | 17.82 | 2.20 |
| Octamantane #7 | 8-7 | 446 | 17.86 | 2.20 |
| Octamantane #8 | 8-8 | 446 | 18.22 | 2.25 |
| Octamantane #9 | 8-9 | 446 | 18.46 | 2.28 |
| Octamantane #10 | 8-10 | 446 | 18.65 | 2.30 |
| Octamantane #11 | 8-11 | 446 | 18.76 | 2.32 |
| Nonamantane #1 | 9-1 | 498 | 19.86 | 2.45 |
| Decamantane #1 | 10-1 | 456 | 18.57 | 2.29 |
| Decamantane #2 | 10-2 | 496 | 21.33 | 2.63 |
| Undecamantane #1 | 11-1 | 508 | 21.05 | 2.60 |

* HP-MS5 (30m X 0.25 mm, 0.25 micron film), helium carrier gas,
** Reference to Tetramantane #1

Fig. 4B

| Higher Diamondoid | Compound Reference Number | Fraction Number | Elution Time (min.) | Elution Volume (mL) | Elution Volume Relative to 4-1 |
|---|---|---|---|---|---|
| Tetramantane #1 | 4-1 | 4 | 119 | 594 | 1.00 |
| Tetramantane #2 | 4-2 | 7 | 125 | 627 | 1.05 |
| Tetramantane #3 | 4-3 | 6 | 123 | 616 | 1.04 |
| Pentamantane #1 | 5-1 | 11 | 134 | 669 | 1.13 |
| Pentamantane #2 | 5-2 | 19 | 151 | 754 | 1.27 |
| Pentamantane #3 | 5-3 | 28 | 170 | 850 | 1.43 |
| Pentamantane #4 | 5-4 | 22 | 157 | 786 | 1.32 |
| Pentamantane #5 | 5-5 | 19 | 151 | 754 | 1.27 |
| Pentamantane #6 | 5-6 | 20 | 153 | 765 | 1.29 |
| Cyclohexamantane | C-6 | 23 | 159 | 797 | 1.34 |
| Hexamantane #1 | 6-1 | 33 | 181 | 903 | 1.52 |
| Hexamantane #2 | 6-2 | 29 | 172 | 861 | 1.45 |
| Hexamantane #3 | 6-3 | 43 | 202 | 1012 | 1.70 |
| Hexamantane #4 | 6-4 | 33 | 181 | 903 | 1.52 |
| Hexamantane #5 | 6-5 | 35 | 185 | 924 | 1.56 |
| Hexamantane #6 | 6-6 | 63 | 242 | 1211 | 2.04 |
| Hexamantane #7 | 6-7 | 37 | 189 | 945 | 1.59 |
| Hexamantane #8 | 6-8 | 39 | 193 | 967 | 1.63 |
| Hexamantane #9 | 6-9 | 39 | 193 | 967 | 1.63 |
| Hexamantane #10 | 6-10 | 48 | 214 | 1071 | 1.80 |
| Hexamantane #11 | 6-11 | 36 | 187 | 935 | 1.57 |
| Hexamantane #12 | 6-12 | 44 | 205 | 1024 | 1.72 |
| Hexamantane #13 | 6-13 | 36 | 187 | 935 | 1.57 |
| Hexamantane #14 | 6-14 | 39 | 193 | 967 | 1.63 |
| Hexamantane #15 | 6-15 | 45 | 207 | 1036 | 1.74 |
| Hexamantane #16 | 6-16 | 44 | 205 | 1024 | 1.72 |
| Hexamantane #17 | 6-17 | 49 | 217 | 1083 | 1.82 |
| Heptamantane #1 | 7-1 | 45 | 207 | 1036 | 1.74 |
| Heptamantane #2 | 7-2 | 41 | 198 | 989 | 1.66 |
| Heptamantane #3 | 7-3 | 61 | 238 | 1190 | 2.00 |
| Heptamantane #4A | 7-4A | 90 | 304 | 1519 | 2.56 |
| Heptamantane #4B | 7-4B | 90 | 304 | 1519 | 2.56 |
| Heptamantane #5 | 7-5 | 76 | 270 | 1349 | 2.27 |
| Heptamantane #6 | 7-6 | 67 | 251 | 1253 | 2.11 |
| Heptamantane #7 | 7-7 | — | — | — | — |
| Heptamantane #8 | 7-8 | 59 | 234 | 1172 | 1.97 |
| Heptamantane #9A | 7-9A | 60 | 236 | 1181 | 1.99 |
| Heptamantane #9B | 7-9B | 62 | 240 | 1200 | 2.02 |
| Heptamantane #9C | 7-9C | 78 | 274 | 1370 | 2.31 |
| Heptamantane #10 | 7-10 | 86 | 291 | 1455 | 2.45 |
| Heptamantane #11 | 7-11 | — | — | — | — |
| Heptamantane #12 | 7-12 | — | — | — | — |
| Heptamantane #13A | 7-13A | 58 | 233 | 1163 | 1.96 |
| Heptamantane #13B | 7-13B | 74 | 266 | 1328 | 2.24 |
| Heptamantane #13C | 7-13C | 90 | 304 | 1519 | 2.56 |
| Heptamantane #14 | 7-14 | 70 | 257 | 1285 | 2.16 |

Fig. 4B cont'd

| Higher Diamondoid | Compound Reference Number | Fraction Number | Elution Time (min.) | Elution Volume (mL) | Elution Volume Relative to 4-1 |
|---|---|---|---|---|---|
| Octamantane #1 | 8-1 | 81 | 280 | 1402 | 2.36 |
| Octamantane #2 | 8-2 | 83 | 285 | 1423 | 2.40 |
| Octamantane #3 | 8-3 | 64 | 244 | 1221 | 2.06 |
| Octamantane #4 | 8-4 | — | — | — | — |
| Octamantane #5 | 8-5 | 63 | 242 | 1211 | 2.04 |
| Octamantane #6 | 8-6 | 79 | 276 | 1381 | 2.32 |
| Octamantane #7 | 8-7 | 71 | 259 | 1296 | 2.18 |
| Octamantane #8 | 8-8 | 84 | 287 | 1434 | 2.41 |
| Octamantane #9 | 8-9 | 74 | 266 | 1328 | 2.24 |
| Octamantane #10 | 8-10 | 80 | 280 | 1402 | 2.36 |
| Octamantane #11 | 8-11 | 85 | 289 | 1445 | 2.43 |
| Nonamantane #1 | 9-1 | 89 | 297 | 1487 | 2.50 |
| Decamantane #1 | 10-1 | 83 | 285 | 1423 | 2.40 |
| Decamantane #2 | 10-2 | — | — | — | — |
| Undecamantane#1 | 11-1 | 101 | 355 | 1774 | 2.99 |

ODS HPLC Whatman ODS-II 10/50
(2 Columns in series), acetone mobile phase @5.0 mL/min.

Flow Chart: Strategy for the Derivatization of Higher Diamondoids          Fig. 5

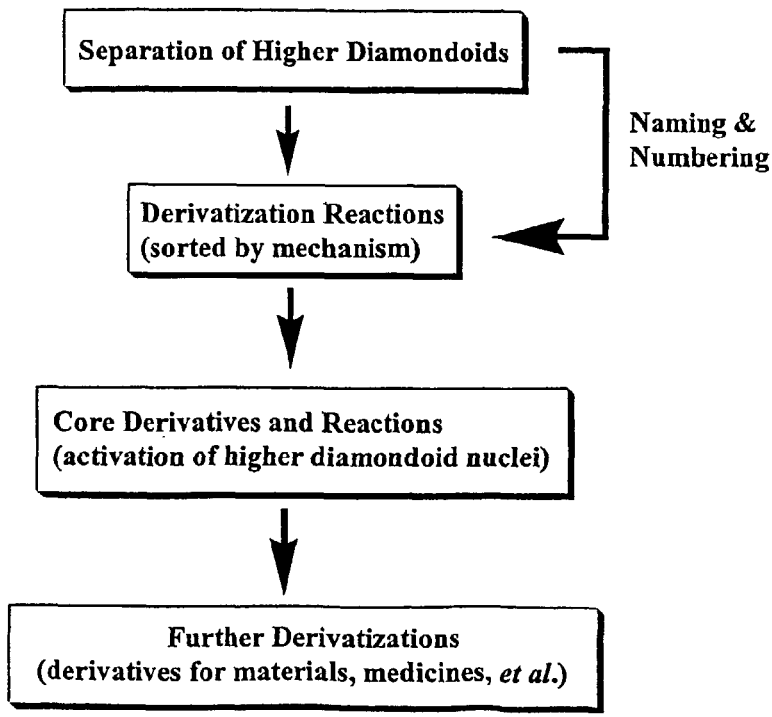

Representative Ways of Generation of Higher Diamondoid Cations

Representative $S_N1$ Reactions of Higher Diamondoid Carbocations

TIC of a Feedstock Containing a Mixture of Tetramantanes and Alkyltetramantanes as the Starting Material

*Alkyltetramantane
+Alkane impurity

TIC of Bromination Products of the Above Feedstock Containing a Mixture of Tetramantanes and Alkyltetramantanes GCMS of the Mono-brominated Tetramantane @ 12.038 min.

GCMS of the Tri-brominated Tetramantane @ 17.279 min.

TIC of Hydroxylated Products from the Brominated Compounds @ 12.5 to 17.5 min.

GCMS of the Mono-Hydroxylated Tetramantane @ 15.329 min.

TIC of the Acetaminated Products from the Hydroxylated Compounds @ 16.0 to 22.0 min.

GCMS of the Monoacetaminated Tetramantane @ 18.098 min.

TIC of the Aminated Products from the Acetaminated Compounds @ 10.5 to 23.5 min.

GCMS of the Monoaminated Tetramantane @ 19.107 min.

FUNCTIONALIZED HIGHER DIAMONDOIDS

This application is a continuation-in-part of U.S. Ser. No. 10/046,486 filed Jan. 16, 2002, now U.S. Pat. No. 6,858,700 which is incorporated herein by reference. U.S. Ser. No. 10/046,486 claims priority to U.S. Ser. No. 60/348,032 filed Oct. 26, 2001 and to U.S. Ser. No. 60/262,842 filed Jan. 19, 2001. This application also claims priority to U.S. Ser. No. 60/397,341 filed Jul. 18, 2002. This application further claims priority to U.S. Ser. No. 60/336,722, filed Dec. 7, 2001.

BACKGROUND OF THE INVENTION

Field of the Invention

The present invention is directed to functionalized higher diamondoids. These are compounds having a higher diamondoid nucleus with one or more functional groups covalently attached. The functionalized higher diamondoids have applications as chemical intermediates, as materials for construction of nano-devices for nanotechnology, as lubricants and coatings and as components of biologically reactive materials and the like.

REFERENCES

The following publications and patents are provided for background information and some are cited in this application as superscript numbers:

[1] Fort, Jr., et al., *Adamantane: Consequences of the Diamondoid Structure*, Chem. Rev., 64:277-300 (1964).

[2] Capaldi, et al., *Alkenyl Adamantanes*, U.S. Pat. No. 3,457,318, issued Jul. 22, 1969.

[3] Thompson, *Polyamide Polymer of Diamino Methyl Adamantane and Dicarboxylic Acid*, U.S. Pat. No. 3,832,332, issued Aug. 27, 1974.

[4] Baum, et al., *Ethynyl Adamantane Derivatives and Methods of Polymerization Thereof*, U.S. Pat. No. 5,017,734, issued May 21, 1991.

[5] Ishii, et al., *Polymerizable Adamantane Derivatives and Process for Producing Same*, U.S. Pat. No. 6,235,851, issued May 22, 2001

[6] McKervey, et al., *Synthetic Approaches to Large Diamondoid Hydrocarbons*, Tetrahedron, 36:971-992 (1980).

[7] Lin, et al., *Natural Occurrence of Tetramantane (C22H28), Pentamantane (C26H32) and Hexamantane (C30H36) in a Deep Petroleum Reservoir*, Fuel, 74(10):1512-1521 (1995).

[8] Chen, et al., *Isolation of High Purity Diamondoid Fractions and Components*, U.S. Pat. No. 5,414,189, issued May 9, 1995.

[9] Balaban et al., *Systematic Classification and Nomenclature of Diamond Hydrocarbons-I*, Tetrahedron. 34, 3599-3606 (1978).

[10] Gerzon et al., *The Adamantyl Group in Medicinal Agents. 1. Hypoglycemic N-Arylsulfonyl-N-adamantylureas*, Vol. 6, pgs. 760-763, November 1963.

[11] Marshall et al., *Further Studies on N-Arylsulfonyl-N-alkylureas*, Vol. 6, pgs. 60-63, January 1963.

[12] Marshall et al., *Some N-Arylsulfonyl-N-alkylureas*, Vol. 3, pgs. 927-929, Jun. 1958.

[13] Reinhardt, *Biadamantane and Some of its Derivatives*, Vol. 27, pgs. 3258-3261, September 1962.

[14] Sasaki et al., *Synthesis of Adamantane Derivatives. II. Preparation of Some Derivatives from Adamantylacetic Acid*, Vol. 41, No. 1, pgs. 238-240, June 1968.

[15] Stetter et al, *Ein Beitrag zur Frage der Reaktivitat von Bruckenkopf-Carboniumionen*, Uber Verbindungen mit Urotropin-Struktur, XXVI, pgs. 550-555, 1963.

[16] Hass et al, *Adamantyloxycarbonyl, a New Blocking Group. Preparation of 1-Adamantyl Chloroformate*, Journal of the American Chemical Society, 88:9, pgs. 1988-1992, May 5, 1966

[17] Stetter et al, *Neue Moglichkeiten der Direktsubstitution am Adamantan*, Uber Verbindungen mit Urotropin-Struktur, XLIII, Chem. Ber. 102, pgs. 3357-3363, 1969.

[18] von H. U. Daeniker, 206. *1-Hydrazinoadamantan*, Helvetica Chimica Acta, Vol. 50, Fasciculus, pgs. 2008-2010, 1967

[19] Stetter et al, *Uber Adamantan-phosphonsaure-(1)-dichlorid*, Uber Verbindungen mit Urotropin-Struktur, XLIV, Chem. Ber. 102, p. 3364-3366, 1969.

[20] Lansbury et al, *Some Reactions of α-Metalated Ethers*, The Journal of Organic Chemistry, Vol. 27, No. 6, pgs. 1933-1939, Jun. 12, 1962.

[21] Stetter et al, *Herstellung von Derivaten des 1-Phenyladamantans*, Uber Verbindungen mit Urotropin-Struktur, XXXI, pgs. 3488-3492, 1964.

[22] Nordlander et al, *Solvolysis of 1-Adamantylcarbinyl and 3-Homoadamantyl Derivatives. Mechanism of the Neopentyl Cation Rearrangement*, Journal of the American Chemical Society, 88:19, Oct. 5, 1966.

[23] Sasaki et al, *Substitution Reaction of 1-Bromoadamantane in Dimethyl Sulfoxide: Simple Synthesis of 1-Azidoadamantane*, Journal of the American Chemical Society, 92:24, Dec. 2, 1970.

[24] Chakrabarti et al, *Chemistry of Adamantane. Part II. Synthesis of 1-Adamantyloxyalkylamines*, Tetrahedron Letters No. 60, pgs. 6249-6252, Pergamon Press, Great Britain, 1968.

[25] Stetter et al. *Derivate des 1-Amino-adamantans*, Uber Verbindungen mit Urotropin-Struktur, XXIV, pgs. 2302-2304, 1962.

[26] Stetter et al, *Zur Kenntnis der Adamantan-carbonsaure-(1)*, Uber Verbindungen mit Urotropin-Struktur, XVII, pgs. 1161-1166, 1960.

[27] Makarova et al, *Psychotropic Activity of Some Aminoketones Belonging to the Adamantane Group*, Pharmaceutical Chemistry Journal, Vol. 34, No. 6, 2000.

All of the above publications and patents are herein incorporated by reference in their entirety to the same extent as if each individual publication or patent was specifically and individually indicated to be incorporated by reference in its entirety.

BACKGROUND INFORMATION

Diamondoids are cage-shaped hydrocarbon molecules possessing rigid structures which are tiny fragments of a diamond crystal lattice as described by Fort, Jr., et al.[1] Adamantane is the smallest member of the diamondoid series and consists of a single cage structure of the diamond crystal lattice. Diamantane contains two adamantane subunits face-fused to each other, triamantane three, tetramantane four, and so on. While there is only one isomeric form of adamantane, diamantane and triamantane, there are four different isomeric tetramantanes (i.e., four different shapes containing four adamantane subunits). Two of the isomeric tetramantanes are enantiomeric. The number of possible isomers increases rapidly with each higher member of the diamondoid series.

Among other properties, diamondoids have by far the most thermodynamically stable structures of all possible hydrocarbons that possess their molecular formulas due to the fact that diamondoids have the same internal "crystalline lattice" structure as diamonds. It is well established that diamonds exhibit extremely high tensile strength, extremely low chemical reactivity, electrical resistivity greater than aluminum trioxide ($Al_2O_3$), excellent thermal conductivity, and superb optical properties.

Adamantane, which is commercially available, has been studied extensively. The studies have been directed to a number of areas, such as thermodynamic stability, functionalization and properties of adamantane-containing materials. For instance, the following patents describe adamantane derivatives and adamantane-based polymers. U.S. Pat. No. 3,457,318 teaches the preparation of polymers from alkenyl adamantanes;[2] U.S. Pat. No. 3,832,332 describes a polyamide polymer formed from alkyladamantane diamine;[3] U.S. Pat. No. 5,017,734 discusses the formation of thermally stable resins from ethynyl adamantane derivatives;[4] and, U.S. Pat. No. 6,235,851 reports the synthesis and polymerization of a variety of adamantane derivatives.[5]

The higher diamondoids, which include the tetramantanes, pentamantanes, etc., have received comparatively little attention. In fact, prior to the work of inventors Dahl and Carlson embodied in U.S. Patent Application Ser. No. 60/262,842 filed Jan. 19, 2001 and numerous subsequent filings, see for example:

U.S. Ser. No. 10/012,333;
U.S. Ser. No. 10/012,334;
U.S. Ser. No. 10/012,335;
U.S. Ser. No. 10/012,336;
U.S. Ser. No. 10/012,337;
U.S. Ser. No. 10/012,545;
U.S. Ser. No. 10/012,546;
U.S. Ser. No. 10/012,547;
U.S. Ser. No. 10/012,704;
U.S. Ser. No. 10/012,709;
U.S. Ser. No. 10/017,821; and
U.S. Ser. No. 10/046,486;

all filed on Dec. 12, 2001 and U.S. Ser. No. 10/052,636 filed on Jan. 17, 2002 and all incorporated herein by reference, these compounds were nearly hypothetical with only one such compound having been synthesized and a few others tentatively identified (but not isolated). More specifically, McKervey, et al. reported the synthesis of anti-tetramantane in low yields using a laborious, multistep process.[6] Lin, et al. suggested the existence of tetramantane, pentamantane and hexamantane in deep petroleum reservoirs from mass spectroscopy alone and without any attempt to isolate materials.[7] The possible presence of tetramantane and pentamantane in pot material recovered after a distillation of a diamondoid-containing feedstock has been discussed by Chen, et al.[8]

The materials discussed in the patent applications described above are the higher diamondoids themselves and higher diamondoids containing one or more alkyl substituents, all as compounds identified and isolated from various petroleum feedstocks. While these materials are of great technical and commercial importance in view of their special structural, physical and chemical properties, it is also to be understood that it could also be advantageous to chemically modify these hydrocarbon materials so as to introduce functional groups. It is the process of functionalization and the novel compounds it provides that is the subject of this invention.

SUMMARY OF THE INVENTION

This invention is directed to functionalized higher diamondoids having at lest one functional group. Preferably these derivatives have the following Formula I:

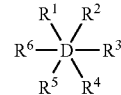

I wherein D is a higher diamondoid nucleus; and, $R^1$, $R^2$, $R^3$, $R^4$, $R^5$ and $R^6$ are each independently selected from a group consisting of hydrogen and covalently bonded functional groups, provided that there is at least one functional group. More preferably the functionalized higher diamondoids contain either one or two functional groups.

In one aspect, as described in U.S. Ser. No. 10/046,486, in the functionalized higher diamondoids represented by Formula I, $R^1$, $R^2$, $R^3$, $R^4$, $R^5$ and $R^6$ are preferably independently selected from a group of moieties consisting of —H, —F, —Cl, —Br, —I, —OH, —SH, —$NH_2$, —$NHCOCH_3$, —NHCHO, —$CO_2H$, —$CO_2R'$, —COCl, —CHO, —$CH_2OH$, =O, —$NO_2$, —CH=$CH_2$, —C≡CH and —$C_6H_5$; where R' is alkyl (preferably ethyl) provided that $R^1$, $R^2$, $R^3$, $R^4$, $R^5$ and $R^6$ are not all hydrogen. Typically one or two of $R^1$-$R^6$ are nonhydrogen moieties and the remaining R's are hydrogens.

Some functionalized higher diamondoids can be prepared from higher diamondoid in a single reaction step. These materials are referred to herein as "primary functionalized higher diamondoids" and include, for example, higher diamondoids of Formula I wherein the functionalizing groups are halogens, such as -bromos and -chloros, -oxides, -hydroxyls and -nitros as well as other derivatives formed in one reaction from a higher diamondoid.

In another aspect, the functionalized higher diamondoids are materials prepared from a primary functionalized higher diamondoid by one or more subsequent reaction steps. These materials are sometimes referred to herein as "secondary functionalized higher diamondoids." It will be appreciated that in some cases one primary functionalized higher diamondoid may be conveniently formed by conversion of another primary material. For example, a poly-bromo material can be formed either by single step bromination or by several repeated brominations. Similarly, a hydroxyl diamondoid can be formed directly from a diamondoid in one step or can be prepared by reaction of a bromo-diamondoid, a diamondoid-oxide or the like. Notwithstanding this, to avoid confusion, the primary materials will not be included here in the representative secondary materials. They will, however, be depicted in various figures showing reactions for forming primary and secondary materials to depict both routes to them.

The functionalized groups available for synthesis of secondary functionalized higher diamondoids can be selected from a wide range of groups including chloro, bromo, hydroxides, etc. Thus, the following types of secondary materials are merely representatives.

Representative secondary functionalized higher diamondoid functional groups include fluoro, iodo, thio, sulfonyl halide, sulfonates, alkyl, haloalkyl, alkoxyl, haloalkenyl, alkynyl, haloalkynyl, hydroxyalkyl, heteroaryl, alkylthio, alkoxy; aminoalkyl, aminoalkoxy, aryl, heterocycloalkoxy, cycloalkyloxy, aryloxy, and heteroaryloxy.

Other functional groups that can be present in secondary functionalized higher diamondoids are represented by the formula —C(O)Z wherein Z is hydrogen, alkyl, halo, haloalkyl, halothio, amino, monosubstituted amino, disubstituted amino, cycloalkyl, aryl, heteroaryl, heterocyclic; by —CO$_2$Z wherein Z is as defined previously; by —R$^7$COZ and —R$^7$CO$_2$Z wherein R$^7$ is alkylene, aminoalkylene, or haloalkylene and Z is as defined previously; by —NH$_2$; —NHR', —NR'R'', and —N$^+$R'R''R''' wherein R', R'', and R''' are independently alkyl, amino, thio, thioalkyl, heteroalkyl, aryl, or heteroaryl; by —R$^8$NHCOR$^9$ wherein R$^8$ is —CH$_2$, —OCH$_2$, —NHCH$_2$, —CH$_2$CH$_2$, —OCH$_2$CH$_2$ and R$^9$ is alkyl, aryl, heteroaryl, aralkyl, or heteroaralkly; and by —R$^{10}$CONHR$^{11}$ wherein R$^{10}$ is selected from —CH$_2$, —OCH$_2$, —NHCH$_2$, —CH$_2$CH$_2$, and —OCH$_2$CH$_2$, and R$^{11}$ is selected from alkyl, aryl, heteroaryl, aralkyl, and heteroaralkyl.

In a further aspect, one or more of the functional groups on the functionalized higher diamondoids may be of the formulae:

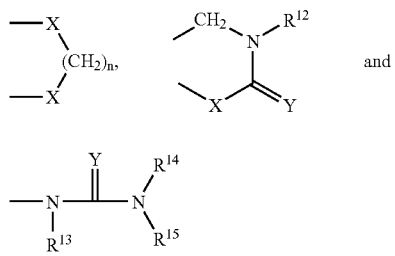

wherein n is 2 or 3; X is —O—, —S—, or —C(O)—; Y is =O or =S; and R$^{12}$, R$^{13}$, R$^{14}$, and R$^{15}$ are independently hydrogen, alkyl, heteroalkyl, aryl or heteroaryl; =N—Z'', wherein Z'' is hydrogen, amino, hydroxyl, alkyl,

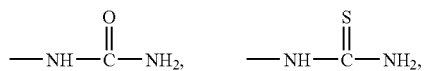

cyano, cyanoalkyl, cyanoaryl, or cyanoalkylamino.

In a further embodiment, one or more of the functional groups on the functionalized higher diamondoid is —NHR', —NR'R'', —N$^+$R'R''R''', or —NHQ'' wherein R', R'', and R''' independently are hydrogen; aryl; heteroaryl with up to 7 ring members; alkyl; alkenyl; or alkynyl, wherein the alkyl, alkenyl and alkynyl residues can be branched, unbranched or cyclized and optionally substituted with halogen, aryl or heteroaryl with up to 7 ring members; or R' and R'' together with the nitrogen atom form a heterocyclic group with up to 7 ring members. Q'' is thio, thioalkyl, amino, monosubstituted amino, disubstituted amino, or trisubstituted amino with an appropriate counterion such as halogen, hydroxide, sulfate, nitrate, phosphate or other anion.

In still a further embodiment, the functional group on the functionalized higher diamondoid is —COOR$^{16}$ wherein R$^{16}$ is alkyl, aryl, or aralkyl; —COR$^{17}$, wherein R$^{17}$ is alkyl, aryl, or heteroalkyl, —NHNHO, —R$^{18}$NHCOR$^{19}$ wherein R$^{18}$ is absent or selected from alkyl, aryl, or aralkyl, R$^{19}$ is hydrogen, alkyl, —N$_2$, aryl, amino, or —NHR$^{20}$ wherein R$^{20}$ is hydrogen, —SO$_2$-aryl, —SO$_2$-alkyl, or —SO$_2$-aralkyl, —CONHR$^{21}$ wherein R$^{21}$ is hydrogen, alkyl, and aralkyl; —CSNHR$^{21}$ wherein R$^{21}$ is as defined above; and —NR$^{22}$—(CH$_2$)$_n$—NR$^{23}$R$^{24}$, wherein R$^{22}$, R$^{23}$, R$^{24}$ are independantly selected from hydrogen, alkyl, and aryl, and n is from 1 to 20.

In an additional embodiment, the functional group on the functionalized higher diamondoid may be —N=C=S; —N=C=O; —R—N=C=O; —R—N=C=S; —N=S=O; or —R—N=S=O wherein R is alkyl; —PH$_2$; —POX$_2$ wherein X is halo; —PO(OH)$_2$; —OSO$_3$H; —SO$_2$H; —SOX wherein X is halo; —SO$_2$R wherein R is alkyl; —SO$_2$OR wherein R is alkyl; —SONR$^{26}$R$^{27}$ wherein R$^{26}$ and R$^{27}$ are independently hydrogen or alkyl; —N$_3$; —OC(O)Cl; or —OC(O)SCl.

In a further aspect, the functionalizing group may form a covalent bond to two or more higher diamondoids and thus serves as a linking group between the two or more diamondoids. This provides functionalized higher diamondoids of Formula II:

$$D—L—(D)_n \qquad \text{II}$$

wherein D is a higher diamondoid nucleus and L is a linking group and n is 1 or more such as 1 to 10 and especially 1 to 4.

In this embodiment, the linking group L may be —N=C—N—;

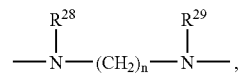

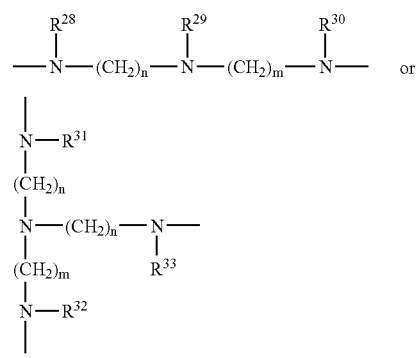

wherein R$^{28}$, R$^{29}$, R$^{30}$, R$^{31}$, R$^{32}$, R$^{33}$ are independently hydrogen or alkyl, and n and m are independently from 2 to 20;

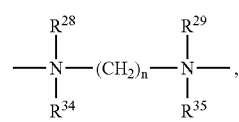

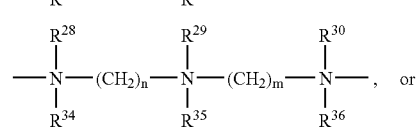

-continued

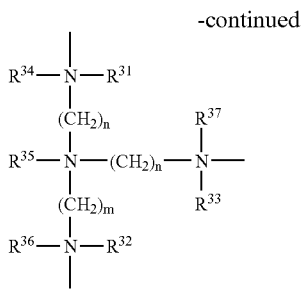

wherein $R^{28}$, $R^{29}$, $R^{30}$, $R^{31}$, $R^{32}$ and $R^{33}$ are hydrogen or alkyl; $R^{34}$, $R^{35}$, $R^{36}$, and $R^{37}$ are independently absent or hydrogen or alkyl with the proviso that at least one of $R^{34}$, $R^{35}$, $R^{36}$, and $R^{37}$ is present; and n and m are independently from 2 to 20 or the like. The counterion may any acceptable monovalent anion, for example, halogen, hydroxide, sulfate, nitrate, phosphate, and the like.

In another aspect, the present invention relates to functionalized higher diamondoids of Formula III:

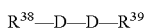   III wherein each D is a higher diamondoid nucleus and $R^{38}$ and $R^{39}$ are substituents on the higher diamondoid nucleus and are independently hydrogen or a functionalizing group. Preferably the material contains either 1 or 2 functional groups. Preferably $R^{38}$ and $R^{39}$ are halo; cyano; aryl; arylalkoxy; aminoalkyl; or —$COOR^{40}$ wherein $R^{40}$ is hydrogen or alkyl.

In an additional aspect, the present invention provides salts, individual isomers, and mixtures of isomers of higher diamondoid derivatives of Formulae I, II, and III.

The functionalized higher diamondoids of the present invention are useful in a number of diverse areas, including, for instance, nanotechnology, drugs, drug carriers, pharmaceutical compositions, precursors for the synthesis of biologically active compounds, photoresist materials and/or resist compositions for far UV lithography, synthetic lubricants, heat resistant materials and solvent-resistant resins, and so on. For example, the higher diamondoid derivatives of the present invention have desirable lipophilic properties, which may improve the bioavailability of pharmaceutically active groups attached thereto. Also for example, the higher diamondoid derivatives of the present invention have sizes comparable to protein fragments, which may improve their efficacy. Further for example, the substituted isomers of the higher diamondoids from a rigid structure and thus may be selected such that they provide specific shape interaction with chiral biological molecules. These chiral biological molecules include, for example, enzymes, receptors and the like. The higher diamondoid derivatives of the present invention may also be useful as chemical intermediates for the synthesis of further functionalized higher diamondoid derivatives to form a variety of useful materials. For example, the diversity of substitution positions on the higher diamondoids of the present invention which takes a variety of forms can find a variety of applications. Such materials include composite matrix resins, structural adhesives and surface files that are used for aerospace structural applications. Furthermore, coating layers or molded products with excellent optical, electrical or electronic and mechanical properties are produced for use in optical fibers, photoresist compositions, conduction materials, paint compositions and printing inks. In addition, higher diamondoid derivative containing materials will have high thermal stability making them suitable for use in environments requiring such stability including for example, devices such as semiconductors, coatings for refractory troughs or other high temperature applications.

These diverse utilities give rise to aspects of this invention related to the use of the derivatized products. For example, if the functionalizing groups are pharmaceutically active, this can lead to pharmaceutically active functionalized higher diamondoid which can be used in pharmaceuticals and methods of treatment. Similarly, if the functionalized higher diamondoid is of a size and shape which interacts with biological molecules or groups, the functionalizing group need only be pharmaceutically acceptable to achieve biological usefulness.

Thus, in a further aspect, the present invention provides pharmaceutical compositions containing a therapeutically effective amount of a pharmaceutically active functionalized higher diamondoid of formula I, II, and III.

In another aspect, the present invention provides a method of treatment of a disease, in particular rheumatoid arthritis, osteoarthritis, psoriasis, allergic dermatitis, asthma, hyperresponsiveness of the airway, septic shock, glomeruloneplhritis, irritable bowel disease, Crohn's disease, ulcerative colitis, atherosclerosis, growth and metastases of malignant cells, myocardial ischaemia, myoblastic leukaemia, diabetes, Alzheimer's disease, osteoporosis, burn injury, stroke, varicose veins, meningitis, idiopathic Parkinson's Disease, postencephalitic parkinsonism, and symptomatic parkinsonism resulting from damage to the nervous system caused by carbon monoxide intoxication as well as in the treatment of parkinsonism associated with cerebral arteriosclerosis, particularly in elderly patients, cardiac, circulatory and vascular diseases, especially cardiac insufficiency; depression; hypertension; drug-induced extrapyramidal reactions; bacterial infections; and viral infections, comprising administration of a therapeutically effective amount of a pharmaceutically active functionalized higher diamondoid of Formulae I, II and III or its pharmaceutically acceptable salt. The present invention preferably provides a method of treatment of viral infections, in particular HIV, comprising administration of a therapeutically effective amount of a functionalized higher diamondoid of Formulae I, II, and III or their pharmaceutically acceptable salt.

The functionalized higher diamondoids of the present invention may also be useful as intermediates for the synthesis of further functionalized higher diamondoids.

BRIEF DESCRIPTION OF THE DRAWINGS

FIGS. 4A and 4B are compilations of the GC/MS and HPLC properties of various higher diamondoids employed in this invention.

FIG. 5 shows a flow chart for a strategy of functionalization of higher diamondoids.

DETAILED DESCRIPTION OF THE INVENTION

Figure 1:
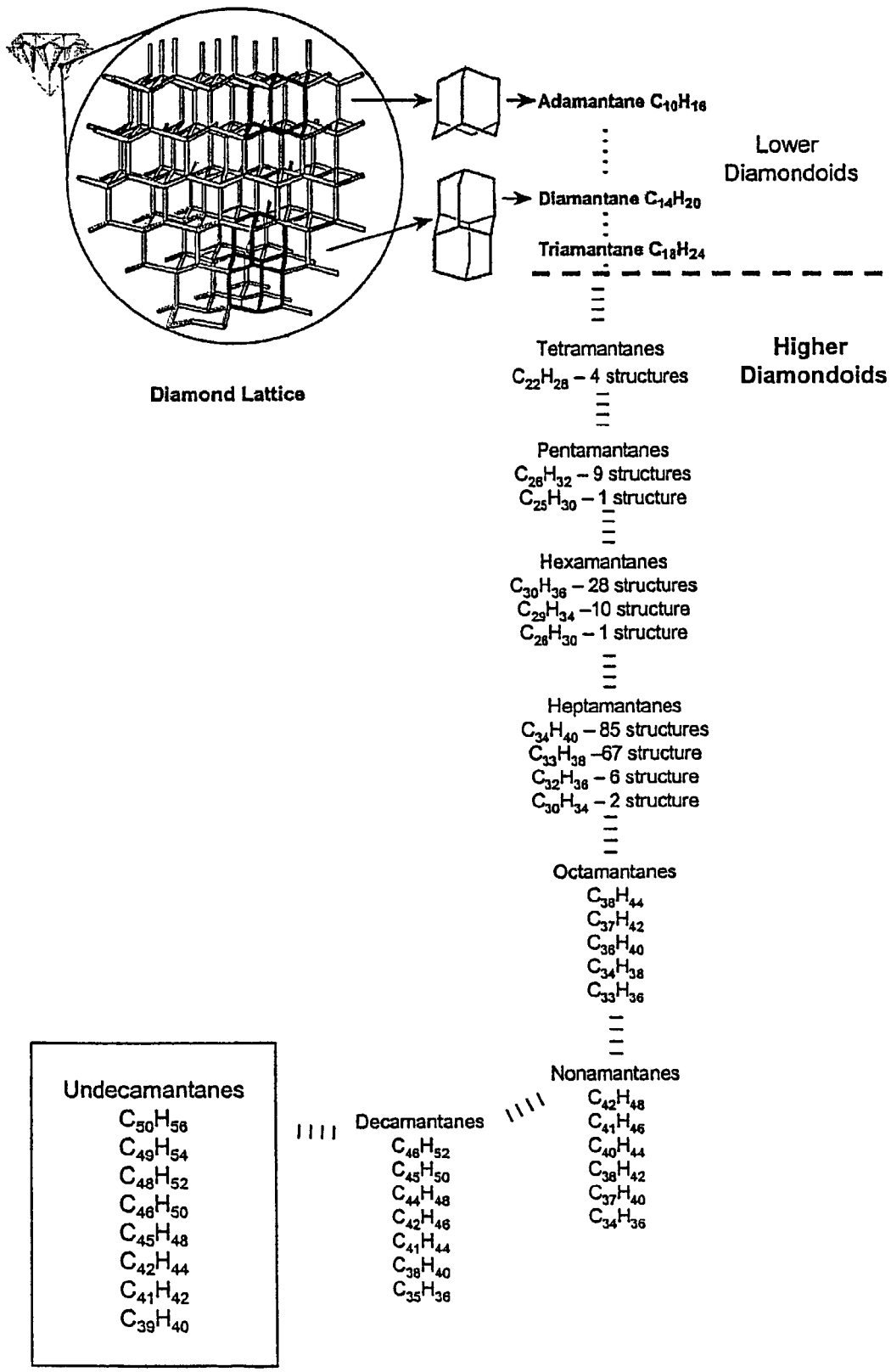
FIG. 1 illustrates the cage-shaped structure of diamondoids and their correlation to diamonds. Specifically, illustrated is the correlation of the structures of diamondoids to subunits of the diamond crystal lattice.

This Detailed Description is presented in the following subsections:
Definitions
Higher Diamondoids and Their Recovery
Derivatization of Higher Diamondoid
Illustrative Embodiments
Utility Definitions As used herein, the following terms have the following meanings.

The term "diamondoid" refers to substituted and unsubstituted caged compounds of the adamantane series including substituted and unsubstituted adamantane, diamantane, triamantane, tetramantane, pentamantane, hexamantane, heptamantane, octamantane, nonamantane, decamantane, undecamantane, and the like and also including various molecular weight forms of these components and including isomers of these forms. Substituted diamondoids preferably comprise from 1 to 10 and more preferably 1 to 4 alkyl substituents. "Diamondoids" include "lower diamondoids" and "higher diamondoids".

The term "lower diamondoids" or "adamantane, diamantane and triamantane" refers to any and/or all unsubstituted and substituted derivatives of adamantane, diamantane or triamantane. The unsubstituted lower diamondoids show no isomers and are readily synthesized, distinguishing them from the "higher diamondoids".

The term "higher diamondoids" refers to any and/or all substituted and unsubstituted tetramantanes; to any and/or all substituted and unsubstituted pentamantanes; to any and/or all substituted and unsubstituted hexamantanes; to any and/or all substituted and unsubstituted heptamantanes; to any and/or all substituted and unsubstituted octamantanes; to any and/or all substituted and unsubstituted nonamantanes; to any and/or all substituted and unsubstituted decamantanes; to any and/or all substituted and unsubstituted undecamantanes; as well as mixtures of the above as well as isomers and stereoisomers.

The term "functionalized higher diamondoid" refers to a higher diamondoid which has had at least one of its hydrogens replaced by a covalently bonded-functional moiety. The portion of the higher diamondoid present in a functionalized higher diamondoid derivative is referred to as a "higher diamondoid nucleus."

The term "alkyl" refers to straight and branched chain saturated aliphatic groups typically having from 1 to 20 carbon atoms, more preferably 1 to 6 atoms ("lower alkyls"), as well as cyclic saturated aliphatic groups typically having from 3 to 20 carbon atoms and preferably from 3 to 6 carbon atoms ("lower alkyls" as well). The terms "alkyl" and "lower alkyl" are exemplified by groups such as methyl, ethyl, propyl, butyl, isopropyl, isobutyl, sec-butyl, t-butyl, cyclopropyl, cyclobutyl, cyclopentyl, cyclohexyl and the like. An "added alkyl" is an alkyl that has been aynthetically bonded to a higher diamondoid nucleus.

The term "substituted alkyl" refers to an alkyl group as defined above, having from 1 to 5 substituents, and preferably 1 to 3 "substituents". As used in these definitions the term "substituents" include materials selected from the group consisting of alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Similarly a material is "substituted" when it has had one or more hydrogens replaced by one or more of these substituents.

The term "alkylene" refers to a divalent (branched or unbranched) saturated hydrocarbon chain, preferably having from 1 to 20 carbon atoms, more preferably 1 to 10 carbon atoms and even more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents.

The term "alkaryl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monovalent unsaturated hydrocarbon group preferably having from 2 to 20 carbon atoms, more preferably 2 to 10 carbon atoms and even more preferably 2 to 6 carbon atoms and having at least 1 and preferably from 1-6 sites of vinyl unsaturation. Preferred alkenyl groups include ethenyl (—CH═CH$_2$), n-propenyl (—CH$_2$CH═CH$_2$), iso-propenyl (—C(CH$_3$)═CH$_2$), and the like.

The term "substituted alkenyl" refers to an alkenyl group as defined above having from 1 to 5 substituents, and preferably 1 to 3 substituents.

The term "alkenylene" refers to a divalent of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1-6 sites of vinyl unsaturation. This term is exemplified by groups such as ethenylene (—CH═CH—), the propenylene isomers (e.g., —CH$_2$CH═CH— and —C(CH$_3$)═CH—) and the like.

The term "substituted alkenylene" refers to an alkenylene group as defined above having from 1 to 5 substituents, and preferably from 1 to 3 substituents.

The term "alkynyl" refers to a monovalent unsaturated hydrocarbon preferably having from 2 to 20 carbon atoms, more preferably 2 to 20 carbon atoms and even more preferably 2 to 6 carbon atoms and having at least 1 and preferably from 1-6 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents.

The term "alkynylene" refers to a divalent unsaturated hydrocarbon preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynylene groups include ethynylene (—C≡C—), propargylene (—CH$_2$C≡C—) and the like.

The term "substituted alkynylene" refers to an alkynylene group as defined above having from 1 to 5 substituents, and preferably 1 to 3 substituents.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl or substituted alkyl or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl or substituted alkyl.

The term "aminoacyloxy" or "alkoxycarbonylamino" refers to the group —NRC(O)OR where each R is independently hydrogen, alkyl, a substituted alkyl.

The term "acyloxy" refers to the groups alkyl-C(O)O—, and substituted alkyl-C(O)O—.

The term "aryl" refers to an unsaturated aromatic carbocyclic group of from 6 to 20 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents.

The term "aryloxy" refers to the group aryl-O— wherein the aryl group is as defined above including optionally substituted aryl groups as also defined above.

The term "arylene" refers to the divalent derived from aryl (including substituted aryl) as defined above and is exemplified by 1,2-phenylene, 1,3-phenylene, 1,4-phenylene, 1,2-naphthylene and the like.

The term "amino" refers to the group —$NH_2$.

The term "substituted amino" refers to the group —NRR where at least one R is independently selected from the group consisting of alkyl, and substituted alkyl and any other R is hydrogen.

The term "carboxyalkyl" or "alkoxycarbonyl" refers to the groups "—C(O)O-alkyl", and "—C(O)O-substituted alkyl".

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents.

The term "heteroaryloxy" refers to the group heteroaryl-O—.

The term "heteroarylene" refers to the divalent group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "heterocycle" or "heterocyclic" refers to a monovalent saturated or unsaturated group having a single ring or multiple condensed rings, from 1 to 20 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents.

The term "heterocyclooxy" refers to the group heterocyclic-O—.

The term "thioheterocyclooxy" refers to the group heterocyclic-S—.

The term "thiol" refers to the group —SH.

"Heteroalkyl" means an alkyl or cycloalkyl as defined above, carrying a substituent containing a heteroatom selected from N, O, S, $S(O)_n$ where n is an integer from 0 to 2. Representative substituents include —$NR_aR_b$, —$OR_a$, —$SR_a$, or —$S(O)_nR_c$, wherein n is an integer from 0 to 2. $R_a$ is hydrogen, alkyl, haloalkyl, cycloalkyl, cycloalkylalkyl, optionally substitued phenyl, optionally substituted phenylalkyl, optionally substituted heteroaryl, or —COR where R is alkyl. $R_b$ is hydrogen alkyl, —$S(O)_2R$ where R is alkyl or hydroxylalkyl, —$SO_2$, —NRR' where R and R' are independently hydrogen or alkyl, —CONR'R" where R' and R" are independently selected from hydrogen or alkyl. $R_c$ is hydrogen, alkyl, cycloalkyl, cycloalkylalkyl, optionally substituted phenyl, optionally substituted heteraryl, amino, monosubstituted amino, or disubstituted amino. Representative examples include, but are not limited to, 2-methoxyethyl, 2-hydroxyethyl, 2-aminoethyl, 2-dimethylaminoethyl, benzyloxymethyl, thiophen-2-ylthiomethyl, and the like.

"Haloalkyl" means alkyl substituted with one or more halogen atoms, preferably one to three halogen atoms, preferably fluorine or chlorine, including those substituted with different halogens. Exemplary groups include —$CH_2Cl$, —$CF_3$, —$CH_2CF_3$, —$CF_2CF_3$, —$CH_2CCl_3$, and the like.

"Hydroxy" or "hydroxyl" means a group of —OH.

"Hydroxyalkyl" means an alkyl substituted with at least one and preferbly 1 to 6 hydroxy group(s), provided that no two hydroxy groups are present on the same carbon atom. Representative examples include, but are not limited to, 2-hydroxyethyl, 2-hydroxypropyl, and the like.

"Alkoxyalkyl" means an alkyl substituted with at least one alkoxy group as defined above; or a branched monovalent hydrocarbon group having 3 to 40 carbon atoms, preferably 3 to 10 carbon atoms, more preferably 3 to 6 carbon atoms, substituted with at least one alkoxy group as defined above. These groups include, for example, -alkylene-O-alkyl and alkylene-O-substituted alkyl Representative examples include methoxymethyl (—$CH_2OCH_3$), 2-methoxyethyl (—$CH_2CH_2OCH_3$), 2-methoxypropyl (—$CH_2$—CH($OCH_3$)—$CH_3$), and the like.

"Alkylthio" or "cycloalkylthio" means a group —SR where R is alkyl or cycloalkyl respectively as defined above, e.g., methylthio, butylthio, cyclopropylthio, and the like.

"Thioalkyl" refers to alkyl group substituted with 1 to 3 thiol group(s) provided that there are no two thiol groups are present on the same carbon atom where alkyl and thiol are as defined herein, such as —$CH_2CH_2SH$, —$CH_2SH$, and the like.

The term "heterocyclothio" refers to the group heterocyclo-S—.

"Monosubstituted amino" means a group —NHR where R is alkyl, acyl, cycloalkyl, alkenyl, cycloalkenyl, alkynyl, aryl, heteroaryl, and heterocyclic, e.g., methylamino (—$NHCH_3$), ethylamino (—$NHCH_2CH_3$), and the like.

"Disubstituted amino" means a group —NRR' where R and R' are independently alkyl, acyl, cycloalkyl, alkenyl, cycloalkenyl, alkynyl, aryl, heteroaryl, and heterocyclic, e.g., dimethylamino (—$N(CH_3)_2$), methylethylamino (—$N(CH_3)CH_2CH_3$), and the like.

"Trisubstituted amino" means a group —$N^+RR'R''$ where R R', and R" independently alkyl, acyl, cycloalkyl, alkenyl, cycloalkenyl, alkynyl, aryl, heteroaryl, and heterocyclic, e.g., trimethylamino (—$N^+(CH_3)_3$), dimethylethylamino (—$N^+(CH_3)_2CH_2CH_3$), and the like.

"Thioketo" refers to S=O.

"Cyano" refers to the group —CN.

"Cyanoaryl" refers to an aryl group with at least one, preferably 1 to 3 cyano substitution(s), such as —$C_6H_4CN$, and the like.

"Cyanoalkyl" refers to an alkyl group with at least one, preferably 1 to 3 cyano substitution(s), such as —$CH_2CN$, and the like.

"Cyanoalkylamino" refers to —NRR' where R is independently hydrogen, alkyl, and substituted alkyl; R' is cyanoalkyl, such as —$NH(CH_2CN)$, —$NCH_3(CH_2CN)$, and the like.

"Nitro" refers to the group —$NO_2$.

"Carbonyl" means a group —C(O)—.

"Aminoalkyl" means an alkyl substituted with at least one —NRR' where R and R' are independently selected from hydrogen, alkyl, or acyl. Representative examples include 2-aminoethyl, 2-N,N-diethylaminopropyl, 2-N-acetylaminoethyl, and the like.

"Pro-drug" means any compound which releases an active parent drug in vivo when such prodrug is administered to a mammalian subject.

A "pharmaceutically acceptable excipient" means an excipient that is useful in preparing a pharmaceutical composition that is generally safe, non-toxic and neither biologically nor otherwise undesirable.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, and the like.

"Pharmacologically acceptable functional group" means a functional group on a compound to be used for a pharmaceutical composition or for making such a compound. These functional groups are generally safe, and non-toxic.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Higher Diamondoids and Their Recovery

As shown in FIG. 1, higher diamondoids are bridged-ring cycloalkanes that have carbon-atom frameworks that can be superimposed on the diamond crystal lattice. They are the tetramers, pentamers, hexamers, heptamers, octamers, nonamers, decamers, etc. of adamantane (tricyclo[3.3.1.1$^{3,7}$]decane) or $C_{10}H_{16}$ in which various adamantane units are face-fused. The higher diamondoids can contain many alkyl substituents. These compounds have extremely rigid structures and have the highest stability of any compound with their formula. There are four tetramantane structures; iso-tetramantane [1(2)3], anti-tetramantane [121] and two enantiomers of skew-tetramantane [123]. There are ten pentamantanes, nine have the molecular formula $C_{26}H_{32}$ (molecular weight 344), and among these nine there are three pairs of enantiomers represented by: [12(1)3], [1234], [1213] with the non-enantiomeric pentamantanes represented by: [12(3)4], [1(2,3)4], [1212]. There also exists a more strained pentamantane, [1231], represented by the molecular formula $C_{25}H_{30}$ (molecular weight 330). Hexamantanes and higher material exist with numerous different structures.

Figure 2:
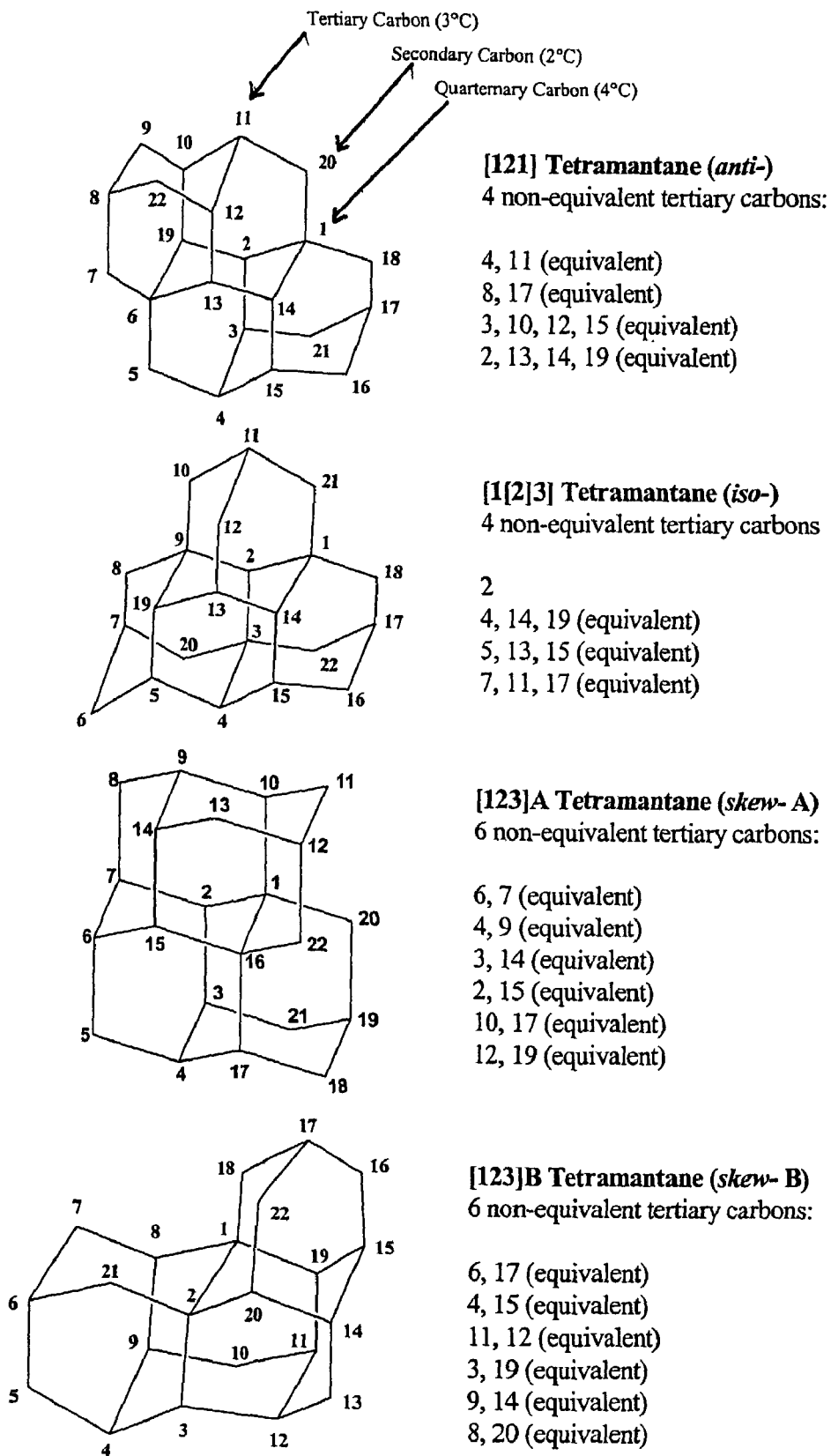
FIG. 2 shows the numbering of four tetramantanes and points out representative secondary, tertiary and quaternary carbon atoms.

FIG. 2 shows a representative carbon-numbering scheme for the four tetramantanes, in which the quaternary, tertiary, and secondary carbons are highlighted. Carbon numbering schemes for the other higher diamondoids are similar.

The higher diamondoid families contain multiple isomers (including stereoisomers) and substituted or derivatized diamondoids will typically contain one or more chiral centers. Higher diamondoids larger than tetramantane exist in forms with more than one molecular weight. If desired, such compounds can be isolated as pure isomers or stereoisomers (e.g., as individual enantiomers or diastereomers, or as stereoisomer-enriched mixtures). Pure stereoisomers (or enriched mixtures) may be prepared using, for example, crystallization, optically active solvents or stereo-selective reagents well-known in the art. Alternatively, racemic mixtures of such compounds can be separated using, for example, chiral column chromatography, chiral resolving agents and the like.

Higher diamondoids can be recovered from readily available feedstocks using the following general methods and procedures. It will be appreciated that where typical or preferred process conditions (i.e., reaction temperatures, times, solvents, pressures, etc.) are given, other process conditions can also be used unless otherwise stated. Optimum reaction conditions may vary with feedstocks, but such conditions can be determined by one skilled in the art by routine optimization procedures.

A feedstock is selected such that it comprises recoverable amounts of higher diamondoid components. Preferred feedstocks include, for example, natural gas condensates, and refinery streams having high concentrations of diamondoids. With regard to the latter, such refinery streams include hydrocarbonaceous streams recoverable from cracking processes, distillations, coking and the like. Particularly preferred feedstocks include condensate feedstocks recovered from the Norphlet Formation in the Gulf of Mexico and from the LeDuc Formation in Canada.

Figure 3:
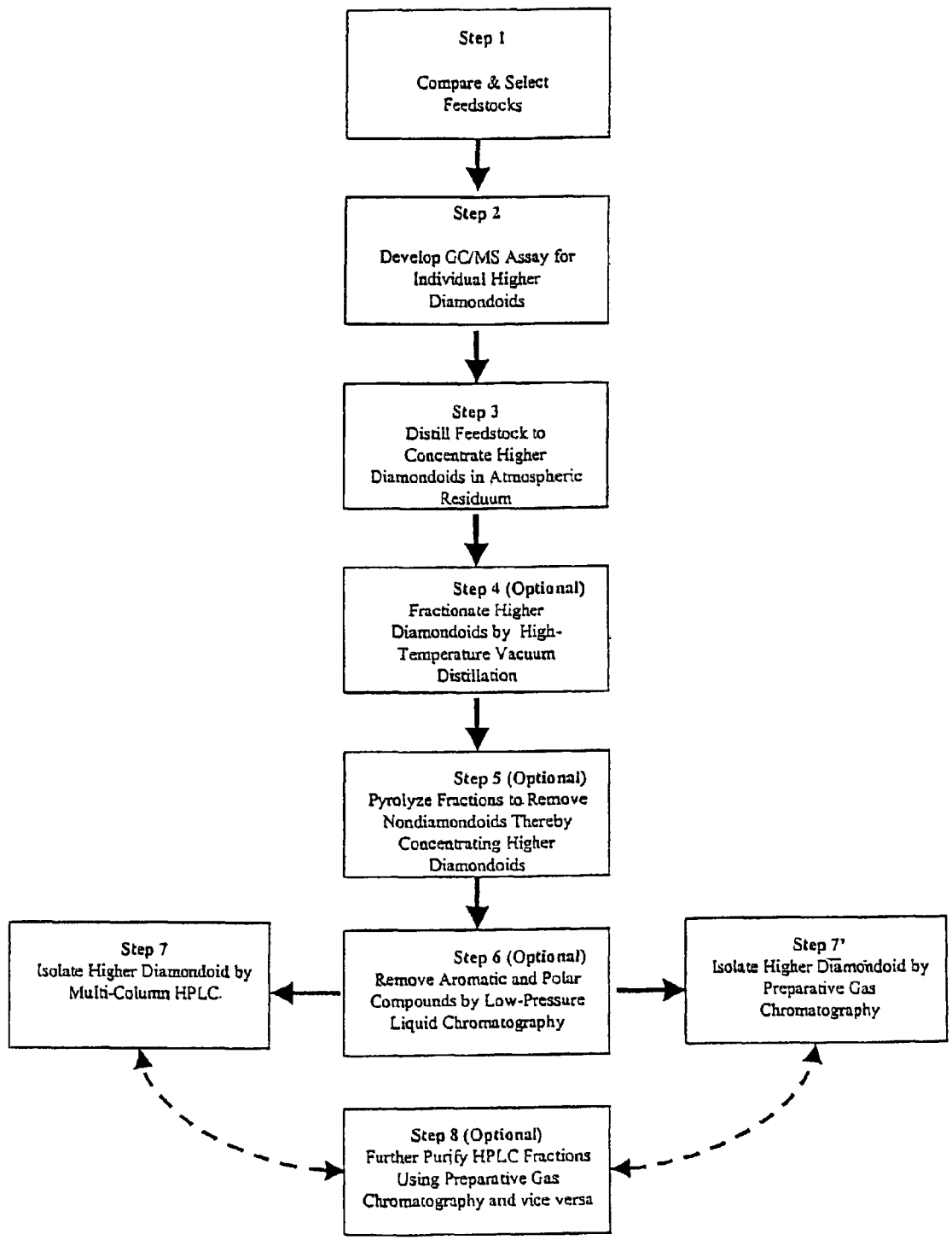
FIG. 3 is a flow chart representing the various steps used in the isolation of higher diamondoid-containing fractions and individual higher diamondoid components which may be functionalized. Note that the steps can in some cases be used in a different sequence and possibly skipped as discussed in the Examples.

The general isolation processes of higher diamondoids are shown in FIG. 3.

In one embodiment, the removal of contaminants includes distillation of the feedstock to remove non-diamondoid components as well as lower diamondoid components and in some cases other nonselected higher diamondoids having boiling points less than that of the lowest boiling point higher diamondoid component selected for recovery.

Such a distillation can be operated to fractionate the feedstocks and provide several cuts in a temperature range of interest to provide the initial enrichment of the selected higher diamondoids or groups of selected higher diamondoids. The cuts, which are enriched in one or more selected diamondoids or a particular diamondoid component of interest, are retained and may require further purification. The following Table illustrates representative fractionation points that may be used to enrich various higher diamondoids in overheads. In practice it may be advantageous to make wider temperature range cuts which would often contain groups of higher diamondoids which could be separated together in subsequent separation steps.

| | Fractionation Points | | | | | |
| --- | --- | --- | --- | --- | --- | --- |
| | Most Preferred | | Preferred | | Useful | |
| Higher Diamondoid | Lower Cut Temperature (° C.) | Higher Cut Temperature (° C.) | Lower Cut Temperature (° C.) | Higher Cut Temperature (° C.) | Lower Cut Temperature (° C.) | Higher Cut Temperature (° C.) |
| Tetramantanes | 349 | 382 | 330 | 400 | 300 | 430 |
| Pentamantanes | 385 | 427 | 360 | 450 | 330 | 490 |
| Cyclohexamantanes | 393 | 466 | 365 | 500 | 330 | 550 |
| Hexamantanes | 393 | 466 | 365 | 500 | 330 | 550 |
| Heptamantanes | 432 | 504 | 395 | 540 | 350 | 600 |
| Octamantanes | 454 | 527 | 420 | 560 | 375 | 610 |
| Nonamantanes | 463 | 549 | 425 | 590 | 380 | 650 |
| Decamantanes | 472 | 571 | 435 | 610 | 390 | 660 |
| Undecamantanes | 499 | 588 | 455 | 625 | 400 | 675 |

It shall be understood that substituted higher diamondoids may accordingly shift these preferred cut-point temperatures to higher temperatures due to the addition of substituent groups. Additional temperature refinements will allow for higher purity cuts for the diamondoid of interest.

Other processes for the removal of lower diamondoids, unselected higher diamondoids, if any, and/or hydrocarbonaceous non-diamondoid components include, by way of example only, size separation techniques, evaporation either under normal or reduced pressure, crystallization, chromatography, well head separators, reduced pressure and the like. Removal processes can utilize the larger sizes of the higher diamondoids to effect separation of lower diamondoids therefrom. For example, size separation techniques using membranes will allow a feedstock retained in the membrane to selectively pass lower diamondoids across the membrane barrier provided that the pore size of the membrane barrier is selected to differentiate between compounds having the size of higher diamondoid components as compared to lower diamondoid components. The pore size of molecular sieves such as zeolites and the like can also be used to effect size separation.

In a preferred embodiment, the removal process provides for a treated feedstock having a ratio of lower diamondoid components to higher diamondoid components of no greater than 9:1; more preferably, no greater than 2:1; and even more preferably, the ratio is no greater than 1:1. Even more preferably, after removal of the lower diamondoid component(s) from the feedstock, at least about 10%, more preferably at least 50% and still more preferably at least 90% of the higher diamondoid components are retained in the feedstock as compared to that amount found in the feedstock prior to the removal.

When recovery of hexamantane and higher diamondoid components is desired and when the feedstock contains non-diamondoid contaminants, the feedstock will also be generally subjected to pyrolysis to effect removal of at least a portion of the hydrocarbonaceous non-diamondoid components from the feedstock. The pyrolysis effectively concentrates the amount of higher diamondoids in the pyrolytically treated feedstock.

Pyrolysis is effected by heating the feedstock under vacuum conditions or in an inert atmosphere, at a temperature of at least about 390° C. and, preferably, from about 400 to about 550° C., more preferably from about 400 to about 450° C., and especially 410 to 430° C.; for a period of time to effect pyrolysis of at least a portion of the non-diamondoid components of the feedstock. As described in U.S. Ser. No. 60/396, 991 filed Jul. 18, 2002, incorporated herein by reference, the pyrolysis can also be carried out in the presence of a hydrocracking and/or hydrotreating catalyst in the presence of added hydrogen. The specific conditions employed are selected such that recoverable amounts of selected higher diamondoid components are retained in the feedstock. The selection of such conditions is well within the skill of the art.

Preferably, pyrolysis is continued for a sufficient period and at a sufficiently high temperature to thermally degrade at least about 10% of the non-diamondoid components (more preferably at least about 50% and even more preferably at least about 90%) from the pyrolytically treated feedstock based on the total weight of the non-diamondoid components in the feedstock prior to pyrolysis.

It is also preferred to further purify the recovered feedstock using one or more purification techniques such as chromatography, crystallization, thermal diffusion techniques, zone refining, progressive recrystalization, size separation and the like. In a particularly preferred process, the recovered feedstock is first subjected to gravity column chromatography using silver nitrate impregnated silica gel followed by HPLC using two different columns of differing selectivities to isolate the selected diamondoids and crystallization to provide crystals of the highly concentrated target higher diamondoids.

FIG. 4A is a table of relative retention times for the various higher diamondoids in a gas chromatography system while FIG. 4B is a table of HPLC elution times for the higher diamondoids.

Derivatization of Higher Diamondoids

There are three different carbons in the higher diamondoids skeleton: quaternary (4° or C-4), tertiary (3° or C-3), and secondary (2° or C-2) carbons. Of those different carbons, quaternary carbons are impossible to perform any kind of reactions on. Chemical reactions can only take place on those tertiary (3° or C-3) and secondary (2° or C-2) carbons in the higher diamondoid skeletons. It should be mentioned that some of the tertiary or secondary carbons are equivalent. This means that the derivatives substituted at those equivalent tertiary or secondary carbons are identical.

Figure 6:
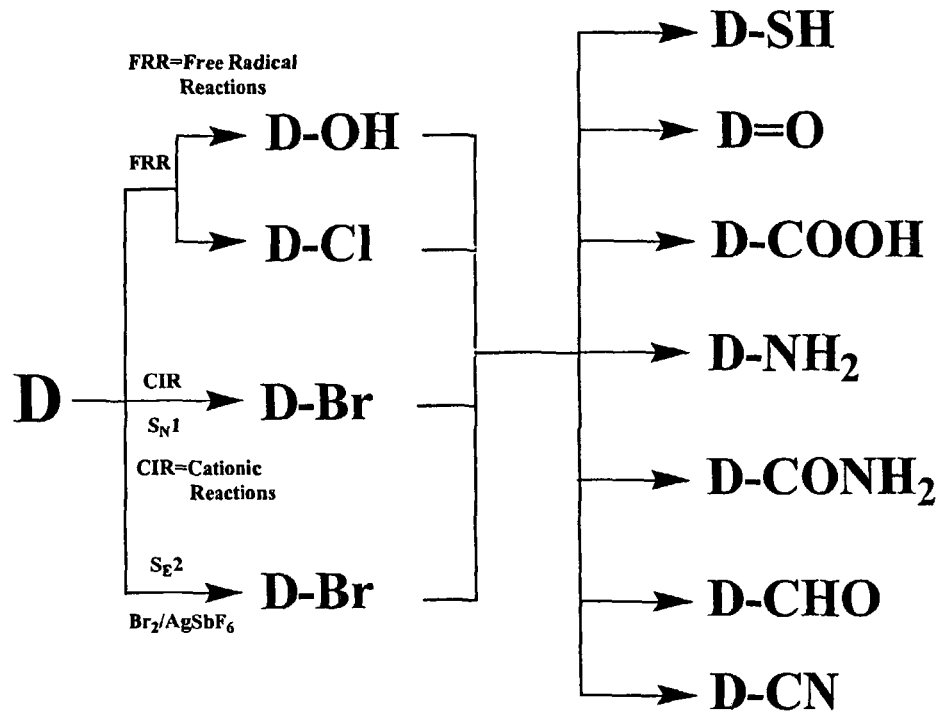
FIG. 6 shows three major reactions sorted by mechanism for the formation of primary functionalized higher diamondoids and some representative secondary functionalized materials which can be prepared from them.

FIG. 5 shows a flow chart for the strategy of derivatization of higher diamondoids and FIG. 6 shows some representative primary derivatives of higher diamondoids and the corresponding reactions. As shown in FIG. 6, there are, in general, three major reactions for the derivatization of higher diamondoids sorted by mechanism: nucleophilic ($S_N1$-type) and electrophilic ($S_E2$-type) substitution reactions, and free radical reaction (details for such reactions and their use with adamantane are shown, for instance in, "*Recent developments in the adamantane and related polycyclic hydrocarbons*" by R. C. Bingham and P. v. R. Schleryer as a chapter of the book entitled "*Chemistry of Adamantanes*", Springer-Verlag, Berlin Heidelberg New York, 1971 and in; "*Reactions of adamantanes in electrophilic media*" by I. K. Moiseev, N. V. Makarova, M. N. Zemtsova published in *Russian Chemical Review*, 68(12), 1001-1020 (1999); "*Cage hydrocarbons*" edited by George A. Olah, John Wiley & Son, Inc., New York, 1990).

Figure 7:
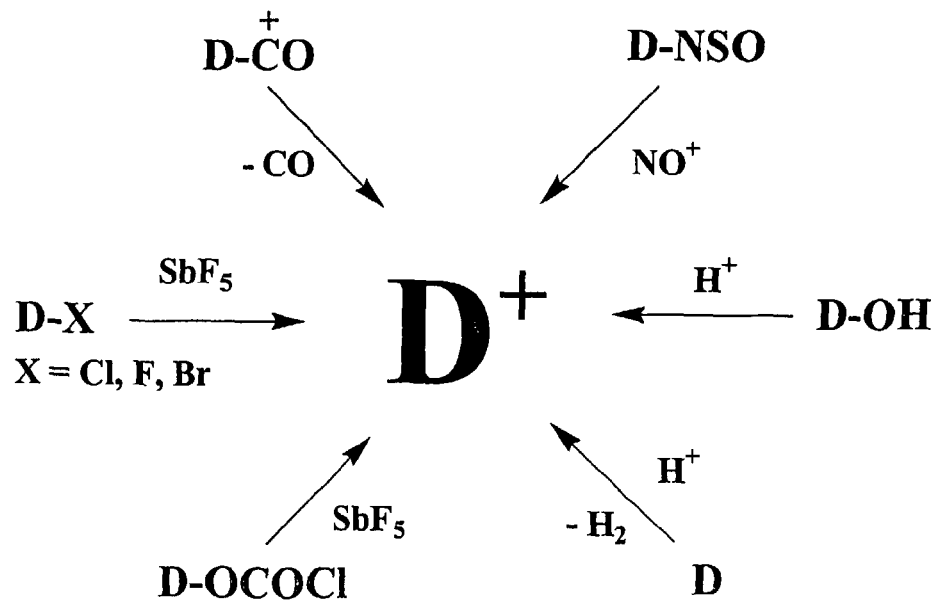
FIG. 7 shows representative pathways by which higher diamondoid carbocations are generated, wherein D is a higher diamondoid nucleus.
Figure 8:
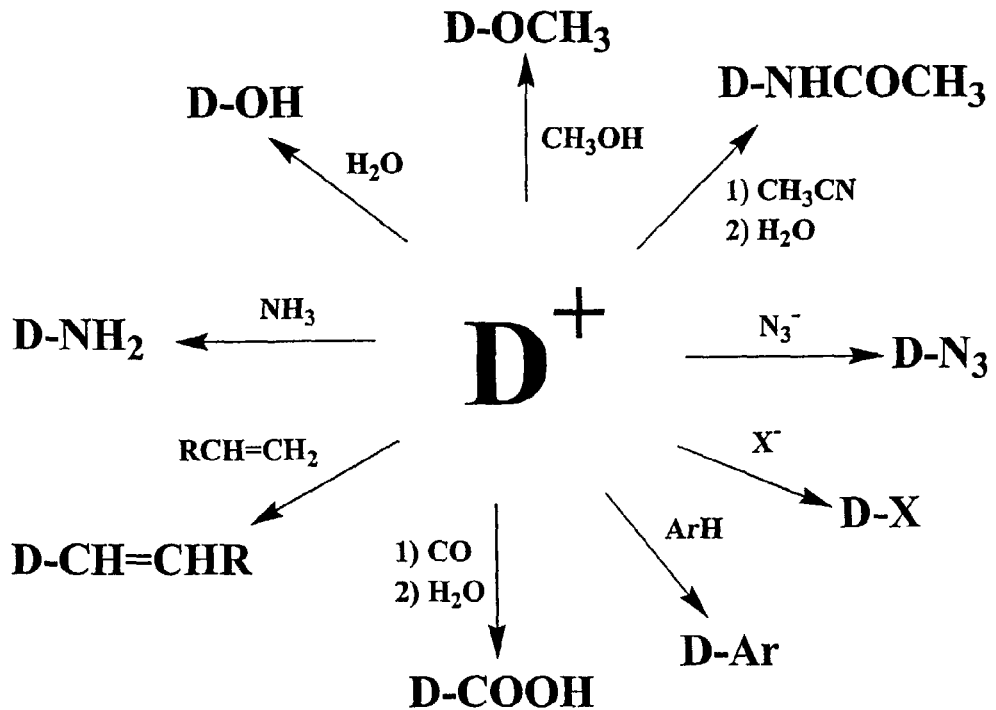
FIG. 8 shows representative pathways by which higher diamondoids are functionalized via higher diamondoid carbocations ($S_N1$ reactions), wherein D is a higher diamondoid nucleus.

$S_N1$ reactions involve the generation of higher diamondoid carbocations (there are several different ways to generate the higher diamondoid carbocations, for instance, the carbocation is generated from a parent higher diamondoid, a hydroxylated higher diamondoid or a halogenated higher diamondoid, shown in FIG. 7), which subsequently react with various nucleophiles. Some representative examples are shown in FIG. 8. Such nucleophiles include, for instance, the following: water (providing hydroxylated higher diamondoids); halide ions (providing halogenated higher diamondoids); ammonia (providing aminated higher diamondoids); azide (providing azidylated higher diamondoids); nitriles (the Ritter reaction, providing aminated higher diamondoids after hydrolysis); carbon monoxide (the Koch-Haaf reaction, providing carboxylated higher diamondoids after hydrolysis); olefins (providing alkenylated higher diamondoids after deprotonation); and aromatic reagents (providing arylated higher diamondoids after deprotonation). The reaction occurs similarly to those of open chain alkyl systems, such as t-butyl, t-cumyl and cycloalkyl systems. Since tertiary (bridgehead) carbons of higher diamondoids are considerably more reactive than secondary carbons under $S_N1$ reaction conditions, substitution at the tertiary carbons is favored.

Figure 9:
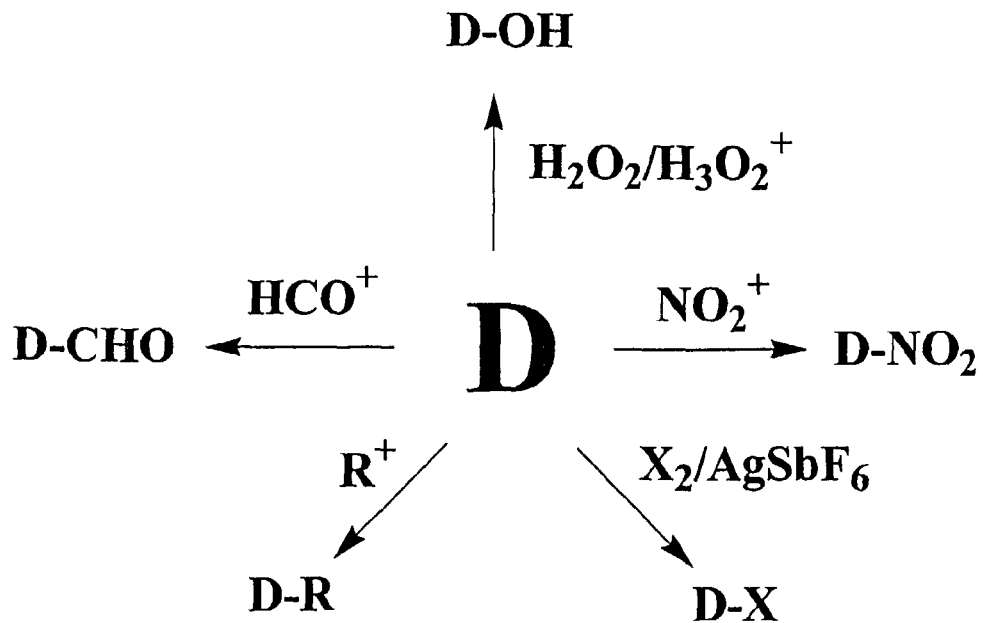
FIG. 9 shows representative pathways by which higher diamondoids are functionalized via electrophilic substitution reactions ($S_E2$ reactions), wherein D is a higher diamondoid nucleus.

$S_E2$-type reactions (i.e., electrophile substitution of a C—H bond via a five-coordinate carbocation intermediate) include, for instance, the following reactions: hydrogen-deuterium exchange upon treatment with deuterated superacids (e.g., DF—SbF$_5$ or DSO$_3$F—SbF$_5$); nitration upon treatment with nitronium salts, such as NO$_2^+$BF$_4^-$ or NO$_2^+$PF$_6^-$ in the presence of superacids (e.g., CF$_3$SO$_3$H); halogenation upon, for instance, reaction with Cl$_2$+AgSbF$_6$; alkylation of the bridgehead carbons under the Friedel-Crafts conditions (i.e., S$_E$2-type σ alkylation); carboxylation under the Koch reaction conditions; and, oxygenation under S$_E$2-type σ hydroxylation conditions (e.g., hydrogen peroxide or ozone using superacid catalysis involving H$_3$O$_2^+$ or HO$_3^+$, respectively). Some representative S$_E$2-type reactions are shown in FIG. 9.

Of those S$_N$1 and S$_E$2 reactions, S$_N$1-type reactions are the most frequently used for the derivatization of higher diamondoids. However, such reactions produce the derivatives mainly substituted at the tertiary carbons. Substitution at the secondary carbons of higher diamondoids is not easy in carbonium ion processes since secondary carbons are considerably less reactive than the bridgehead positions (tertiary carbons) in ionic processes. However, reactions at the secondary carbons are achieved by taking advantage of the low selectivity of free radical reactions and the high ratios of 2° (secondary) to 3° (tertiary, bridgehead) hydrogens in higher diamondoids. Thus, free radical reactions provide a method for the preparation of a greater number of the possible isomers of a given higher diamondoid than might be available by ionic precesses. The complex product mixtures and/or isomers which result, however, are generally difficult to separate. Due to the decreased symmetry of substituted higher diamondoids, free radical substitution of these substrates may give rise to very complex product mixtures. Therefore, in most cases, practical and useful free radical substitutions of higher diamondoids can use photochlorination and/or photooxidation under special circumstances which permit a simpler separation of the product mixture. For instance, photochlorination is particularly useful for the synthesis of chlorinated higher diamondoids at the secondary carbons and further derivatizations at the secondary carbons because chlorinated higher diamondoids at the secondary carbons are similar in reactivity to those derivatized at the tertiary carbons.

Photooxidation is another powerful free radical reaction for the synthesis of hydroxylated derivatives at the secondary carbons which are further oxidized to keto derivatives, which can be reduced to alcohols providing unique hydroxylated higher diamondoid derivatives at the secondary carbons.

Considering this significant advantage of separating the keto higher diamondoids, a variety of higher diamondoid derivatives at the secondary carbons are prepared starting from the keto derivatives (higher diamondoidones), such as by reducing the keto group by, for instance, LiAlH$_4$, to provide the corresponding hydroxylated derivatives at the secondary carbons and further derivatizations at the secondary carbons starting from those hydroxylated derivatives. Higher diamondoidones can also undergo acid-catalyzed (HCl-catalyzed) condensation reaction with, for example, excess phenol or aniline in the presence of hydrogen chloride to form 2,2-bis(4-hydroxyphenyl) higher diamondoids or 2,2-bis(4-aminophenyl) higher diamandoids substituted at the secondary carbons. With the development of separation technology, such as by using up-to-date HPLC technique, we may predict that more free radical reactions might be employed for the synthesis of derivatives of higher diamondoids.

Using those three major types of reactions for the derivatization of higher diamondoids, a number of higher diamondoid derivatives are prepared. Representative core reactions and the derivatives are presented as following as either very important means to activate the higher diamondoid nuclei or very important precursors for further derivatizations.

Figure 10:
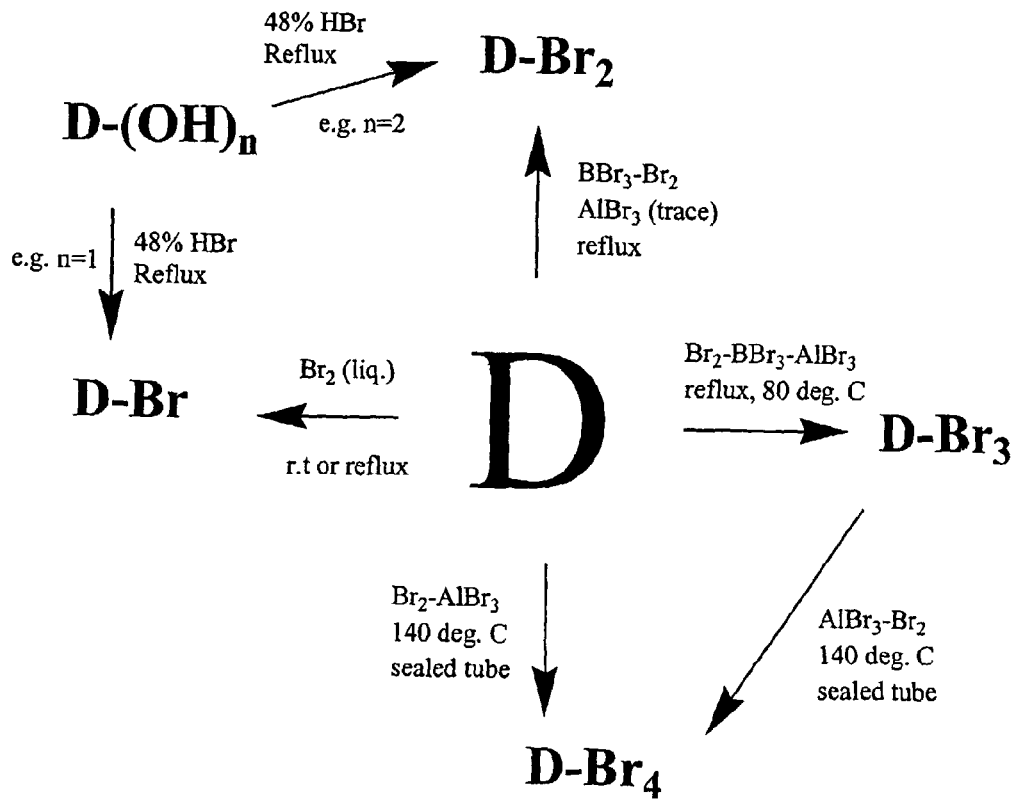
FIG. 10 shows representative pathways by which brominated higher diamondoids are prepared, wherein D is a higher diamondoid nucleus.

FIG. 10 shows some representative pathways for the preparation of brominated higher diamondoid derivatives. Mono- and multi-brominated higher diamondoids are some of the most versatile intermediates in the derivative chemistry of higher diamondoids. These intermediates are used in, for example, the Koch-Haaf, the Ritter, and the Friedel-Crafts alkylation/arylation reactions. Brominated higher diamondoids are prepared by two different general routes. One involves direct bromination of higher diamondoids with elemental bromine in the presence or absence of a Lewis acid (e.g. BBr$_3$—AlBr$_3$) catalyst. The other involves the substitution reaction of hydroxylated higher diamondoids with hydrobromic acid.

Direct bromination of higher diamondoids is highly selective resulting in substitution at the bridgehead (tertiary) carbons. By proper choice of catalyst and conditions, one, two, three, four, or more bromines can be introduced sequentially into the molecule, all at bridgehead positions. Without a catalyst, the mono-bromo derivative is the major product with minor amounts of higher bromination products being formed. By use of suitable catalysts, however, di-, tri-, and tetra-, penta-, and higher bromide derivatives of higher diamondoids are isolated as major products in the bromination (e.g., adding catalyst mixture of boron bromide and aluminum bromide with different molar ratios into the bromine reaction mixture). Typically, tetrabromo or higher bromo derivatives are synthesized at higher temperatures in a sealed tube.

To prepare bromo derivatives substituted at secondary carbons, for example, the corresponding hydroxylated higher diamondoids at the secondary carbons is treated under mild conditions with hydrobromic acid. Preferably, higher diamondoids hydroxylated at secondary carbons are prepared by the reduction of the corresponding keto derivative as described above.

Bromination reactions of higher diamondoids are usually worked up by pouring the reaction mixture onto ice or ice water and adding a suitable amount of chloroform or ethyl ether or carbon tetrachloride to the ice mixture. Excess bromine is removed by distillation under vacuum and addition of solid sodium disulfide or sodium hydrogen sulfide. The organic layer is separated and the aqueous layer is extracted by chloroform or ethyl ether or carbon tetrachloride for an additional 2-3 times. The organic layers are then combined and washed with aqueous sodium hydrogen carbonate and water, and finally dried.

To isolate the brominated derivatives, the solvent is removed under vacuum. Typically, the reaction mixture is purified by subjecting it to column chromatography on either alumina or silica gel using standard elution conditions (e.g., eluting with light petroleum ether, n-hexane, or cyclohexane or their mixtures with ethyl ether). Separation by preparative gas chromatography (GC) or high performance liquid chromatography (HPLC) is used where normal column chromatography is difficult and/or the reaction is performed on extremely small quantities of material.

Figure 11:
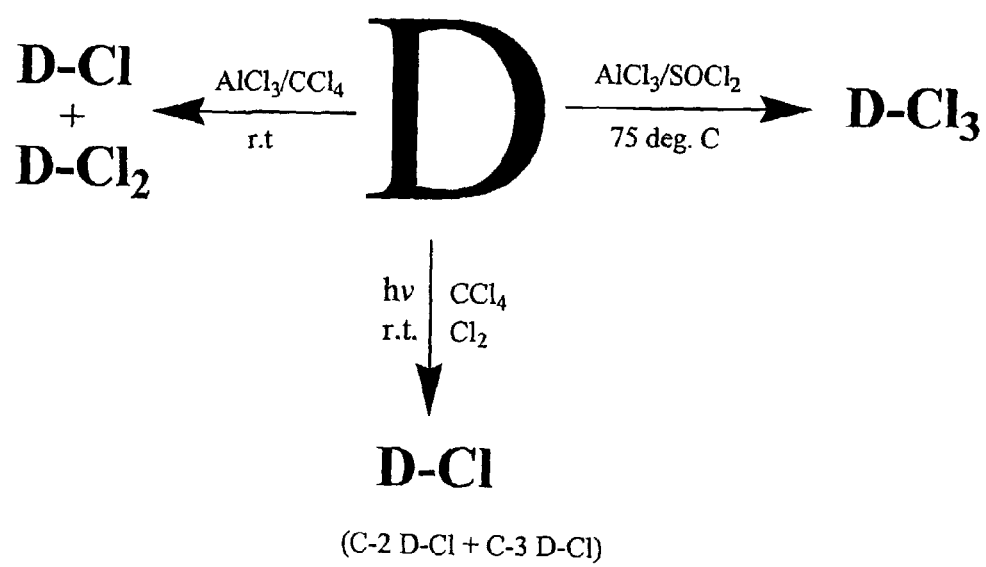
FIG. 11 shows representative pathways by which chlorinated higher diamondoids are prepared, wherein D is a higher diamondoid nucleus.

Similarly to bromination reactions, higher diamondoids are chlorinated or photochlorinated to provide a variety of mono-, di-, tri-, or even higher chlorinated derivatives of the higher diamondoids. FIG. 11 shows some representative pathways for the synthesis of chlorinated higher diamondoid derivatives, especially those chlorinated derivatives at the secondary carbons by way of photochlorination.

Figure 12:
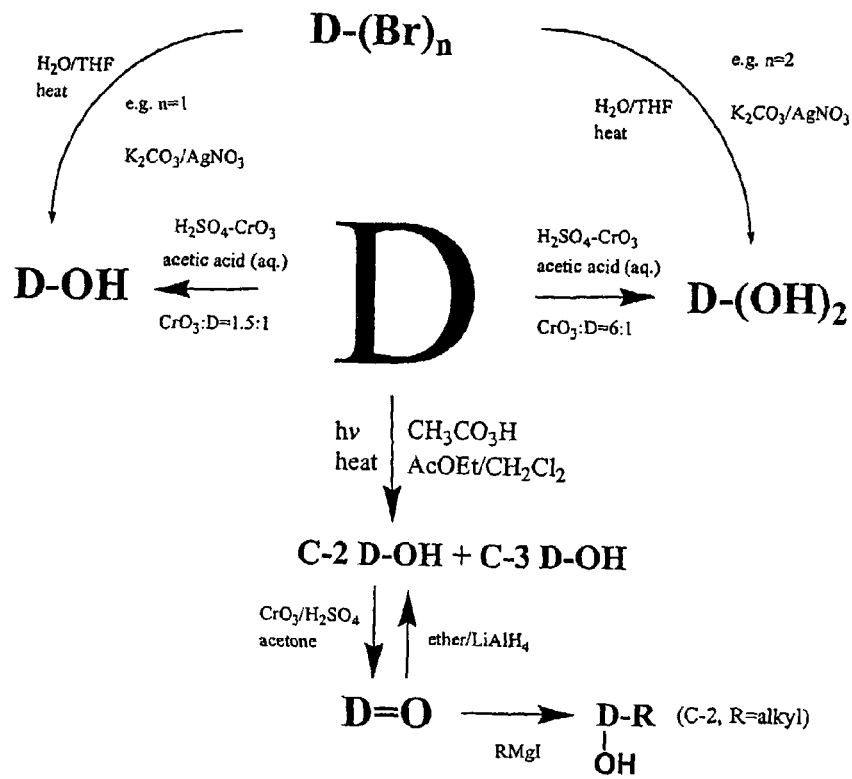
FIG. 12 shows representative pathways by which hydroxylated and keto higher diamondoids are prepared, wherein D is a higher diamondoid nucleus.

FIG. 12 shows some representative pathways for the synthesis of hydroxylated higher diamondoids. Direct hydroxylation is also effected on higher diamondoids upon treatment with N-hydroxyphthalimide and a binary co-catalyst in acetic acid. Hydroxylation is a very important way of activating the higher diamondoid nuclei for further derivatizations, such as the generation of higher diamondoid carbocations under acidic conditions, which undergo the $S_N1$ reaction to provide a variety of higher diamondoid derivatives. In addition, hydroxylated derivatives are very important nucleophilic agents, by which a variety of higher diamondoid derivatives are produced. For instance, the hydroxylated derivatives are esterified under standard conditions such as reaction with an activated acid derivative. Alkylation to prepare ethers is performed on the hydroxylated derivatives through nucleophilic substitution on appropriate alkyl halides.

The above described three core derivatives (hydroxylated higher diamondoids and halogenated especially brominated and chlorinated higher diamondoids), in addition to the parent higher diamondoids or substituted higher diamondoids directly separated from the feedstocks as described above, are most frequently used for further derivatizations of higher diamondoids, such as hydroxylated and halogenated derivatives at the tertiary carbons are very important precursors for the generation of higher diamondiod carbocations, which undergo the $S_N1$ reaction to provide a variety of higher diamondoid derivatives thanks to the tertiary nature of the bromide or chloride or alcohol and the absence of skeletal rearrangements in the subsequent reactions. Examples are given below.

Figure 13:
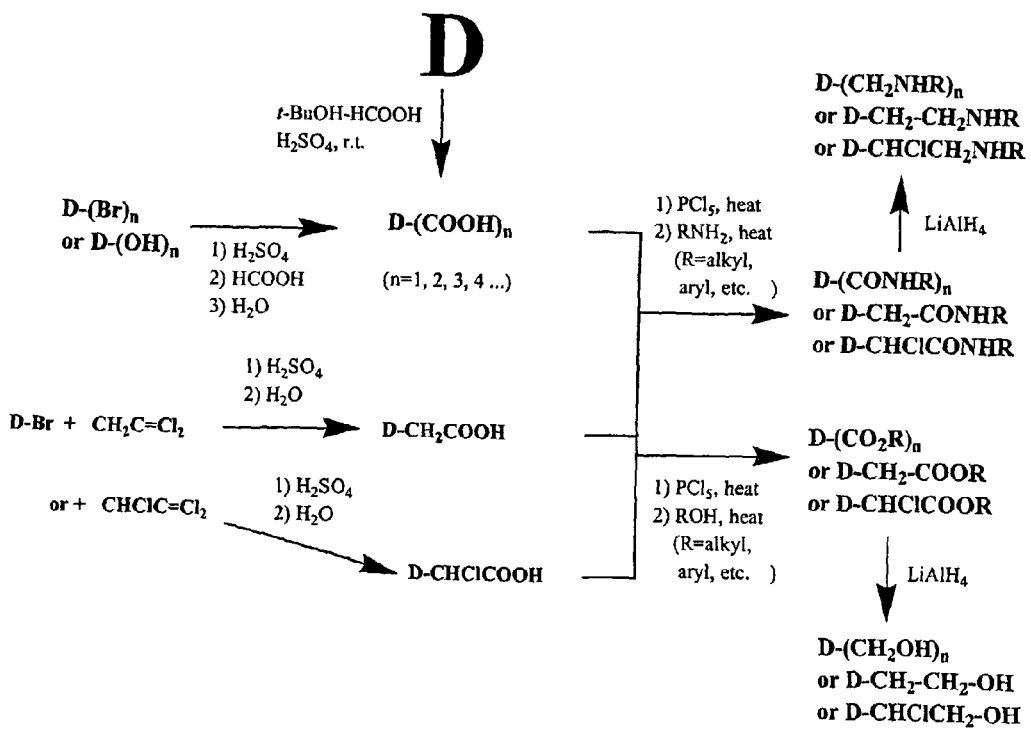
FIG. 13 shows representative pathways by which carboxylated, esterified, and carboxamide higher diamondoids are prepared together with the subsequent reactions and derivatives thereof, wherein D is a higher diamondoid nucleus.

FIG. 13 shows some representative pathways for the synthesis of carboxylated higher diamondoids, such as the Koch-Haaf reaction, starting from hydroxylated or brominated higher diamondoids. It should be mentioned that for most cases, using hydroxylated precursors get better yields than using brominated higher diamondoids. For instance, carboxylated derivatives are obtained from the reaction of hydroxylated derivatives with formic acid after hydrolysis. The carboxylated derivatives are further esterified through activation (e.g., conversion to acid chloride) and subsequent exposure to an appropriate alcohol. Those esters are reduced to provide the corresponding hydroxymethyl higher diamondoids (higher diamondoid substituted methyl alcohols, D—$CH_2OH$). Amide formation is also performed through activation of the carboxylated derivative and reaction with a suitable amine. Reduction of the higher diamondoid carboxamide with reducing agents (e.g. lithium aluminum hydride) provides the corresponding aminomethyl higher diamondoids (higher diamondoid substituted methylamines, D—$CH_2NH_2$).

Figure 14:
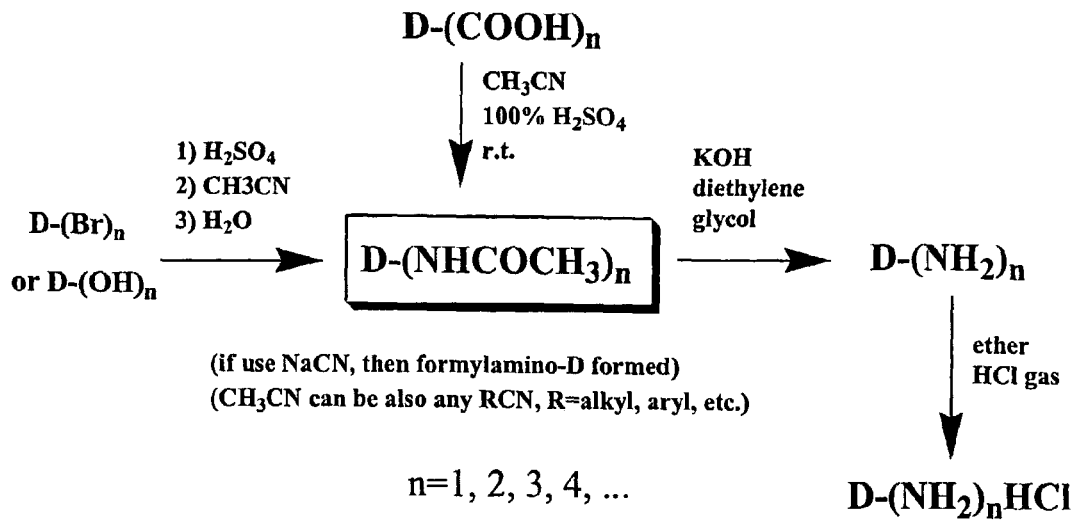
FIG. 14 shows representative pathways by which acetaminated and aminated higher diamondoids and the amine hydrogen chloride salts are prepared, wherein D is a higher diamondoid nucleus.
Figure 15:
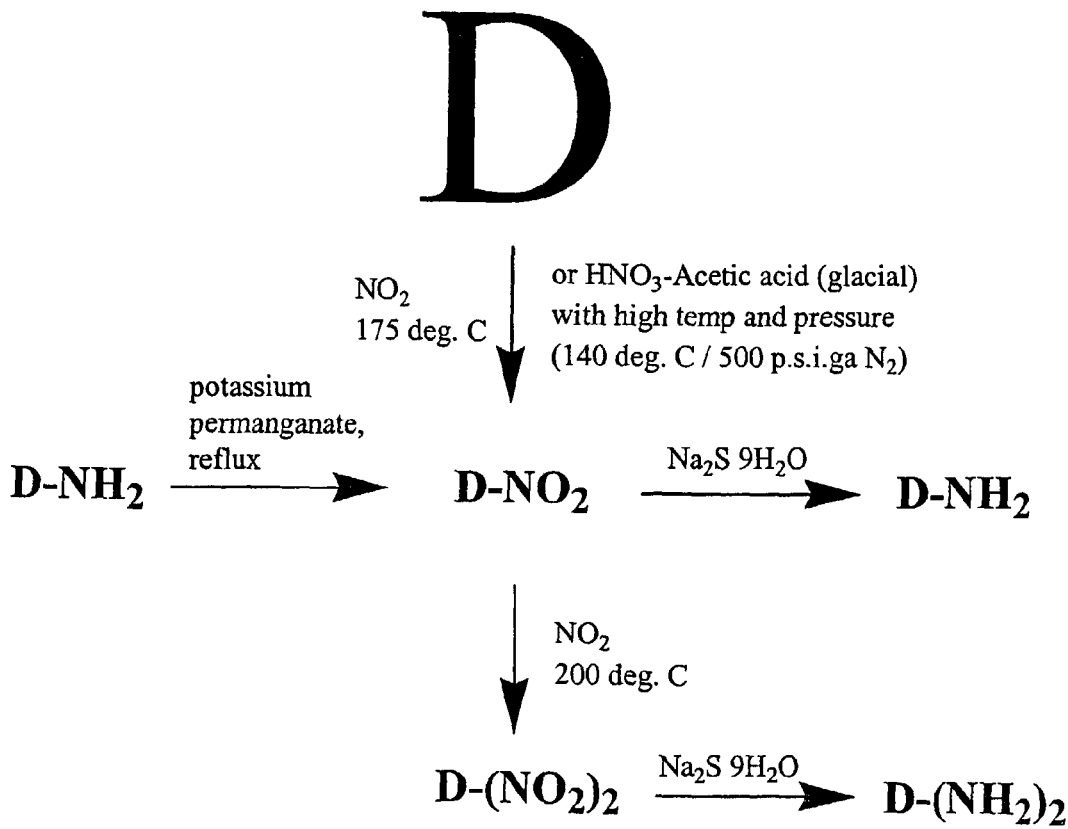
FIG. 15 shows representative pathways by which nitro higher diamondoids are prepared and their conversion to aminated higher diamondoids, wherein D is a higher diamondoid nucleus.

FIG. 14 shows some representative pathways for the synthesis of acylaminated higher diamondoids, such as the Ritter reaction starting from hydroxylated or brominated higher diamondoids. Similarly to the Koch-Haaf reaction, using hydroxylated precursors get better yields than using brominated higher diamondoids in most cases. Acylaminated higher diamondoids are converted to amino derivatives after alkaline hydrolysis. Amino higher diamondoids are further converted to, without purification in most cases, amino higher diamondoid hydrochloride by introducing hydrochloride gas into the aminated derivatives solution. Amino higher diamondoids are some of very important precursors in the synthesis of medicines. They are also prepared from the reduction of nitrated compounds. FIG. 15 shows some representative pathways for the synthesis of nitro higher diamondoid derivatives. Higher diamondoids are nitrated by concentrated nitric acid in the presence of glacial acetic acid under high temperature and pressure. The nitrated higher diamondoids are reduced to provide the corresponding amino derivatives. In turn, for some cases, amino higher diamondoids are oxidized to the corresponding nitro derivatives if necessary. The amino derivatives are also synthesized from the brominated derivatives by heating them in the presence of formamide and subsequently hydrolyzing the resultant amide.

Similarly to the hydroxylated compounds, amino higher diamonds are acylated or alkylated. For instance, reaction of an amino higher diamondoid with an activated acid derivative produces the corresponding amide. Alkylation is typically performed by reacting the amine with a suitable carbonyl containing compound in the presence of a reducing agent (e.g. lithium aluminum hydride). The amino higher diamondoids undergo condensation reactions with carbamates such as appropriately substituted ethyl N-arylsulfonylcarbamates in hot toluene to provide, for instance, N-arylsulfonyl-N'-higher diamondoidylureas.

Figure 16:
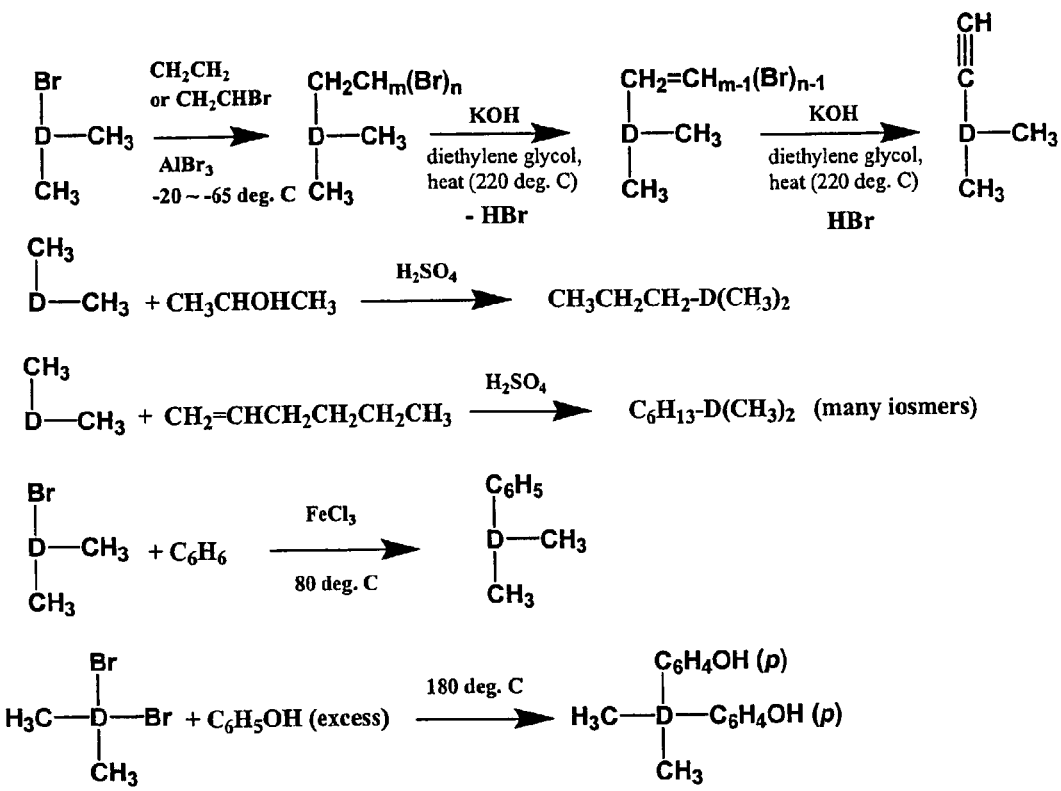
FIG. 16 shows representative pathways by which alkylated, alkenylated, alkynylated, and arylated higher diamondoids are prepared, wherein D is a higher diamondoid nucleus.

FIG. 16 presents some representative pathways for the synthesis of alkylated, alkenylated, alkynylated and arylated higher diamondoids, such as the Friedel-Crafts reaction. Ethenylated higher diamondoid derivatives are synthesized by reacting a brominated higher diamondoid with ethylene in the presence of $AlBr_3$ followed by dehydrogen bromide with potassium hydroxide (or the like). The ethenylated compound is transformed into the corresponding epoxide under standard reaction conditions (e.g., 3-chloroperbenzoic acid). Oxidative cleavage (e.g., ozonolysis) of the ethenylated higher diamondoid affords the related aldehyde. The ethynylated higher diamondoid derivatives are obtained by treating a brominated higher diamondoid with vinyl bromide in the presence of $AlBr_3$. The resultant product is dehydrogen bromide using KOH or potassium t-butoxide to provide the desired compound.

More reactions are illustrative of methods which can be used to functionalize higher diamondoids. For instance, fluorination of a higher diamondoid is carried out by reacting the higher diamondoid with a mixture of poly(hydrogen fluoride) and pyridine (30% Py, 70% HF) in the presence of nitronium tetrafluoroborate. Sulfur tetrafluoride reacts with a higher diamondoid in the presence of sulfur monochloride to afford a mixture of mono-, di-, tri- and even higher fluorinated higher diamondoids. Iodo higher diamondoids are obtained by a substitutive iodination of chloro, bromo or hydroxyl higher diamondoids.

Reaction of the brominated derivatives with hydrochloric acid in dimethylformamide (DMF) converts the compounds to the corresponding hydroxylated derivatives. Brominated or iodinated higher diamondoids are converted to thiolated higher diamondoids by way of, for instance, reacting with thioacetic acid to form higher diamondoid thioacetates followed by removal of the acetate group under basic conditions. Brominated higher diamondoids, e.g. D—Br, is heated under reflux with an excess (10 fold) of hydroxyalkylamine, e.g. HO—$CH_2CH_2$—$NH_2$, in the presence of a base, e.g. triethylamine, higher diamondoidyloxyalkylamine, e.g. D—O—$CH_2CH_2$—$NH_2$, is obtained. On acetylation of the amines with acetic anhydride and pyridine, a variety of N-acetyl derivatives are obtained. Direct substitution reaction of brominated higher diamondoids, e.g. D—Br, with sodium azide in dipolar aprotic solvents, e.g. DMF, to afford the azido higher diamondoids, e.g. D—$N_3$.

Figure 17:
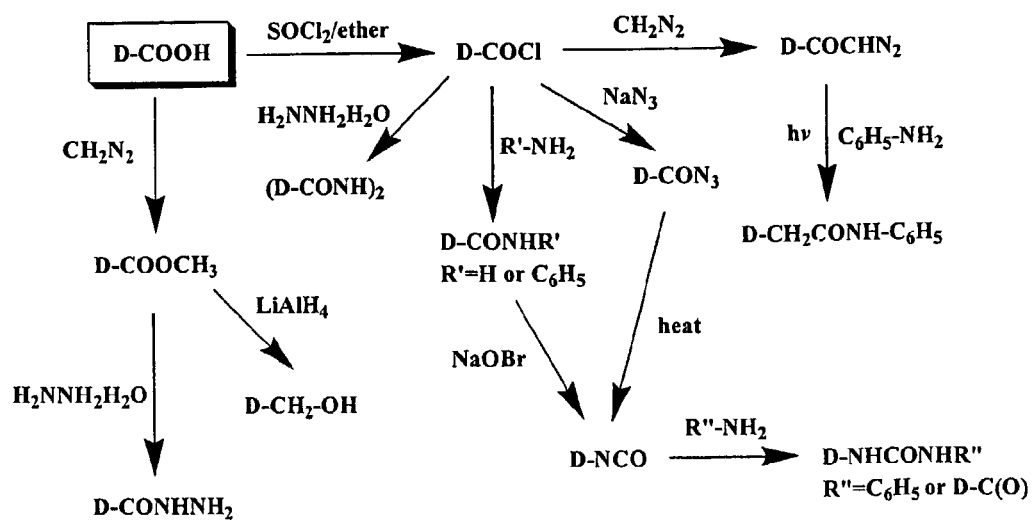
FIG. 17 shows representative reactions starting from D—COOH and the corresponding derivatives which are formed, wherein D is a higher diamondoid nucleus.

Higher diamondoid carboxylic acid hydrazides are prepared by conversion of higher diamondoid carboxylic acid into a chloroanhydride by thionyl chloride and condensation with isonicotinic or nicotinic acid hydrazide (FIG. 17).

Higher diamondoidones or "higher diamondoid oxides" are synthesized by photooxidation of higher diamondoids in the presence of peracetic acid followed by treatment with a mixture of chromic acid-sulfuric acid. Higher diamondoidones are reduced by, for instance, $LiAlH_4$, to higher diamondoidols hydroxylated at the secondary carbons. Higher diamondoidones also undergo acid-catalyzed (HCl-catalyzed) condensation reaction with, for example, excess phenol or aniline in the presence of hydrogen chloride to form 2,2-bis (4-hydroxyphenyl) higher diamondoids or 2,2-bis(4-aminophenyl) higher diamondoids.

Higher diamondoidones (e.g. D=O) are treated with RCN (R=hydrogen, alkyl, aryl, etc.) and reduced with $LiAlH_4$ to give the corresponding C-2-aminomethyl-C-2-D—OH, which are heated with $COCl_2$ or $CSCl_2$ in toluene to afford the following derivatives shown in formula IV (where Z=O or S):

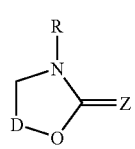

IV

Higher diamondoidones react with a suitable primary amine in an appropriate solvent to form the corresponding imines. Hydrogenation of the imines in ethanol using Pd/C as the catalyst at about 50° C. to afford the corresponding secondary amines. Methylation of the secondary amines following general procedures (see, for instance, H. W. Geluk and V. G. Keiser, *Organic Synthesis,* 53:8 (1973)) to give the corresponding tertiary amines. Quaternization of the tertiary amines by, for instance, slowly dropping $CH_3I$ (excess) into an ethanol solution of the amine at around 35° C. to form the corresponding quaternary amines.

C-2 derivatives of higher diamondoids, C-2 D—R' (R'=alkyl, alkoxy, halo, OH, Ph, COOH, $CH_2COOH$, $NHCOCH_3$, $CF_3COOH$) are prepared by nucleophilic substitution of higher diamondoid-C-2-spiro-C-3-diazirine in solution at 0-80° C. in the presence of an acid catalyst.

N-sulfinyl higher diamondoids $[D—(NSO)_n$, n=1, 2, 3, 4, . . . ] are prepared by refluxing the higher diamondoid-HCl with $SOCl_2$ in benzene for about half an hour to several hours afording mono-, di, tri-, or higher N-sulfinyl higher diamondoid derivatives.

Treatment of D—Br and/or D—Cl with $HCONH_2$ (wt. ratio not >1:2) at <195° C. followed by hydrolysis of the formylamino higher diamondoids D—NHCHO with <20% HCl at <110° C. affords the amino higher diamondoid hydrochloride D—$NH_2$HCl.

Higher diamondoid dicarboxamides are prepared by the reaction of higher diamondoid dicarbonyl chloride or higher diamondoid diacetyl chloride with aminoalkylamines. For instance, D—$(COCl)_2$ [from $SOCl_2$ and the corresponding dicarboxylic acid D—$(COOH)_2$] are treated with $(CH_3)_2NCH_2CH_2CH_2NH_2$ in $C_5H_5N$—$C_6H_6$ to give N,N'-bis(dimethylaminopropyl) higher diamondoid dicarboxamide.

Aminoethoxyacetylamino higher diamondoids are prepared from chloroacetylamino higher diamondoids and $HOCH_2CH_2NR'R''$. Thus, for instance, amino higher diamondoids, D—$NH_2$, and $ClCH_2COCl$ in benzene, is added to $(CH_3)_2NCH_2CH_2ONa$ in xylene and refluxed for about 10 hours to give aminoethoxyacetylamino higher diamondoids ($R'=R''=CH_3$).

Ritter reaction of C-3 D—OH and HCN gives D—$NH_2$; the preparation of D—NHCHO from higher diamondoids and HCN; the reaction of higher diamondoids with nitriles gives D—NHCHO and D—$NH_2$; the preparation of aza higher diamondoids from nitriles and compounds containing unsaturated OH groups, and SH groups, and so on.

Hydroxylated higher diamondoids, e.g. D—OH, react with $COCl_2$ or $CSCl_2$ to afford the higher diamondoidyloxycarbonyl derivatives, e.g. D—O—C(O)Cl or D—O—C(S)Cl the former being an important blocking group in biochemical syntheses.

Figure 18:
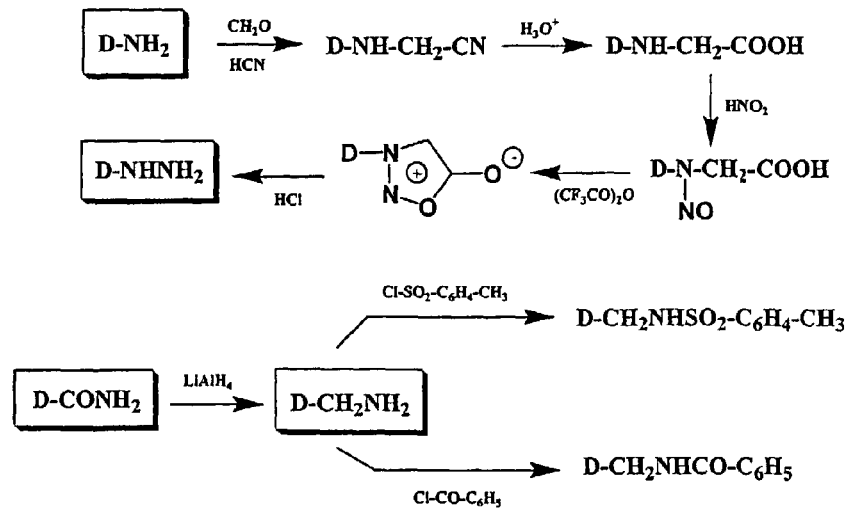
FIG. 18 shows representative reactions starting from D—$NH_2$ and D—$CONH_2$ and the corresponding derivatives, wherein D is a higher diamondoid nucleus.

FIG. 18 shows representative reactions starting from D—$NH_2$ and D—$CONH_2$ and the corresponding derivatives, wherein D is a higher diamondoid nucleus.

Figure 19:
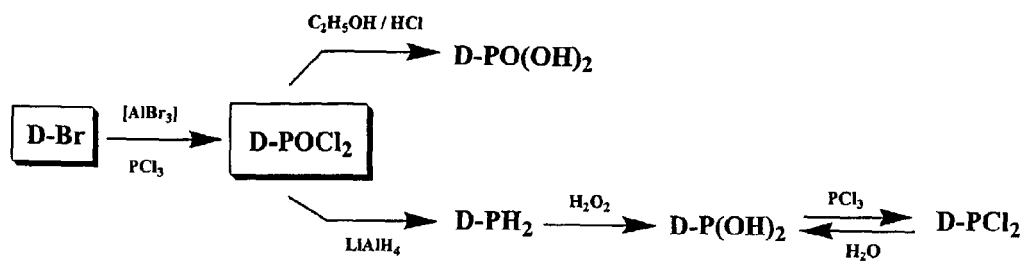
FIG. 19 shows representative reactions starting from D—$POCl_2$ and the corresponding derivatives, wherein D is a higher diamondoid nucleus.

FIG. 19 shows representative reactions starting from D—$POCl_2$ and the corresponding derivatives, wherein D is a higher diamondoid nucleus.

Figure 20:
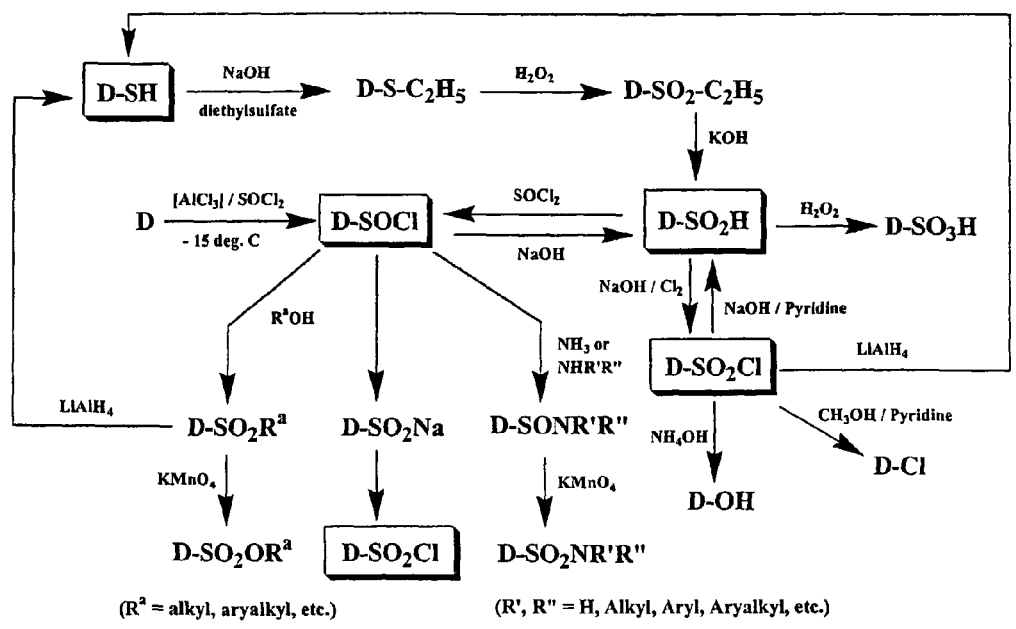
FIG. 20 shows representative reactions starting from D—SH or D—SOCl and the corresponding derivatives, wherein D is a higher diamondoid nucleus.

FIG. 20 shows representative reactions starting from D—SH or D—SOCl and the corresponding derivatives, wherein D is a higher diamondoid nucleus.

Illustrative Embodiments

As set forth above this invention is directed to functionalized higher diamondoids having at least one functional group. Preferably these derivatives have the structure of Formula I above.

The following table (Tabe 1) provides a representative list of higher diamondoid derivatives that are proposed to synthesize for either intermediates for medicine synthesis or medicines for pharmaceutical use.

TABLE 1

Representative higher diamondoid derivatives

| HIGHER DIAMONDOID | SUBSTITUENT OR DERIVATIVE |
|---|---|
| tetramantane - undecamantane | —$CH_2Br$ |
| tetramantane - undecamantane | —CH=CHBr |
| tetramantane - undecamantane | —C≡CBr |
| tetramantane - undecamantane | —$C_6H_4Br$ |
| tetramantane - undecamantane | D—D |
| tetramantane - undecamantane | Br—D—D—Br |
| tetramantane - undecamantane | NC—D—D—CN |
| tetramantane - undecamantane | HOOC—D—D—COOH |
| tetramantane - undecamantane | $CH_3OC_6H_4$—D—D—$C_6H_4OCH_3$ |
| tetramantane - undecamantane | $H_2NCH_2$—D—D—$CH_2NH_2$ |
| tetramantane - undecamantane | $HClH_2NCH_2$—D—D—$CH_2NH_2HCl$ |
| tetramantane - undecamantane | —$CH_2Cl$ |
| tetramantane - undecamantane | —CH=CHCl |
| tetramantane - undecamantane | —C≡CCl |
| tetramantane - undecamantane | —$C_6H_4Cl$ |
| tetramantane - undecamantane | —$CH_2OH$ |
| tetramantane - undecamantane | —$C_6H_4OH$ |
| tetramantane - undecamantane | —OCOCl |
| tetramantane - undecamantane | —OCSCl |
| tetramantane - undecamantane | —$OCH_3$ |
| tetramantane - undecamantane | —$OCH_2CH_2NH_2$ |
| tetramantane - undecamantane | —$OCH_2C(CH_3)_2N(CH_3)_2$ |
| tetramantane - undecamantane | —$O(CH_2)_5NH_2$ |
| tetramantane - undecamantane | —$O(CH_2)_5NH_2HCl$ |
| tetramantane - undecamantane | —$OCH_2CH_2$—N⟨pyrrolidinyl⟩ |
| tetramantane - undecamantane | —$OCH_2CH_2$—N⟨morpholinyl⟩O |
| tetramantane - undecamantane | —$OCH_2CH_2NHC(O)CH_3$ |
| tetramantane - undecamantane | =O (keto) (oxide) |
| tetramantane - undecamantane | —C≡N |
| tetramantane - undecamantane | —$CH_2CO_2H$ |
| tetramantane - undecamantane | —$CH_2CO_2CH_3$ |
| tetramantane - undecamantane | —$CF_3CO_2H$ |
| tetramantane - undecamantane | —$CONHCH_2CH_3$ |
| tetramantane - undecamantane | —$NHCOCH_3$ |
| tetramantane - undecamantane | —$CH_2NH_2$ |
| tetramantane - undecamantane | =$NCH_3$ |
| tetramantane - undecamantane | —$NHCH_3$ |

TABLE 1-continued

Representative higher diamondoid derivatives

| HIGHER DIAMONDOID | SUBSTITUENT OR DERIVATIVE |
|---|---|
| tetramantane - undecamantane | —N(CH$_3$)$_2$ |
| tetramantane - undecamantane | —N$^+$(CH$_3$)$_3$ I$^-$ |
| tetramantane - undecamantane | —NH$_2$HCl |
| tetramantane - undecamantane | —CH$_2$NH$_2$HCl |
| tetramantane - undecamantane | —NHNH$_2$ |
| tetramantane - undecamantane | —NHCON$_2$ |
| tetramantane - undecamantane | —NHCONH$_2$ |
| tetramantane - undecamantane | —NHCONHSO$_2$-p-C$_6$H$_4$CH$_3$ |
| tetramantane - undecamantane | —NHCONHSO$_2$-p-C$_6$H$_4$C$_2$H$_5$ |
| tetramantane - undecamantane | —NHCONHSO$_2$-p-C$_6$H$_4$-i-C$_3$H$_7$ |
| tetramantane - undecamantane | —NHCONHSO$_2$-p-C$_6$H$_4$SCH$_3$ |
| tetramantane - undecamantane | —NHCONHSO$_2$-p-C$_6$H$_4$COCH$_3$ |
| tetramantane - undecamantane | —CH$_2$NHCONHSO$_2$-p-C$_6$H$_4$C$_2$H$_5$ |
| tetramantane - undecamantane | —CH$_2$NHCONHSO$_2$-p-C$_6$H$_4$COCH$_3$ |
| tetramantane - undecamantane | —NHCONHD |
| tetramantane - undecamantane | —NHCSNHD |
| tetramantane - undecamantane | —NHCSNHCH$_2$C$_6$H$_5$ |
| tetramantane - undecamantane | —NHCONHSO$_2$-p-C$_6$H$_4$Cl |
| tetramantane - undecamantane | —CONH$_2$ |
| tetramantane - undecamantane | —CH$_2$CONH$_2$ |
| tetramantane - undecamantane | —COCH$_3$ |
| tetramantane - undecamantane | —N=C=N—D |
| tetramantane - undecamantane | —N=C=S |
| tetramantane - undecamantane | —N=C=O |
| tetramantane - undecamantane | —N=S=O |
| tetramantane - undecamantane | —PH$_2$ |
| tetramantane - undecamantane | —POCl$_2$ |
| tetramantane - undecamantane | —PO(OH)$_2$ |
| tetramantane - undecamantane | —SO$_2$H |
| tetramantane - undecamantane | —SO$_2$CH$_3$ |
| tetramantane - undecamantane | —SOCl |
| tetramantane - undecamantane | —SO$_2$OCH$_3$ |
| tetramantane - undecamantane | —SON(CH$_3$)$_2$ |
| tetramantane - undecamantane | —N$_3$ |
| tetramantane - undecamantane | oxazolidinone (D—N—C(=O)—O—CH$_2$, NH) |
| tetramantane - undecamantane | thiazolidinone (D—N—C(=S)—O—CH$_2$, NH) |
| tetramantane - undecamantane | N-methyl oxazolidinone (D—N(CH$_3$)—C(=O)—O—CH$_2$) |
| tetramantane - undecamantane | N-methyl thiazolidinone (D—N(CH$_3$)—C(=S)—O—CH$_2$) |

Utility

As set forth above the functionalized higher diamondoids of the present invention are expected to be useful in the treatment of viral infections, in particular HIV, as well as chemical intermediates and as materials of construction.

The treatment of viral disease has been approached by inhibiting adsorption or penetration of virus into the cells, inhibiting intracellular processes which lead to the synthesis of viral components, or inhibition of release of newly synthesized virus from the infected cell. The inhibition of one or more of these steps depends on the chemistry or mode of action of the virus.

Viruses share certain common characteristics: they consist of a nucleic acid genome surrounded by a protective protein shell (capsid) and the protein shell may be enclosed in an envelope, which further includes a membrane. Viruses can multiply only inside living cells after the virus has infected the cell and the viral genome has been introduced into the cell. Animal viruses may differ in their types of nucleic acid which may be double-stranded DNA, single-stranded DNA, single-strand positive RNA, single-strand negative RNA, and double-stranded RNA.

Double-strand DNA viruses include Hepadna viruses such as the virus causing hepatitis B (Dane particle); Poxviridae such as the viruses causing smallpox (variola), swinepox, rabbit myxoma and orf; Herpesviridae such as the viruses causing herpes simplex (HSV-1 and HSV-2), cytomegaly, viral lymphoproliferative disease, Burkitt lymphoma, nasopharyngeal carcinoma in China, infectious mononucleosis (Epstein-barr) and chickenpox (varicella-zoster); and Adenoviridae such as adenovirus causing acute respiratory tract disease.

Single strand DNA viruses include Papoviridae which are non-enveloped viruses causing human warts (papillomavirus) and JC virus causing progressive multifocal leukoencephalopathy.

Positive-strand RNA viruses include Retroviridae such as the viruses causing human T-cell leukemia (HTLV-I and HTLV-II) and Acquired Immunodeficiency Disease (AIDS) (HIV-1 and HIV-2). The HIV viruses have many characteristics of lentiviruses.

Positive-strand RNA viruses also include Picornaviridae such as the enteroviruses causing polio, Coxsackie virus infections and hepatitis A.

Negative-strand RNA viruses include Orthomyxoviridae such as the viruses causing influenza A, B and C; Paramyxoviridae such as the viruses causing mumps, measles, parainfluenza, and respiratory syncytial disease (pneumovirus); and Rhabdoviridae such as the virus causing rabies.

Double-strand RNA viruses include Reoviridae such as the viruses causing certain gastroenteritis (rotavirus).

The treatment of viral disease by chemical drugs has targeted inhibition of intracellular metabolic processes which lead to the synthesis of viral constituents or release of virus from the host cell (late); and inhibition of absorption or penetration of the virus into the host cell or integration of the viral genome into that of the host cell (early).

The activity of the higher diamondoid derivatives of the present invention may be assayed by measuring the ability of the higher diamondoid derivatives to inhibit viral infections. In this regard, a cytotoxicity assay may be utilized. An effective anti-viral drug must be non-toxic to cells. Any antiviral assays must first confirm the testing candidate is not cytotoxic to the cells used in the assay. To measure the ability of higher diamondoids to inhibit viral infections, anti-HIV assays and virus neutralization assays may be utilized. Anti-HIV assays and virus neutralization assays are well known to those of skill in the art.

The higher diamondoid derivatives of Formulae I, II, and III can be administered to a patient at therapeutically effective doses to treat or ameliorate a condition, disorder, or disease as described herein. A therapeutically effective dose refers to that amount of the higher diamondoid derivative sufficient to result in amelioration of symptoms of such a condition, disorder, or disease.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds which exhibit toxic side effects may be used, care should be taken to design a delivery system which targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of the compound (i.e., an effective dosage) ranges from about 0.001 to 100 mg/kg body weight, preferably about 0.01 to 30 mg/kg body weight, more preferably about 0.1 to 20 mg/kg body weight, and even more preferably about 1 to 10 mg/kg body weight.

The skilled artisan will appreciate that certain factors may influence the dosage required to effectively treat a subject, including but not limited to the severity of the disease or condition, disorder, or disease, previous treatments, the general health and/or age of the subject, and other diseases present. Moreover, treatment of a subject with a therapeutically effective amount of the compounds can include a single treatment or, preferably, can include a series of treatments. In a preferred example, a subject is treated with the compound in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of the compound used for treatment may increase or decrease over the course of a particular treatment. Changes in dosage may result and become apparent from the results of diagnostic assays as described herein.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral rectal or topical administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In certain embodiments, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository; or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

For topical application, the compounds may be combined with a carrier so that an effective dosage is delivered, based on the desired activity.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

EXAMPLES

Introduction

The steps used in Example 1 are shown schematically in FIG. 3.

Example 1 describes a most universal route for isolating higher diamondoids components which can be applied to all feedstocks. This process uses HPLC (Step 7, FIG. 3) as its final isolation step.

Example 2 describes the bromination of a mixed tetramantane-alkyltetramantane feed and shows the preparation of a variety of mono- and polybromonated tetramantane derivatives and intermediates.

Example 3 describes the preparation of hydroxylated tetramantanes and alkyl tetramantanes.

Example 4 describes the preparation of acetaminated tetramantanes and alkyltetramantanes.

Example 5 describes the preparation of animated tetramantanes and alkyltetramantanes.

Example 6 describes the control of degree of functionalization of higher diamondoids.

Examples 7-94 describe methods that could be used to prepare various functionalized higher diamondoids.

Example 95 describes some representative pharmaceutical formations and testing assays.

Example 1

This Example has seven steps (see Flow Chart in FIG. 3).
Step 1. Feedstock selection
Step 2. GCMC assay development
Step 3. Feedstock atmospheric distillation
Step 4. Vacuum fractionation of atmospheric distillation residue
Step 5. Pyrolysis of isolated fractions
Step 6. Removal of aromatic and polar nondiamondoid components
Step 7. Multi-column HPLC isolation of higher diamondoids a) First column of first selectivity to provide fractions enriched in specific higher diamondoids.
b) Second column of different selectivity to provide isolated higher diamondoids.

This example is written in terms of isolating several hexamantanes.

Step 1—Feedstock Selection

Suitable starting materials were obtained. These materials included a gas condensate, Feedstock A and a gas condensate containing petroleum components, Feedstock B.

Step 2—GC/MS Assay Development

Feedstock A was analyzed using gas chromatography/mass spectrometry to confirm the presence of target higher diamondoids and to provide gas chromatographic retention times for these materials. This information is used to track individual higher diamondoids through subsequent isolation procedures. FIG. 4A is a table that lists typical GC/MS assay information for the hexamantanes (GC retention times, mass spectral molecular ion (M+) and base peak). This table (FIG. 4A) also contains similar GC/MS assay information for other higher diamondoids as well as HPLC retention data for these materials. While relative GC retention times are approximately constant, non-referenced GC retentions vary with time. It is recommended that GC/MS assay values be routinely updated especially when GC retention time drift is detected.

Step 3—Feedstock Atmospheric Distillation

A sample of Feedstock B was distilled into a number of fractions based on boiling points to separate the lower boiling point components (nondiamondoids and lower diamondoids) and for further concentration and enrichment of particular higher diamondoids in various fractions. The yields of atmospheric distillate fractions of two separate samples of Feedstock B are shown in Table 2, below and are contrasted to simulated distillation yields.

TABLE 2

Yields of Atmospheric Distillation Fractions from Two Separate Runs of Feedstock B

| Cut (° F.) | Sim Dis Est.'d Yields (Wt %) | Feedstock B (Run 2) Yields (Wt %) | Difference |
|---|---|---|---|
| To 349 | 8.0 | 7.6 | 0.4 |
| 349 to 491 | 57.0 | 57.7 | −0.7 |
| 491 to 643 | 31.0 | 30.6 | 0.4 |
| 643 and higher | 4.0 | 4.1 | −0.1 |

| Cut (° F.) | Sim Dis Est.'d Yields (Wt %) | Feedstock B (Run 1) Yields (Wt %) | Difference |
|---|---|---|---|
| To 477 | 63.2 | 59.3 | 3.9 |
| 477 to 515 | 4.8 | 7.3 | −2.5 |
| 515 to 649 | 28.5 | 31.2 | −2.7 |
| 649 and higher | 3.5 | 2.1 | 1.4 |

Step 4—Fractionation of Atmospheric Distillation Residue by Vacuum Distillation

The resulting Feedstock B atmospheric residium from Step 3 (comprising 2-4 weight percent of the original feedstock) was distilled into fractions containing higher diamondoids. The feed to this high temperature distillation process was the atmospheric 650° F.+ bottoms. Complete Feedstock B distillation reports are given in Tables 3A and 3B. Tables 4A and 4B illustrate the distillation reports for Feedstock B 650° F.+ distillation bottoms.

TABLE 3A

Distillation Report for Feedstock B

Feedstock B  
Column Used: Clean 9" × 1.4" Protruded Packed

| | | DISTILLATION RECORD | | | | NORMALIZED | | ACTUAL | |
|---|---|---|---|---|---|---|---|---|---|
| CUT | VAPOR TEMP ST–END | WEIGHT G | VOLUME ml @ 60° F. | API 60/60 | DENSITY @ 60° F. | WT PCT | VOL PCT | WT PCT | VOL PCT |
| 1 | 226–349 | 67.0 | 80 | 38.0 | 0.8348 | 7.61 | 8.54 | 7.39 | 8.26 |
| 2 | 349–491 | 507.7 | 554 | 22.8 | 0.9170 | 57.65 | 59.12 | 55.98 | 57.23 |
| 3 | 491–643 | 269.6 | 268 | 9.1 | 1.0064 | 30.62 | 28.60 | 29.73 | 27.69 |
| COL HOLDUP | | 0.2 | 0 | 6.6 | 1.0246 | 0.02 | 0.00 | 0.02 | 0.00 |
| BTMS | 643+ | 36.1 | 35 | 6.6 | 1.0246 | 4.09 | 3.74 | 3.98 | 3.62 |
| EOR TRAPS | | 0.0 | 0 | | | 0.00 | 0.00 | | 0.00 |
| TOTALS | | 880.6 | 937 | | | 100.00 | 100.00 | 97.09 | 96.80 |
| LOSS | | 26.4 | 31 | | | | | 2.91 | 3.20 |
| FEED | | 907.0 | 968 | 19.5 | 0.9371 | | | 100.00 | 100.00 |
| BACK CALCULATED API AND DENSITY | | | | 19.1 | 0.9396 | | | | |

TABLE 3B

Distillation Report for Feedstock B

Feedstock B  
Column Used: Clean 9" × 1.4" Protruded Packed

| TEMPERATURE DEGREES F. | | | | | | | | API GRAVITIES | | |
|---|---|---|---|---|---|---|---|---|---|---|
| VAPOR | | | PRESSURE | REFLUX | CUT | VOLUME | WEIGHT | OBSERVED | | |
| VLT | ATM EQV. | POT | TORR | RATIO | NO | ml @ 60° F. | G | HYD RDG | TEMP ° F. | 60° F. |
| 93 | 225.8 | 262 | 50.000 | 3:1 | | START OVERHEAD | | | | |
| 198 | 349.1 | 277 | 50.000 | 3:1 | 1 | 80 | 67.0 | 39.6 | 80.0 | 38.0 |
| 321 | 490.8 | 376 | 50.000 | 3:1 | 2 | 554 | 507.7 | 24.1 | 80.0 | 22.8 |

Cut 2 looks Milky, White crystals form in Run Down Line. Heat Lamp applied to drip tube.  
Cool to transfer btms to smaller flask.

| 208 | 437.7 | 323 | 10.000 | 3:1 | | START OVERHEAD | | | | |
| 378 | 643.3 | 550 | 10.000 | 3:1 | 3 | 268 | 269.6 | 9.9 | 75.0 | 9.1 |

Shutdown due to dry pot

| | | | | | END OF RUN TRAPS | 0 | 0.0 | | | |
| | | | | | VOLUME DISTILLED | 902 | | | | |
| | | | | | COLUMN HOLDUP | 0 | 0.2 | 0.0 | 0.0 | 6.6 |
| | | | | | BOTTOMS | 35 | 36.1 | 7.2 | 72.0 | 6.6 |
| | | | | | RECOVERED | 937 | 880.6 | | | |
| | | | | | FEED CHARGED | 968 | 907.0 | 20.7 | 80.0 | 19.5 |
| | | | | | LOSS | 31 | 26.4 | | | |

TABLE 4A

Vacuum Distillation Report for Feedstock B

Feedstock B - Atmospheric distillation resid 650° F. + bottoms  
Column Used: Sarnia Hi Vac

| TEMPERATURE DEGREES F. | | | | | | | | API GRAVITIES | | |
|---|---|---|---|---|---|---|---|---|---|---|
| VAPOR | | | PRESSURE | REFLUX | CUT | VOLUME | WEIGHT | OBSERVED | | |
| VLT | ATM EQV. | POT | TORR | RATIO | NO | ml 60° F. | G | HYD RDG | TEMP ° F. | 60° F. |
| 315 | 601.4 | 350 | 5.000 | | | START OVERHEAD | | | | |
| 344 | 636.8 | 382 | 5.000 | | | 300 | READING | | | |
| 342 | 644.9 | 389 | 4.000 | | | 500 | READING | | | |
| 344 | 656.3 | 395 | 3.300 | | 1 | 639 | 666.4 | 7.8 | 138.0 | 4.1 |
| 353 | 680.1 | 411 | 2.500 | | | 400 | READING | | | |
| 364 | 701.6 | 430 | 2.100 | | 2 | 646 | 666.9 | 9.4 | 138.0 | 5.6 |
| 333 | 736.0 | 419 | 0.400 | | | 200 | READING | | | |
| 336 | 751.9 | 432 | 0.300 | | 3 | 330 | 334.3 | 12.4 | 139.0 | 8.3 |

TABLE 4A-continued

Vacuum Distillation Report for Feedstock B

Feedstock B - Atmospheric distillation resid 650° F. + bottoms
Column Used: Sarnia Hi Vac

| TEMPERATURE DEGREES F. | | | PRESSURE | REFLUX | CUT | VOLUME | WEIGHT | API GRAVITIES | | |
|---|---|---|---|---|---|---|---|---|---|---|
| VAPOR | | | | | | | | OBSERVED | | |
| VLT | ATM EQV. | POT | TORR | RATIO | NO | ml 60° F. | G | HYD RDG | TEMP ° F. | 60° F. |
| 391 | 799.9 | 468 | 0.500 | | 4 | 173 | 167.7 | 19.0 | 139.0 | 14.5 |
| 411 | 851.6 | 500 | 0.270 | | 5 | 181 | 167.3 | 26.8 | 139.0 | 21.7 |
| 460 | 899.8 | 538 | 0.360 | | 6 | 181 | 167.1 | 27.0 | 139.0 | 21.9 |
| 484 | 950.3 | 569 | 0.222 | | 7 | 257 | 238.4 | 26.2 | 139.0 | 21.2 |
| | | | Shut down distillation to check pot temperature limits with customer. (Drained trap material 5.3 grams) | | | | | | | |
| 472 | 935.7 | 576 | 0.222 | | | | | START OVERHEAD | | |
| 521 | 976.3 | 595 | 0.340 | | 8 | 91 | 85.4 | 23.7 | 139.0 | 18.9 |
| 527 | 999.9 | 610 | 0.235 | | 9 | 85 | 80.8 | 23.0 | 139.0 | 18.2 |
| 527 | 1025.6 | 624 | 0.130 | | 10 | 98 | 93.8 | 21.6 | 139.0 | 16.9 |
| | | | Drained remaining trap material of 16.5 grams (~4 grams of water) | | | | | | | |
| | | MID AND | END OF RUN TRAPS | | | 20 | 17.8 | | (mathematically combined) | |
| | | | VOLUME DISTILLED | | | 2701 | | | | |
| | | | COLUMN HOLDUP | | | 4 | 4.0 | 0.0 | 0.0 | 3.4 |
| | | | BOTTOMS | | | 593 | 621.8 | 11.0 | 214.0 | 3.4 |
| | | | RECOVERED | | | 3298 | 3311.7 | | | |
| | | | FEED CHARGED | | | 3298 | 3326.3 | 18.0 | 234.0 | 8.6 |
| | | | LOSS | | | −5 | 14.6 | | | |

TABLE 4B

Distillation Report for Feedstock B-btms

Feedstock B - Atmospheric distillation resid 650° F. + bottoms
Column Used: Sarnia Hi Vac

| CUT | VAPOR TEMP ST–END | WEIGHT G | VOLUME ml @ 60° F. | API 60/60 | DENSITY 60° F. | WT PCT | VOL PCT | WT PCT | VOL PCT |
|---|---|---|---|---|---|---|---|---|---|
| 1 | 601–656 | 666.4 | 639 | 4.1 | 1.0435 | 20.12 | 19.38 | 20.03 | 19.40 |
| 2 | 656–702 | 666.9 | 646 | 5.6 | 1.0321 | 20.14 | 19.59 | 20.05 | 19.62 |
| 3 | 702–752 | 334.3 | 330 | 8.3 | 1.0122 | 10.09 | 10.01 | 10.05 | 10.02 |
| 4 | 752–800 | 167.7 | 173 | 14.5 | 0.9692 | 5.06 | 5.25 | 5.04 | 5.25 |
| 5 | 800–852 | 167.3 | 181 | 21.7 | 0.9236 | 5.05 | 5.49 | 5.03 | 5.50 |
| 6 | 852–900 | 167.1 | 181 | 21.9 | 0.9224 | 5.05 | 5.49 | 5.02 | 5.50 |
| 7 | 900–950 | 238.4 | 257 | 21.2 | 0.9267 | 7.25 | 7.79 | 7.17 | 7.80 |
| 8 | 950–976 | 85.4 | 91 | 18.9 | 0.9408 | 2.58 | 2.76 | 2.57 | 2.76 |
| 9 | 976–1000 | 80.8 | 85 | 18.2 | 0.9452 | 2.44 | 2.58 | 2.43 | 2.58 |
| 10 | 1000–1026 | 93.8 | 98 | 16.9 | 0.9535 | 2.83 | 2.97 | 2.82 | 2.98 |
| COL HOLDUP | | 4.0 | 4 | 3.4 | 1.0489 | 0.12 | 0.12 | 0.12 | 0.12 |
| BTMS | 1026+ | 621.8 | 593 | 3.4 | 1.0489 | 18.78 | 17.98 | 18.69 | 18.01 |
| EOR TRAPS | | 17.8 | 20 | | | 0.54 | 0.61 | 0.54 | 0.61 |
| TOTALS | | 3311.7 | 3298 | | | 100.00 | 100.00 | 99.56 | 100.15 |
| LOSS | | 14.6 | −5 | | | | | 0.44 | −0.15 |
| FEED | | 3326.3 | 3293 | 8.6 | 1.0100 | | | 100.00 | 100.00 |
| BACK CALCULATED API & DENSITY | | | | 9.4 | 1.0039 | | | | |

TABLE 5

Elemental Composition of Feedstock B
Analyses on Feedstock B 650 + F. Resid

| Measured | Value |
|---|---|
| Nitrogen | 0.991 wt % |
| Sulfur | 0.863 wt % |
| Nickel | 8.61 ppm |
| Vanadium | <0.2 ppm |

Table 5 illustrates the partial elemental composition of Feedstock B atmospheric distillation (650° F.) residue including some of the identified impurities. Table 5 displays the weight percent nitrogen, sulfur, nickel and vanadium in Feedstock B atmospheric distillation residue. Subsequent steps remove these materials.

Step 5—Pyrolysis of Isolated Fractions

A high-temperature reactor was used to pyrolyze and degrade a portion of the nondiamondoid components in various distillation fractions obtained in Step 4 (FIG. 3) thereby enriching the diamondoids in the residue. The pyrolysis process was conducted at 450° C. for 19.5 hours. If desired, a catalyst and added hydrogen can be used to bring about these reactions at lower temperatures.

Step 6—Removal of Aromatic and Polar Nondiamondoid Components

The pyrolysate produced in Step 5 was passed through a silica-gel gravity chromatography column (using cyclohexane elution solvent) to remove polar compounds and asphaltenes. The use of a silver nitrate impregnated silica gel (10 weight percent $AgNO_3$) provides cleaner diamondoid-containing fractions by removing the free aromatic and polar components.

Step 7—Multi-Column HPLC Isolation of Higher Diamondoids

An excellent method for isolating high-purity higher diamondoids uses two or more HPLC columns of different selectivities in succession.

The first HPLC system consisted of two Whatman M20 10/50 ODS columns operated in series using acetone as mobile phase at 5.00 mL/min. A series of HPLC fractions were taken.

Further purification of this combined ODS HPLC fraction was achieved using a Hypercarb stationary phase HPLC column having a different selectivity in the separation of various hexamantanes than the ODS column discussed above.

Example 2

Bromination of Higher Diamondoid-Containing Feedstock

Bromination of a feedstock containing a mixture of higher diamondoids was carried out. The feedstock was derived from Feedstock B described in Example 1. A sample of Feedstock B was subjected to atmospheric distillation as set forth in Example 1, Step 3. At the completion of the distillation, a holdup fraction was obtained by rinsing the column. The holdup was fractionated on a Whatman M40 10/50 ODS preparative scale HPLC column using acetone as mobile phase.

Figure 21:
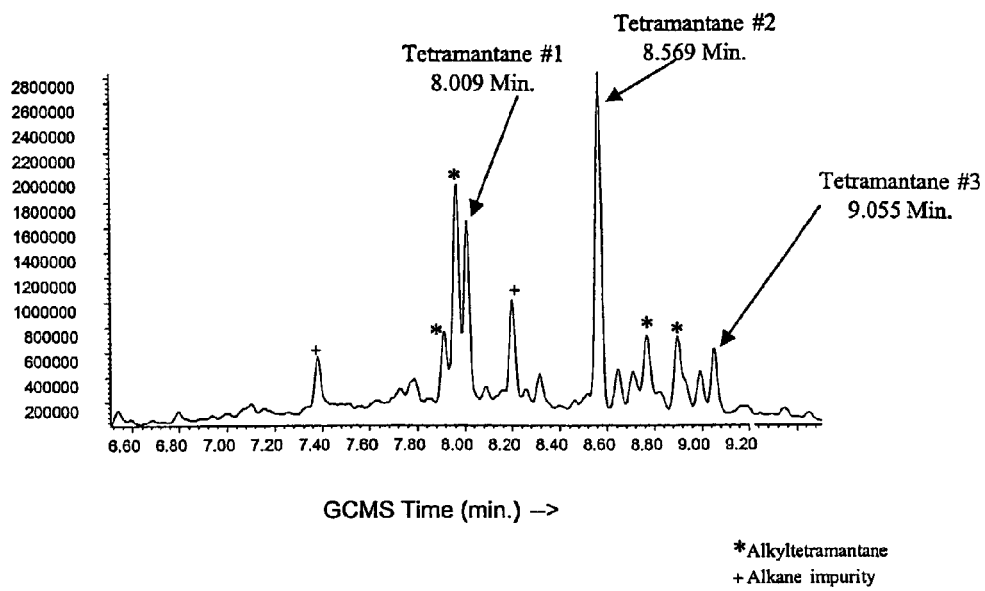
FIG. 21 illustrates the GC/MS total ion chromatogram of the feedstock used in Example 5 prior to bromination.

A fraction containing all of the tetramantanes including some alkyltetramantanes and hydrocarbon impurities was obtained. The composition of this fraction is shown in FIG. 21. The tetramantanes were identified by mass spectra and retention times.

Figure 22:
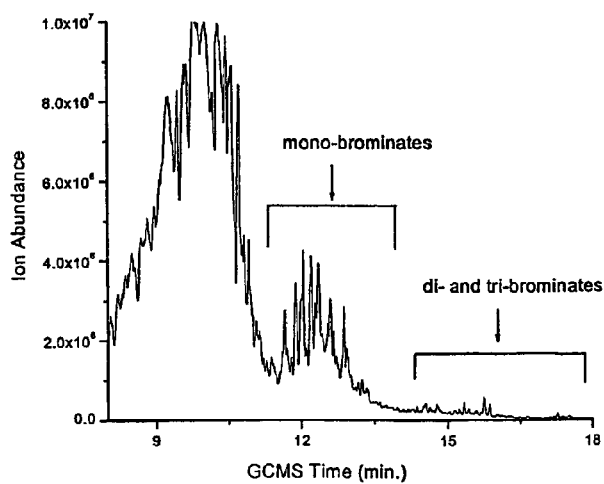
FIG. 22 shows the total ion chromatogram (TIC) of the bromination product of Example 5 including monobrominated, dibrominated and tribrominated tetramantane products formed (characterized by molecular ion 371, 447 and 527 respectively).

This fraction (about 20 mg) was mixed with excess anhydrous bromine (dried with concentrated $H_2SO_4$) in a 10 mL round-bottom flask. While stirring, the mixture was heated in an oil bath for about 4.5 hours under nitrogen, whereby the temperature was gradually raised from room temperature to about 100° C. The excess bromine was then removed by evaporation and the resulting brownish product was characterized by GC/MS analysis, shown in FIGS. 22-24 as follows:

FIG. 22 shows the total ion chromatogram (TIC) of the bromination product of Example 3 including monobrominated, dibrominated and tribrominated tetramantane products formed (characterized by molecular ion 371, 447 and 527 respectively).

Figure 23:
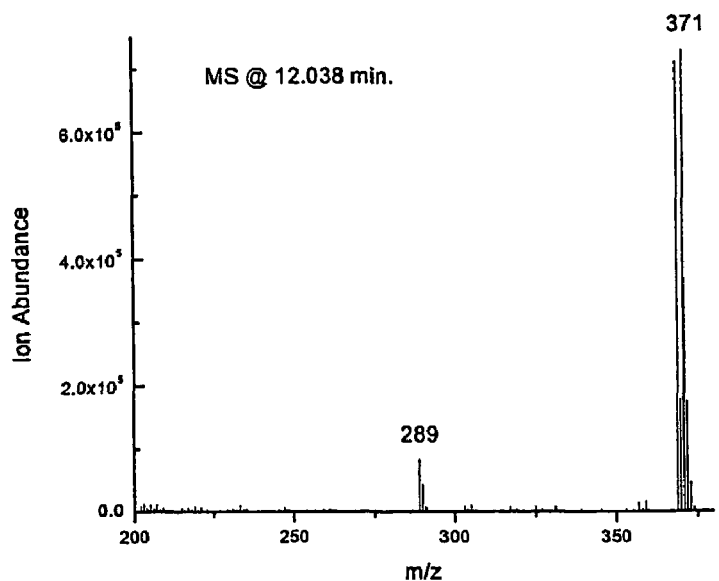
FIG. 23 is the mass spectrum of a monobrominated tetramantane with GC/MS retention time of 12.038 minutes. The base peak in this spectrum is the m/z 371 molecular ion.

FIG. 23 is the mass spectrum of a monobrominated tetramantane with GC/MS retention time of 12.038 minutes. The base peak in this spectrum is the m/z 371 molecular ion.

Other mass spectra revealed monobrominated methyltetramantanes with GC/MS retention times of 11.992 minutes and 11.644 minutes and a base peak in this spectrum is the m/z 385 molecular ion; a monobrominated dimethyltatramantane with GC/MS retention time of 12.192 minutes; a dibrominated tetramantane with GC/MS retention time of 15.753 minutes with a base peak of the m/z 447 molecular ion; a dibrominated methyltetramantane with GC/MS retention time of 15.879 minutes with the base peak of m/z 461 molecular ion; and dibrominated dimethyltetramantanes with GC/MS retention times of 13.970 and 14.318 minutes with a base peak of the m/z 475 molecular ion.

Figure 24:
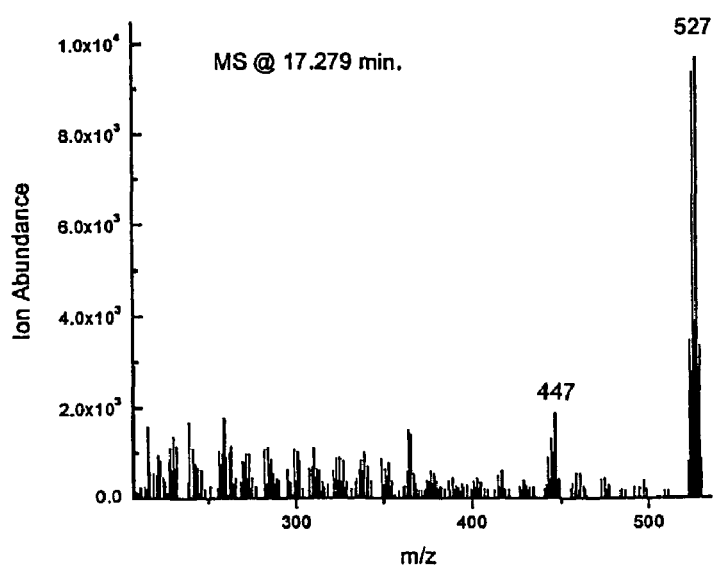
FIG. 24 is the mass spectrum of a tribrominated tetramantane with GC/MS retention time of 17.279 minutes. The base peak in the spectrum is the m/z 527 molecular ion.

FIG. 24 is the mass spectrum of a tribrominated tetramantane with GC/MS retention time of 17.279 minutes. The base peak in the spectrum is the m/z 527 molecular ion.

Other mass spectra showed tribrominated methyltetramantanes with GC/MS retention times of 15.250 and 16.050 minutes.

Example 3

Hydroxylation of Brominated Tetramantanes

The brominated tetramantanes of Example 2 are mixed with about 1 mL of 0.67 N hydrochloric acid and 5 mL DMF. The resultant mixture is stirred at reflux temperature for about 1 hour. The mixture is then neutralized and the solvent was evaporated. The resulting product mixture was characterized by GC/MS analysis.

Figure 25:
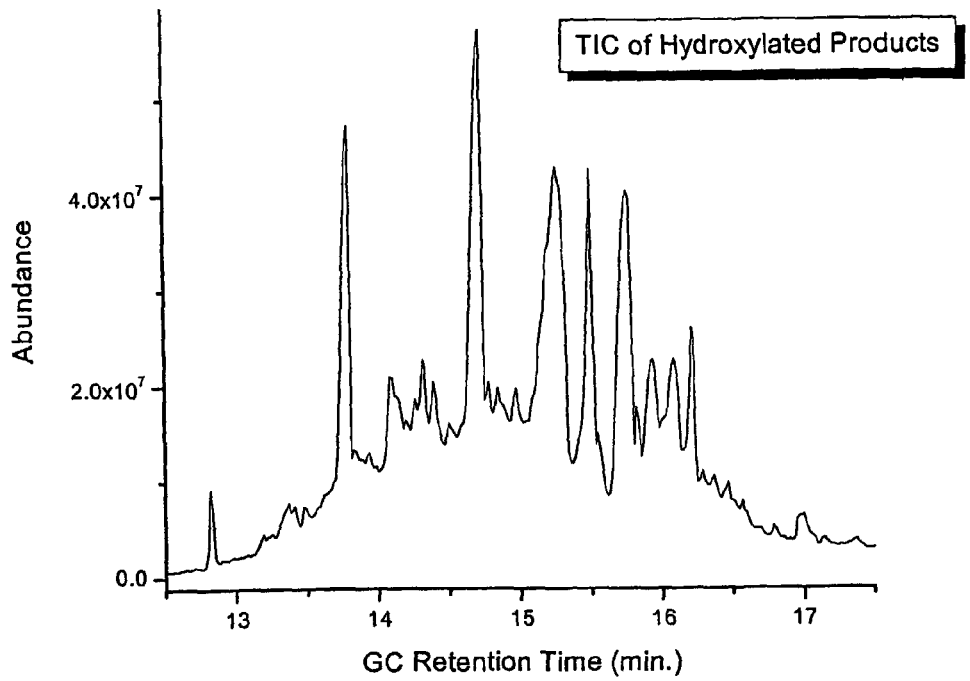
FIG. 25 shows the total ion chromatogram (TIC) of the hydroxylation product of Example 6.

FIG. 25 shows the total ion chromatogram (TIC) of the hydroxylation product of Example 3.

Figure 26:
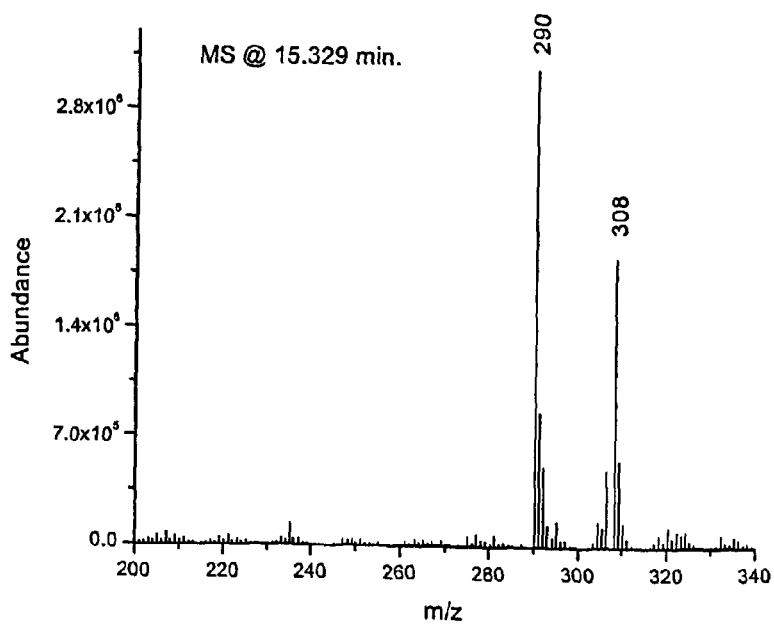
FIG. 26 is the mass spectrum of a monohydroxylated tetramantane with GC/MS retention time of 15.329 minutes.

FIG. 26 is the mass spectrum of a monohydroxylated tetramantane with GC/MS retention time of 15.329 minutes.

Other mass spectrum showed a monohydroxylated methyltetramantane with GC/MS retention time of 15.281 minutes and a monohydroxylated dimethyltetramantane with GC/MS retention time of 15.925 minutes.

Example 4

Acetaminated Tetramantanes from Hydroxylated Compounds

The above prepared hydroxylated tetramantanes are dissolved in about 3 mL acetonitrile. While stirring the mixture, about 1 mL concentrated sulfuric acid is slowly added to the solution, whereby the mixture heats up by the reaction. After the mixture has been stirred for about 12 hours and then left standing for about another 12 hours, the orange red solution is poured into about 10 mL ice water, whereby the acetaminated higher diamondoids are separated out by filtration in high purity. By extracting the filtrate with $CH_2Cl_2$, an additional small amount of the reaction product can be obtained. The products were then characterized by GC/MS analysis.

Figure 27:
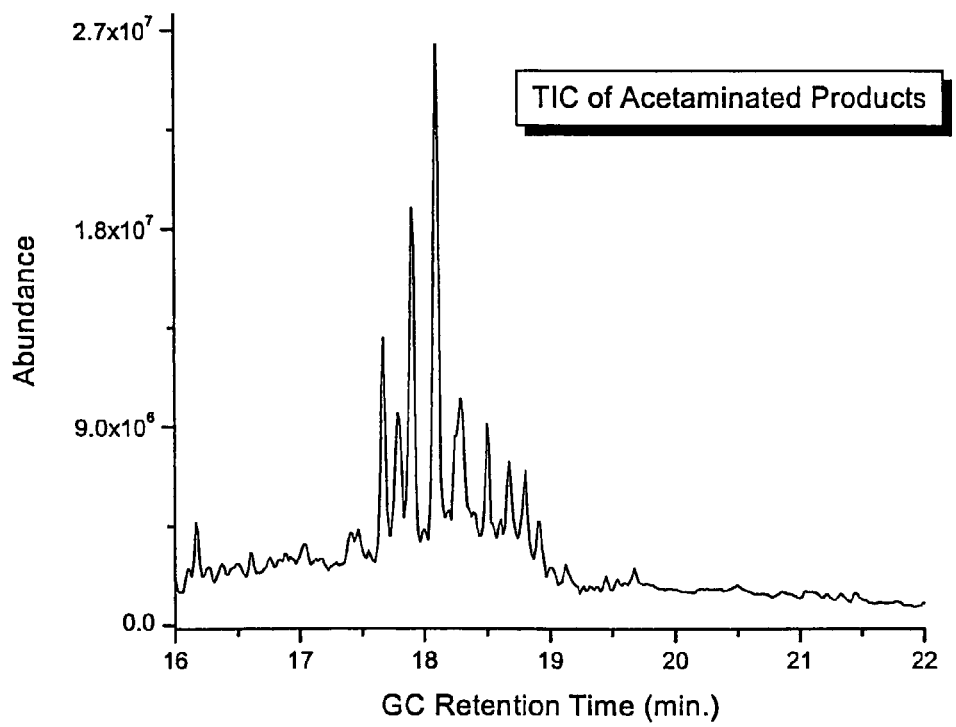
FIG. 27 shows the total ion chromatogram (TIC) of the acetamination product of Example 7.

FIG. 27 shows the total ion chromatogram (TIC) of the acetamination product.

Figure 28:
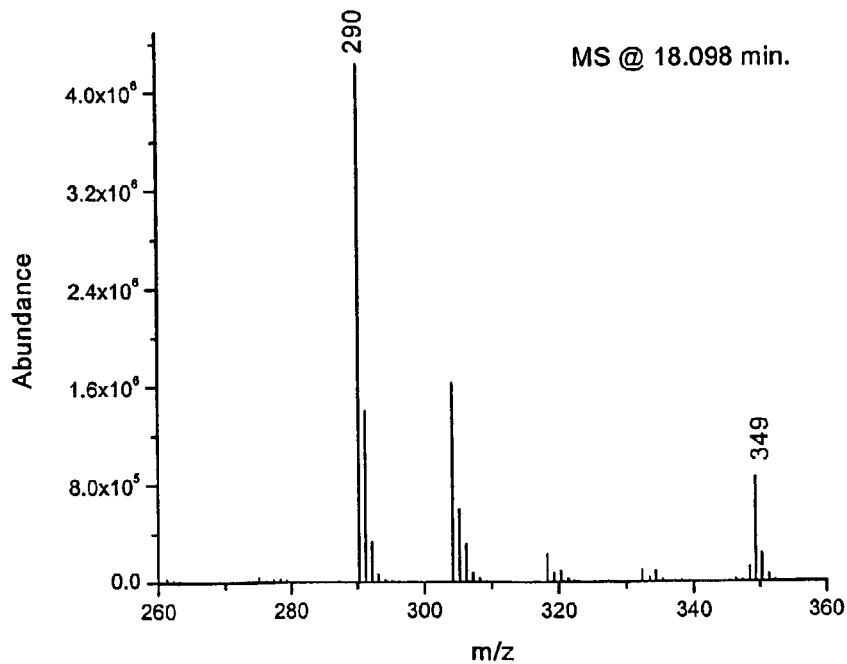
FIG. 28 is the mass spectrum of a monoacetaminated tetramantane with GC/MS retention time of 18.098 minutes.

FIG. 28 is the mass spectrum of a monoacetaminated tetramantane with GC/MS retention time of 18.098 minutes.

Other monoacetaminated methyltetramantanes were present in the reaction product of this Example.

These included a monoacetaminated methyltetramantane with GC/MS retention time of 17.905 minutes and a diacetaminated tetramantane with GC/MS retention time of 21.468 minutes.

Example 5

Aminated Tetramantanes from Acetaminated Compounds

The above prepared acetaminated tetramantanes is heated to about 200° C. for about 5 hours with a solution of powdered sodium hydroxide (excess) in 2 mL diethylene glycol. After it has been cooled down, the red mixture is poured into 10 mL water and extracted with $CH_2Cl_2$. The extract is dried with Na$_2$CO$_3$. After filtration, the solvent was evaporated and the residue was characterized by GC/MS analysis.

Figure 29:
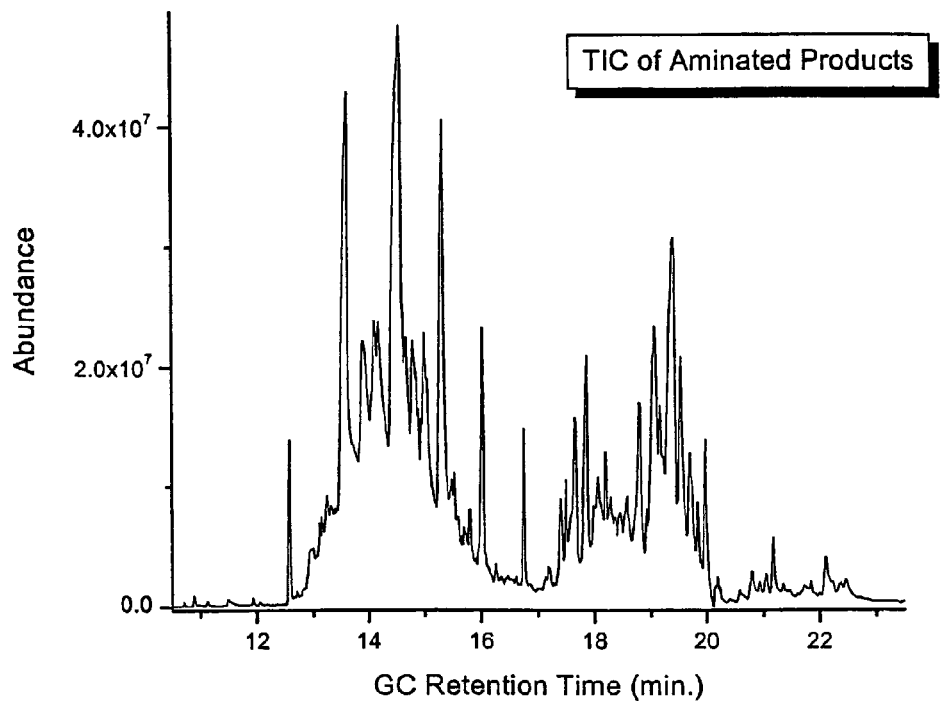
FIG. 29 shows the total ion chromatogram (TIC) of the amination product of Example 8.

FIG. 29 shows the total ion chromatogram (TIC) of the amination product of this Example.

Figure 30:
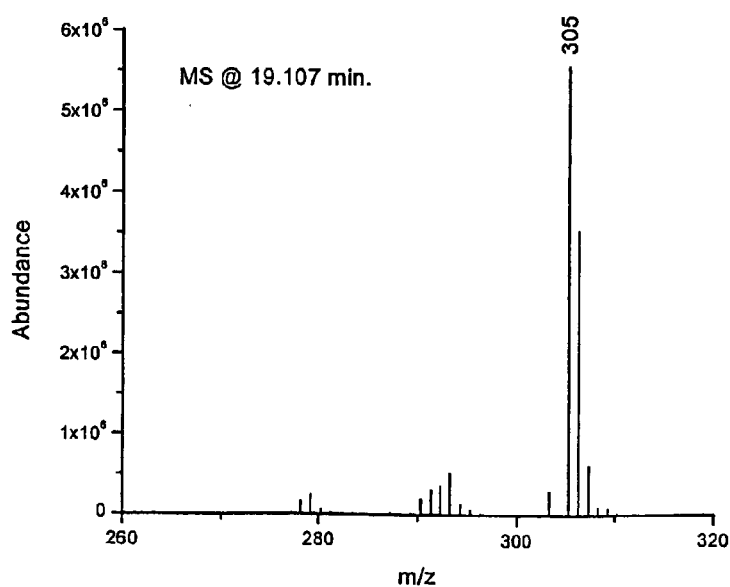
FIG. 30 is the mass spectrum of a monoaminated tetramantane with GC/MS retention time of 19.107 minutes.

FIG. 30 is the mass spectrum of a monoaminated tetramantane with GC/MS retention time of 19.107 minutes, while a monoaminated methyltetramantanes was seen with GC/MS retention time of 18.816 minutes and a monoacetaminated dimethyltetramantanes was found with GC/MS retention time of 19.918 minutes.

Example 6

Control of Degree of Functionalization of Higher Diamondoids

Higher diamondoid has two types of active carbons (secondary and tertiary carbons) on which functionalization is possible, and furthermore, of those active carbons such as either secondary or tertiary carbon they are not all equivalent. This means, theoretically speaking, there are many possible functionalized derivatives for either mono-, di-, or higher functionalized compounds. In addition, the degree of functionalization of higher diamondoids are variable. However, by way of control reaction conditions or reaction mechanism (see above), it is possible to control the degree of functionalization to prepare, for example, the mono-, di-, or tri-functionalized derivatives as the major products. This was well demonstrated by the bromination reaction as shown in FIG. 8. If the reaction was performed without catalyst and at room temperature, the mono-brominated product dominates the bromination product mixture. If trace amount of BBr$_3$—AlBr$_3$ is used, the di-brominated derivative is the major product, and with increasing the reaction temperature, reaction time, and the amount of the catalyst, tri-, and tetra-brominated derivatives become the major product. For example, a higher diamondoid (37 mol) is heated to 150° C. for about 22 h with anhydrous bromine (0.37 mol) in a pressure vessel. Usual work-up and purification affords a pure dibrominated derivative as the major product. For another example, to a stirred mixture of 1.0 mole anhydrous bromine and 0.025 mole (2.5 mL) of boron bromide is added a few milligrams of aluminum bromide. The reaction mixture is maintained under a blanket of nitrogen during addition of reactants to a four-necked flask with stirrer, reflux condenser, and gas inlet. A higher diamondoid (0.1 mole) is added portionwise from a small flask attached to the fourth neck by means of Gooch crucible tubing. After refluxing for about 1.5 hours, hydrogen bromide evolution is no longer evident. Excess bromine is decomposed and the product isolation is accomplished as described above. After removal of the solvent, the residue is recrystallized from methanol and n-hexane at room temperature to provide a pure dibrominated compound as major product.

In addition to control the reaction parameters or mechanism to control the degree of functionalization, there is another way to control the degree of functionalization via repeated functionalization. For example, when separated the mono-functionalized derivative, use it as the starting material for further functionalization such as from mono- to di-, and from di- to tri-, from tri- to tetra-, and so on. It is understood that for some cases or maybe most cases, the reaction will become more and more difficult and this will need to adjust the reaction parameters such as increase the reaction time or temperature.

In another aspect, it is very convenient to use a primary functionalized derivative with specific degree of functionalization to prepare other derivatives with the same degree of functionalization. For example, hydroxylated derivatives can be readily made from corresponding brominated compounds (see Examples 14 and 15 below).

The above three ways of controlling the degree of functionalization of higher diamondoids are just representative examples. Based on the nature of the reaction and the starting material such as higher diamondoid, there should be other ways to control the degree of functionalization, which is known for the skilled in the art.

Example 7

D—CH$_2$CH$_2$—Br from D—Br

A solution of a suitable monobrominated higher diamondoid D—Br (0.046 mole) in 15 mL n-hexane in a 150-mL three-necked flask equipped with a stirrer, a gas inlet tube and a gas discharge tube with a bubble counter is cooled to −20 to −25° C. in a cooling bath. While stirring one introduces 4.0 g powdered freshly pulverized aluminum bromide of high quality, and ethylene is conducted in such a way that the gas intake can be controlled with the bubble counter. The reaction starts with a slight darkening of the color and is completed after about 1 h. The reaction solution is decanted from the catalyst into a mixture of ether and water. The ether layer is separated off, and the aqueous phase is extracted once more with ether. The combined ether extracts are washed with water and dilute sodium carbonate aqueous solution. After they have been dried over calcium chloride, the solvent is distilled off. Recrystallizing from methanol affords the pure higher diamondoidyl ethyl bromide D—CH$_2$CH$_2$—Br.

Alkylation and Dehydrogen Bromide Reaction for the Synthesis of Higher Diamondoid Substituted Alkenyl Bromides [D-(Alkenyl-Br)$_n$]

Example 7A

D—CH=CH—Br from D—Br

Step 1: in a 150-mL two-necked flask with a stirrer and a drying tube, a mixture of 0.069 mole of a suitable monobromonated higher diamondoid D—Br and 20 mL vinyl bromide is cooled to −65° C. in a cooling bath. While stirring, 4.5 g powdered aluminum bromide is added in portions and the mixture is stirred for an additional about 3 hours at the same temperature. Then the reaction mixture is poured into a mixture of 30 mL water and 30 mL ethyl ether. After vigorously stirring, the ether layer is separated and the aqueous layer is extracted once more with ether. The combined ether extracts are washed with water and dilute sodium carbonate solution. After it has been dried with calcium chloride and the solvent has been distilled off, the residue is distilled under vacuum.

Step 2: a solution of 0.7 g fine powdered potassium hydroxide and the above compound (0.012 mole) in 10 mL diethylene glycol is heated to 220° C. in the oil bath for 6 hours. After cooling down the mixture is diluted with 30 mL water and exacted with ethyl ether. The ether extract is washed twice with water and dried over calcium chloride. The residue left behind after the ether has been distilled off is sublimated in vacuum, and if necessary, the compound can be recrystallized from methanol.

Alkylation and Dehydrogen Bromide Reaction for the Synthesis of Higher Diamondoid Substituted Alkynyl Bromides [D-(Alkynyl-Br)$_n$]

Example 8

D—C≡C—Br from D—Br

Step 1: in a 150-mL two-necked flask with a stirrer and a drying tube, a mixture of 0.069 mole of a suitable monobromonated higher diamondoid D—Br and CH$_2$=CBr$_2$ (excess) is cooled to −65° C. in a cooling bath. While stirring, 4.5 g powdered aluminum bromide is added in portions and the mixture is stirred for an additional about 3 hours at the same temperature. Then the reaction mixture is poured into a mixture of 30 mL water and 30 mL ethyl ether. After vigorously stirring, the ether layer is separated and the aqueous layer is extracted once more with ether. The combined ether extracts are washed with water and dilute sodium carbonate solution. After it has been dried with calcium chloride and the solvent has been distilled off, the residue is distilled under vacuum.

Step 2: 15 g powdered potassium hydroxide in 30 mL diethylene glycol is heated to reflux with 0.046 mole of the above product for about 9 hours in the oil bath. Compound formed is then sublimated in the condenser and must be returned to the reaction mixture from time to time. At the end of the reaction time, the reaction mixture is distilled until no more solid particles go over. The distillate is extracted with ethyl ether and the ether phase is washed with water and dried over calcium chloride. A short time after the ether has been distilled off, the residue solidifies. It is sublimated under vacuum and, if necessary, recrystallized from methanol.

Arylation Reaction for the Synthesis of Higher Diamondoid Substituted Aryl Bromides [D-(Aryl-Br)$_n$]

Example 9

D—C$_6$H$_4$—Br from D—Br 1.1 g sublimated iron(III) chloride and high-pure C$_6$H$_5$Br (excess) are placed in a 150-mL three-necked flask, which is equipped with a stirrer, a reflux condenser and a dropping funnel. While stirring and heating in the steam bath, a suitable monobrominated higher diamondoid D—Br (0.018 mole) is slowly added to the above flask over about 30 minutes. The reaction mixture is heated for about an additional 3 hours until the production of hydrogen bromide drops off. The mixture is kept standing over night and poured onto a mixture of ice and hydrochloric acid. The organic phase is separated out and the aqueous solution is extracted twice with benzene. The combined benzene extracts are washed several times with water and dried with calcium chloride. The residue solidifies upon cooling and is completely free of the solvent in vacuum. Recrystallization from a small amount of methanol while cooling with CO$_2$/trichloroethylene and further sublimation under vacuum afford a pure product.

Synthesis of Higher Diamondoidyl Chlorides [D—(Cl)$_n$] and Higher Diamondoid Substituted Alkyl, Alkenyl, Alkynyl or Aryl Chlorides [D-(Alkyl-Cl)$_n$, D-(Alkenyl-Cl)$_n$, D-(Alkynyl-Cl)$_n$, or D-(Aryl-Cl)$_n$] (n=1, 2, 3, 4, ...)

Similarly to higher diamondoid substituted alkyl, alkenyl, alkynyl, or aryl bromides, higher diamondoid substituted alkyl, alkenyl, alkynyl or aryl chlorides [D-(Alkyl-Cl)$_n$, D-(Alkenyl-Cl)$_n$, D-(Alkynyl-Cl)$_n$, or D-(Aryl-Cl)$_n$] (n=1, 2, 3, 4, ...) can be prepared accordingly.

Via Chlorination Reaction of Higher Diamondoids

Example 10

Monochlorination of Higher Diamondoids

A solution of 0.074 mole of a higher diamondoid and 10 mL (8.5 g, 0.092 mole) of tert-butyl chloride in 40 mL of anhydrous cyclohexane is prepared in a 0.1 L, three-necked, round-bottom flask fitted with a thermometer, a stirrer, and a gas exhaust tube leading to a bubbler submerged in water. The catalyst, aluminum chloride (total 0.46 g, 0.006 mole) is added in batches of 0.05 g at regular intervals over a period of about 8 hours. Progress of the reaction is followed conveniently by the rate of escaping isobutane gas. Upon completion of the reaction, 10 mL of 1.0 N hydrochloride acid solution is added with vigorous stirring, followed by 50 mL of ethyl ether. The organic layer is separated, washed with 10 mL of cold water and 10 mL of a 5% sodium bicarbonate solution, and dried over anhydrous calcium chloride. After removal of the solvents under reduced pressure, the crude product is obtained. GC analysis of this material reveals a composition of mainly monochlorinated higher diamondoid with a small amount of unreacted higher diamondoid. If necessary, recrystallization of a sample of this material from ethanol at −50° C. affords a pure monochlorinated higher diamondoid.

Via Photochlorination Reaction of Higher Diamondoids

Example 11

Monophotochlorination of Higher Diamondoids

Photochlorination of a higher diamondoid is carried out at room temperature (25-30° C.) by metering 0.037 mole of chlorine into a solution of 0.074 mole of a higher diamondoid in 100 mL of solvent in the presence of illumination by a 150-watt ultraviolet (UV) lamp. The solvents employed can be carbon tetrachloride, benzene, or carbon disulfide. After a short induction period (approximately 2 minutes) the reaction may be initiated as evidenced by the fading of the chlorine color and the evolution of hydrogen chloride. The reaction mixture is washed by 5% sodium carbonate aqueous solution, water, and dried over anhydrous sodium sulfate. The product obtained by concentration of the dried solution is shown by GC to consist of several mono-chlorinated higher diamondoid isomers. Separation of those isomers is achieved by HPLC or even normal column chromatography on alumina or silicon gel or simply by recrystallization from methanol and sublimation under vacuum or their combination to achieve the isomer separation.

Synthesis of Hydroxylated Higher Diamondoids (Higher Diamondoidols, D—(OH)$_n$) and Higher Diamondoid Substituted Alcohols (e.g. D-(Alkyl-OH)$_n$)(n=1, 2, 3, 4, ...)

Via Direct Oxidation or Hydroxylation Reaction of Higher Diamondoids

Example 12

Monohydroxylation of Higher Diamondoids

A solution of 11.0 mmol of a higher diamondoid in 18.7 g of methylene chloride is mixed with 4.22 g of a solution of 1.03 g (13.5 mmol) of peracetic acid in ethyl acetate. While being stirred vigorously, the solution is irradiated with a 100-watt UV light placed in an immersion well in the center of the solution. Gas evolution is evident from the start. The temperature is maintained at 40-45° C. for an about 21-hour irradiation period. At the end of this time, about 95% of the peracid had been consumed. The solution is concentrated to near dryness, treated twice in succession with 100-mL portions of toluene and reevaporated to dryness. Final drying in a desiccator affords a white solid. A portion of the above material is dissolved in a minimum amount of benzene-light petroleum ether. This solution is then subjected to chromatography on alumina in the usual manner eluting with firstly 1:1 benzene/light petroleum ether, followed by a mixture of methanol and ethyl ether to collect the unreacted higher diamondoid, and the hydroxylated higher diamondoid isomers, respectively. Further separation of the isomers can be achieved by using HPLC technique.

Alternatively, to a 25 mL of acetic acid are added 10 mmol of a higher diamondoid, 0.8 mmol of N-hydroxyphthalimide (NHPI) and 0.6 mmol of acetylacetonatocobalt(II). The resultant mixture is stirred in an oxygen atmosphere at a temperature of 75° C. for about 3 hours. The reaction is monitored by GC, allowing isolation of the monohydroxylated higher diamondoid upon completion.

Example 13

Polyhydroxylation of Higher Diamondoids

Into a 4-neck flask immersed in a cooling bath and equipped with a low temperature condenser (−20° C.), and an air driven, well sealed mechanical stirrer, a solid addition funnel and a thermocouple, is added 0.037 mole of a higher diamondoid, 150 mL methylene chloride, 200 mL double distilled water, 192 grams sodium bicarbonate and 300 mL t-butanol. The mixture is stirred and cooled to 0° C. and 200 grams 1,1,1-trifluoro-2-propanone (TFP) are added. The mixture is stirred and cooled down to −8° C. 200 grams oxone are added from the solid addition funnel over the course of 3 hours. The reaction mixture is stirred at 0° C. overnight (16 hours). The TFP is recovered by distillation (heating pot to 40° C. and condensing TFP in a receiver immersed in dry ice/acetone). The remainder mixture is filtered by suction and a clear solution is obtained. The solution is rotavapped to dryness, providing a mixture of polyhydroxylated higher diamondoids that are purified by chromatography and/or recrystallization.

Via Substitution of Brominated Higher Diamondoids [D—(Br)$_n$] or Higher Diamondoid Substituted Bromides [e.g. D-(Alkyl-Br)$_n$]

Example 14

Monohydroxylated Higher Diamondoids from Monobrominated Compounds

A suitable monobrominated higher diamondoid (0.066 mol) is heated to reflux for about 1 h in a round bottom flask, which is equipped with a stirrer and a reflux condenser, while stirring and adding 35 mL water, 3.5 mL tetrahydrofuran, 2.0 g potassium carbonate and 1.3 g silver nitrate. After cooling, the reaction product, which has crystallized, is separated out and is extracted with tetrahydrofuran. The extract is diluted with water and the precipitate is suctioned off, dried and purified by sublimation under vacuum.

Alternatively, a suitable monobromo higher diamondoid (0.1 mole) is mixed with 40 mL of 0.67 N hydrochloric acid and 450 mL DMF. The resultant mixture is stirred at reflux temperature for about 1 hour. The solid product is filtered and recrystallized from n-hexane to produce the monohydroxylated higher diamondoid.

Example 15

Dihydroxylated Higher Diamondoids from Dibrominated Compounds

A suitable dibrominated higher diamondoid (0.066 mol) is heated to reflux for about 1 h in a round bottom flask, which is equipped with a stirrer and a reflux condenser, while stirring and adding 70 mL water, 10 mL tetrahydrofuran, 4.0 g potassium carbonate and 2.6 g silver nitrate. After cooling, the reaction product is separated out and extracted with tetrahydrofuran. The extract is diluted with water and the precipitate is suctioned off, dried and purified by sublimation under vacuum.

Alternatively, a mixture of a dibromo higher diamondoid (0.12 mole) and 70% nitric acid (200 mL) is heated at 70-75° C. until bromine evolution ceases. The reaction mixture is poured into water (250 mL) and the precipitate is filtered. The filtrate is made alkaline with 10% aqueous sodium hydroxide and the mixture is filtered. The combined precipitates are washed with water (3×200 mL) and acetone (2×150 mL) and dried to provide the desired compound.

Example 16

D—CH$_2$CH$_2$—OH from D—CH$_2$CH$_2$Br

A suitable D—CH$_2$CH$_2$—Br (0.066 mol) is heated to reflux for about 1 h in a round bottom flask, which is equipped with a stirrer and a reflux condenser, while stirring and adding 35 mL water, 3.5 mL tetrahydrofuran, 2.0 g potassium carbonate and 1.3 g silver nitrate. After cooling, the reaction product is separated out and is extracted with chloroform. Evaporating the solvent affords the product after purification by column chromatography.

Via Reduction of Keto Higher Diamondoids (Higher Diamondoidones) for the Synthesis of C-2 Hydroxylated Higher Diamondoids (Substituted at the Secondary Carbons)

Example 17

C-2 D—OH from D=O

A suitable higher diamondoidone D=O is reduced with lithium aluminum hydride (a little excess) in ethyl ether at low temperatures. After completion of the reaction, the reaction mixture is worked up by adding saturated Na$_2$SO$_4$ aqueous solution to decompose excess hydride at low temperature. Decantation from the precipitated salts gives a dry ether solution, which, when evaporated, affords a crude C-2 monohydroxylated higher diamondoid substituted at the secondary carbon, i.e. C-2 D—OH. Further recrystallization from cyclohexane gives a pure sample.

Esterification of Hydroxylated Higher Diamondoids and Higher Diamondoid Substituted Alcohols Example 18

Diesterified Higher Diamondoids from Dihydroxylated Compounds

To 2 mL of dioxane is added a dihydroxylated higher diamondoid (1.0 mmol) and triethylamine (2.2 mmol) at a temperature of 50° C. The resultant mixture is added dropwise to a solution of acrylic acid chloride (2.2 mmol) in dioxane (2 mL). The mixture is maintained at 50° C. for about 1 hour. The product is analyzed by GC. When the analysis confirms the formation of the desired diacrylate, the compound is isolated using standard methods.

Example 19

D—$CH_2CH_2$—OCOCH$_3$ from D—$CH_2CH_2$—OH

To 2 mL of dioxane is added a D—$CH_2CH_2$—OH (1.0 mmol) and triethylamine (2.2 mmol) at a temperature of 50° C. The resultant mixture is added dropwise to a solution of $CH_3COCl$ (1.1 mmol) in dioxane (2 mL). The mixture is maintained at 50° C. for about 1 hour. The product is analyzed by GC. When the analysis confirms the formation of the desired compound, the product is isolated using standard methods.

Synthesis of Keto Higher Diamondoids (Higher Diamondoidones, [D(=O)$_n$]) and Reactions Thereof

Example 20

Oxidation of Higher Diamondoids to Higher Diamondoidones

A solution of 11.0 mmol of a suitable higher diamondoid in 18.7 g of methylene chloride is mixed with 4.22 g of a solution of 1.03 g (13.5 mmol) of peracetic acid in ethyl acetate. While being stirred vigorously, the solution is irradiated with a 100-watt UV light placed in an immersion well in the center of the solution. Gas evolution is evident from the start. The temperature is maintained at 40-45° C. for an about 21-hour irradiation period. At the end of this time, about 95% of the peracid had been consumed. The solution is concentrated to near dryness, treated twice in succession with 100-mL portions of toluene and reevaporated to dryness. Final drying in a desiccator affords a solid.

The crude, hydroxylated higher diamondoid mixture is then partially dissolved in acetone. The oxygenated components go into the solution but not all of the unreacted higher diamondoid. Chromic acid-sulfuric acid solution is added dropwise until an excess is present, and the reaction mixture is stirred overnight. The acetone solution is decanted from the precipitated chromic sulfate and the unreacted higher diamondoid, and is dried with sodium sulfate. The unreacted higher diamondoid is recovered by dissolving the chromium salts in water and filtering. Evaporation of the acetone solution affords a solid. This crude solid is chromatographed on alumina with standard procedures eluting first with 1:1 (v/v) benzene/light petroleum ether followed by ethyl ether or a mixture of ethyl ether and methanol (95:5 v/v) to collect the unreacted higher diamondoid and the higher diamondoidone, respectively. Further purification by recrystallization from cyclohexane affords a pure higher diamondoidone.

Example 21

2,2-Bis(4-hydroxyphenyl) Higher Diamondoids from Keto Compounds

A flask is charged with a mixture of a higher diamondoidone (0.026 mole), phenol (16.4 g, 0.17 mole), and butanethiol (0.15 mL). Heat is applied and when the reaction mixture becomes liquid at about 58° C., anhydrous hydrogen chloride is introduced until the solution becomes saturated. Stirring is continued at about 60° C. for several hours, during which period a white solid begins to separate out from the reaction mixture. The solid obtained is filtered off, washed with dichloromethane and dried to afford the bisphenol higher diamondoid product. It is purified by sublimation after recrystallization from toluene.

Example 22

2,2-Bis(4-aminophenyl) Higher Diamondoids from Keto Compounds

To a solution of a higher diamondoidone (0.041 mole) in 15 mL of 35% HCl aqueous solution in a 100 mL autoclave equipped with a stirrer is added excess aniline (15.7 g, 0.17 mole) and the mixture is stirred at about 120° C. for about 20 hours. After cooling, the solution is made basic with NaOH aqueous solution to pH 10 and the oily layer is separated and distilled to remove the unreacted excess aniline. The residual crude product is recrystallized from benzene to afford the higher diamondoid derived bisphenylamine.

Example 23

2,2-Bis[4-(4-aminophenoxy)phenyl] Higher Diamondoids from Bisphenol Higher Diamondoids A mixture of a 2,2-bis(4-hydroxyphenyl) higher diamondoid (0.01 mole), p-fluoronitrobenzene (3.1 g, 0.022 mole), potassium carbonate (3.31 g, 0.024 mole) and N,N,-dimethylacetamide (DMAc, 10 mL) is refluxed for about 8 hours. The mixture is then cooled and poured into a ethanol/water mixture (1:1 by volume). The crude product is crystallized from DMF to provide yellow needles of the 2,2-bis[4-(4-nitrophenoxy)phenyl] higher diamondoid.

Hydrazine monohydrate (20 mL) is added dropwise to a mixture of the above product (0.002 mole), ethanol (60 mL), and a catalytic amount of 10% palladium on activated carbon (Pd/C, 0.05 g) at the boiling temperature. The reaction mixture is refluxed for about 24 hours, and the product 2,2-Bis[4-(4-aminophenoxy)phenyl] higher diamondoid is precipitated during this period. The mixture is then added to enough ethanol to dissolve the product and filtered to remove Pd/C. After cooling, the precipitated crystals are isolated by filtration and recrystallized from 1,2-dichlorobenzene.

Synthesis of Nitro Higher Diamondoids [D—(NO$_2$)$_n$] (n=1, 2, 3, 4, . . . )

Via Direct Nitration Reaction of Higher Diamondoids

Example 24

Mononitration of Higher Diamondoids

A mixture of 0.05 mole of a higher diamondoid and 50 mL of glacial acetic acid is charged to a stirred stainless 100 mL autoclave which is pressurized with nitrogen to a total pressure of 500 p.s.i.ga. After the mixture is then heated to 140° C., 9.0 g (0.1 mole) of concentrated nitric acid is introduced into the reaction zone by means of a feed pump at a rate of 1-2 mL per minute. When the acid feed is completed, the reaction temperature is maintained at 140° C. for 15 minutes, after which time the reaction mixture is cooled down to room temperature and diluted with an excess of water to precipitate the products. The filtered solids are slurried with a mixture of 10 mL of methanol, 15 mL of water, and 1.7 g of potassium hydroxide for 18 hours at room temperature. After dilution with water, the alkali-insoluble material is extracted by light petroleum ether. The petroleum ether extracts are washed by water and dried over anhydrous magnesium sulfate. Concentration of this solution affords a white solid. The aqueous alkali solution from which the alkali-insoluble material had been extracted is cooled to 0-3° C. and neutralized by the dropwise addition of an aqueous acetic acid-urea mixture to regenerate some more products. GC analysis shows that the alkali-insoluble sample is mainly mononitro higher diamondoid with a small amount of dinitro product. Recrystallization from methanol and repeated sublimation, yields the mononitro higher diamondoid.

Via Oxidation of Amino Higher Diamondoids [D—$(NH_2)_n$]

Example 25

Mononitro Higher Diamondoids from Monoamino Compounds

A suspension of 0.01 mole of a suitable monoaminated higher diamondoid in 50 mL water is heated to 60° C. To this suspension is gradually added dropwise a solution of 3.5 g potassium permanganate in 50 mL water (about 1 hour). After this has been added, the mixture is heated to reflux for about 2 hours, whereby the fraction sublimating in the condenser is washed back in again. The crystals are purified twice by sublimation under vacuum.

Synthesis of Higher Diamondoidyl Carboxylic Acids (Higher Diamondoidyl Acetic Acid) [D—$(CO_2H)_n$] (n=1, 2, 3, 4, ...)

Via Direct Carboxylation Reaction of Higher Diamondoids

Example 26

Monocarboxylation of Higher Diamondoids

A mixture of 29.6 g (0.4 mole) tert-butanol and 55 g (1.2 mole) 99% formic acid is added dropwise over about 3 hours to a mixture of 470 g 96% sulfuric acid and 0.1 mole higher diamondoid dissolved in 100 mL cyclohexane while stirring vigorously at room temperature. After decomposing with ice, the acids are isolated and purified by recrystallization from methanol/water giving the monocarboxylated higher diamondoid.

Via Brominated Higher Diamondoids [D—$(Br)_n$]

Example 27

D—COOH from D—Br 360 mL concentrated sulfuric acid, which has been cooled to +10° C., is placed in a 1-L three-necked flask, which is equipped with a stirrer, a reflux condenser and an Anschütz top with two dropping funnels. After removing the ice bath, while stirring, a suitable monobrominated higher diamondoid D—Br (0.056 mole) dissolved in 25 mL dry, highly pure n-hexane and 25.3 mL anhydrous formic acid is added into the flask in a course of about 1 hour. A fume hood is necessary to remove the carbon monoxide produced. After the dropwise addition has been completed, the mixture is vigorously stirred for about an additional 2 hours at room temperature. Then the reaction mixture is poured onto ice, whereby the acid precipitates out. The acid is purified by dissolution in ether and extraction with dilute sodium hydroxide aqueous solution. The acid which precipitates during the acidification is recrystallized from dilute methanol.

Example 28

D—CHClCOOH from D—Br

A mixture of a suitable monobrominated higher diamondoid D—Br (0.012 mole) and 9.0 g trichloroethylene CHCl=$CCl_2$ is added dropwise in the course of about 4 hours into 24 mL 90% sulfuric acid at 103-106° C. while stirring. After the addition is completed, the mixture is stirred for about an additional 2 hours at the specified-temperature, then cooled down and hydrolyzed with ground ice. The precipitated product can be freed from the neutral fraction by dissolution in dilute sodium hydroxide solution and extraction with ethyl ether. When acidified with dilute hydrochloric acid solution, the carboxylic acid precipitates out of the alkaline solution. Further purification could be achieved by recrystallization from cyclohexane.

Via Hydroxylated Higher Diamondoids [D—$(OH)_n$]

Example 29

D—COOH from D—OH

When a monohydroxylated higher diamondoid D—OH is used, one works in the same way described in Example 31 above except that the amount of n-hexane must be increased to 150 mL because of the lower solubility of the monohydroxalted higher diamondoid in n-hexane.

Example 30

D—$(COOH)_2$ from D—$(OH)_2$

Formic acid (98%, 280 mL) is added dropwise to a stirred solution of a dihydroxylated higher diamondoid D—$(OH)_2$ (0.091 mol) in concentrated sulfuric acid (96%, 1.3 L) at 0° C. The mixture is stirred at 0° C. for 2 hours and at room temperature for 4 hours, and is then poured over ice/water. The resultant product is washed with water and acetone and dried to afford the dicarboxylated higher diamondoid.

Synthesis of Acylaminated Higher Diamondoids [D—$(NHCOR)_n$] (R=H or alkyl, n=1, 2, 3, 4, ...)

Via Brominated Higher Diamondoids [D—$(Br)_n$]

Example 31

D—$NHCOCH_3$ from D—Br

A suitable monobrominated higher diamondoid D—Br (0.093 mole) is dissolved in 150 mL acetonitrile. While stirring, 30 mL concentrated sulfuric acid is slowly added to the above solution, whereby the mixture heats up. After it has been left standing for about 12 hours, the solution is poured into 500 mL ice water, whereby the monoacetamino higher diamondoid separates out.

Via Hydroxylated Higher Diamondoids [D—$(OH)_n$]

Example 32

D—$NHCOCH_3$ from D—OH

A suitable monohydroxylated higher diamondoid D—OH (0.046 mole) is dissolved in 120 mL highly pure glacial acetic acid and treated with 13 mL acetonitrile and 4 mL concentrated sulfuric acid. The reaction mixture is left standing closed for about 20 hours at room temperature, and then twice the volume of water is added to it. After a few hours the precipitated reaction product is filtered off, and after drying it is recrystallized from cyclohexane.

Via Carboxylated Higher Diamondoids [D—($CO_2H$)$_n$]

Example 33

D—$NHCOCH_3$ from D—$CO_2H$

Within 12 minutes, 4.1 g (0.1 mole) acetonitrile and a suitable monocarboxylated higher diamondoid D—COOH (0.018 mole) are added to 20 mL 100% sulfuric acid at room temperature while stirring vigorously. Ice is added after about 1.5-hour post reaction. Then a crystalline precipitate is separated out. The suspension is made basic with sodium hydroxide solution and suctioned over a glass frit. Recrystallization from cyclohexane affords a monoacetaminated higher diamondoid product.

Example 34

D—NHCHO from D—COOH

Within 7 minutes 8.16 g (0.17 mole) sodium cyanide and a suitable monocarboxylated higher diamondoid D—COOH (0.028 mole) are added to 100 mL 100% sulfuric acid while stirring vigorously. After ½ hour, decomposition is carried out by pouring the reaction mixture onto 250 g crushed ice which is then made basic by the addition of a sufficient amount of odium hydroxide solution and extracted five times with benzene/ether. The solvent is removed in vacuo from the combined extracts and the residue is recrystallized from benzene/hexane to afford monoformylaminated higher diamondoid D—NHCHO.

Synthesis of Higher Diamondoidyl Carboxylic Acid Esters [D—($CO_2R$)$_n$] Via Esterification Reaction (R=alkyl, n=1, 2, 3, 4, ...)

Example 35

D—$CO_2CH_2CH_3$ from D—COOH via D—COCl 0.017 mole of a suitable monocarboxylated higher diamondoid D—COOH is mixed with 4.2 g $PCl_5$ in a 50-mL flask with a stirrer and a reflux condenser. The reaction starts after 30-60 seconds with liquefaction of the reaction mixture. The mixture is heated for an additional about 1 hour while stirring on the steam bath. The $POCl_3$ formed is distilled off under vacuum. The acid chloride left behind as a residue is cooled with ice water, and 6.0 mL absolute ethanol is added dropwise. The mixture is heated for an additional around 1 hour on the steam bath and then poured into 50 mL water after it has been cooled down. The ester is taken up with ethyl ether and then washed with potassium carbonate aqueous solution and water. After drying, fractionation is carried out over calcium chloride under vacuum.

Synthesis of Hydroxymethylated Higher Diamondoids [D—($CH_2$—OH)$_n$] Via Reduction of Higher Diamondoidyl Carboxylic Acid Esters [D—($CO_2R$)$_n$] (R=alkyl, n=1, 2, 3, 4, ...)

Example 36

D—$CH_2$—OH from D—$CO_2CH_2CH_3$ 0.014 mole of a suitable higher diamondoid monocarboxylic acid-ethyl ester D—$CO_2CH_2CH_3$ dissolved in 10 mL absolute ether is slowly added dropwise to a suspension of 0.8 g lithium alanate in 16 mL absolute ether while stirring at room temperature. The mixture is stirred for an additional about 1 hour and then water is carefully added. The ether solution is separated out and the aqueous phase is extracted with ether two more times. After the combined extracts have been dried with calcium chloride, the ether is distilled off and the residue is recrystallized from methanol/water.

Synthesis of Aminated Higher Diamondoids [D—($NH_2$)$_n$] (n=1, 2, 3, 4, ...)

Via Alkaline Hydrolysis of Acylaminated Higher Diamondoids [D—(NHCOR)$_n$] (R=alkyl, e.g. $CH_3$)

Example 37

D—$NH_2$ from D—$NHCOCH_3$

A suitable monoacetaminated higher diamondoid D—$NHCOCH_3$ (0.015 mole) is heated to reflux for about 5 hours with a solution of 6 g powdered sodium hydroxide in 60 mL diethylene glycol. After it has been cooled down, the mixture is poured into 150 mL water and extracted with ethyl ether. The ether extract is dried with potassium hydroxide. The ether is distilled off and the residue is sublimated to afford the product monoaminated higher diamondoid. The hydrochloride salt is prepared for analysis. Thus, dry hydrogen chloride is conducted into the ether solution of the amine, whereby the salt separates out as a crystalline compound. It can be purified by dissolving it in absolute ethanol and precipitating with absolute ether.

Example 38

D—$NH_2$ from D—Cl

A suitable monochlorinated higher diamondoid D—Cl is converted by the acetonitrile-sulfuric acid procedure described above to the monoacetaminated higher diamondoid D—$NHCOCH_3$. The crude amide, without prior purification, is saponified to afford a monoaminated higher diamondoid D—$NH_2$. Purification of the amine is as described above.

Example 39

D—$NH_2$ from D—COOH

Step 1: 0.017 mole of a suitable monocarboxylated higher diamondoid D—COOH is mixed with 4.2 g $PCl_5$ in a 50-mL flask with a stirrer and a reflux condenser. The reaction starts after 30-60 seconds with liquefaction of the reaction mixture. The mixture is heated for an additional about 1 hour while stirring on the steam bath. The $POCl_3$ formed is distilled off under vacuum to afford an acid chloride D—COCl.

Step 2: a solution of the above higher diamondoidyl monocarboxylic acid-chloride D—COCl (0.027 mole) in 12 mL absolute tetrahydrofuran is slowly added dropwise to a 60 mL concentrated aqueous ammonia solution while stirring and cooling with ice water. The higher diamondoidyl monocarboxylic acid-amide is separated out as a precipitate. It is suctioned, washed with water and recrystallized from cyclohexane after it has been dried.

Step 3: 0.018 mole of the above amide is dissolved in 25 mL absolute methanol. This solution is added to a solution of 1.0 g sodium in 25 mL absolute methanol, which is located in a 150-mL three-necked flask with a stirrer, a reflux condenser and dropping funnel. Then 1.0 mL bromine is added dropwise with ice cooling, and then the mixture is slowly heated to around 55° C. (water bath temperature). After it has been cooled, water is added and the precipitate is separated out by filtration. Further purification can be achieved by recrystallization from ethanol.

Step 4: the above product is finally saponified and worked up in the same way as described above to afford the target compound.

Via Acid Hydrolysis of Formylaminated Higher Diamondoids [D—(NHCHO)$_n$]

Example 40

D—NH$_2$ from D—Br via D—NHCHO

Step 1: a monobromo higher diamondoid D—Br (0.028 mol) is mixed with 40 mL formamide. The resultant mixture is refluxed for about 12 hours. After cooling, the reaction mixture is poured into water and extracted with dichloromethane. The organic phase is dried with magnesium sulfate, filtered, and evaporated to dryness under vacuum to provide a mono N-formyl higher diamondoid D—NHCHO.

Step 2: the above mono N-formyl higher diamondoid D—NHCHO (0.023 mol) is mixed with 100 mL of 15% hydrochloric acid. The resultant mixture is heated to boiling for about 24 hours. After cooling, the precipitate is filtered and recrystallized from isopropanol to afford the product D—NH$_2$.

Via Reduction of Nitro Higher Diamondoids [D—(NO$_2$)$_n$]

Example 41

D—NH$_2$ from D—NO$_2$

A mixture of 0.412 mmol of a mononitro higher diamondoid D—NO$_2$ and 11.5 g of sodium sulfide nonahydrate in 400 mL of mixed solvent of THF/H$_2$O (3:2 v/v) is vigorously stirred for about 12 hours at 75° C. After cooling to room temperature, the mixture is concentrated below 40° C. under reduced pressure until the volume is reduced to about 15 mL. The precipitate is filtered with suction followed by washing well with water and a 1.0 N HCl aqueous solution. The crude product is dissolved in chloroform or ethyl ether and washed with water (4×80 mL) to neutralize any sodium hydroxide in the organic phase until the material is free from sodium hydroxide and sodium chloride. After removal of the solvent, a crude product is obtained. The separation and purification of the product is carried out on column chromatography on neutral Al$_2$O$_3$ using chloroform/hexane as the eluent. If necessary, purification on column chromatography could be performed several times.

Synthesis of Alkenylated Higher Diamondoids Via Alkylation and Dehydrogen Bromide Reactions

Example 42

D—CH=CH$_2$ from D—Br

Step 1: a solution of a suitable monobrominated higher diamondoid (D—Br) (0.046 mole) in 15 mL n-hexane in a 150-mL three-necked flask equipped with a stirrer, a gas inlet tube and a gas discharge tube with a bubble counter is cooled to −20 to −25° C. in a cooling bath. While stirring one introduces 4.0 g powdered freshly pulverized aluminum bromide of high quality, and ethylene is conducted in such a way that the gas intake can be controlled with the bubble counter. The reaction starts with a slight darkening of the color and is completed after about 1 h. The reaction solution is decanted from the catalyst into a mixture of ether and water. The ether layer is separated off, and the aqueous phase is extracted once more with ether. The combined ether extracts are washed with water and dilute sodium carbonate aqueous solution. After they have been dried over calcium chloride, the ether is distilled off. The residue is separated by distillation under vacuum. An oily liquid is distilled and collected, which solidifies in the receiver. Recrystallizing from methanol affords the higher diamondoidyl ethyl bromide D—CH$_2$CH$_2$Br.

Step 2: a solution of 0.7 g fine powdered potassium hydroxide and the above higher diamondoidyl ethyl bromide D—CH$_2$CH$_2$Br (0.012 mole) in 10 mL diethylene glycol is heated to 220° C. in an oil bath for 6 hours. After cooling down the mixture is diluted with 30 mL water and exacted with ethyl ether. The ether extract is washed twice with water and dried over calcium chloride. The residue left behind after the ether has been distilled off is sublimated in vacuum, and if necessary, the compound can be recrystallized from methanol.

Synthesis of Alkynylated Higher Diamondoids Via Alkylation and Dehydrogen Bromide Reactions

Example 43

D—C≡CH from D—Br

Step 1: in a 150-mL two-necked flask with a stirrer and a drying tube, a mixture of 0.069 mole of a suitable monobromonated higher diamondoid and 20 mL vinyl bromide is cooled to −65° C. in a cooling bath. While stirring, 4.5 g powdered aluminum bromide is added in portions and the mixture is stirred for an additional about 3 hours at the same temperature. Then the reaction mixture is poured into a mixture of 30 mL water and 30 mL ethyl ether. After vigorously stirring, the ether layer is separated and the aqueous layer is extracted once more with ether. The combined ether extracts are washed with water and dilute sodium carbonate solution. After it has been dried with calcium chloride and the solvent has been distilled off, the residue is distilled under vacuum.

Step 2: 15 g powdered potassium hydroxide in 30 mL diethylene glycol is heated to reflux with 0.046 mole of the above product for about 9 hours in the oil bath. Monoethynylated higher diamondoid is formed and may condense in the condenser and must be returned to the reaction mixture from time to time. At the end of the reaction time, the reaction mixture is distilled until no more solid particles go over. The distillate is extracted with ethyl ether and the ether phase is washed with water and dried over calcium chloride. The ether is distilled off and, the residue solidifies. It may be sublimated under vacuum and, if necessary, recrystallized from methanol.

Example 44

D—C≡CH and D—(C≡CH)$_2$ from D—Br

A solution of a monobromo higher diamondoid D—Br (14.2 mmol) and vinyl bromide (5 mL) in CH$_2$Cl$_2$ (25 mL) is cooled with a dry ice-acetone bath (−30° C.). aluminum bromide (4.9 mmol) is added, portionwise, over 30 minutes while the internal temperature is kept below −24° C. the mixture is stirred at −30° C. for 45 min., diluted with CH$_2$Cl$_2$ and solwly poured over crushed ice and concentrated hydrochloric acid (20 mL). The organic layer is separated and the aqueous layer is extracted with CH$_2$Cl$_2$. The combined organic layers are washed with brine, dried and filtered. Solvent is evaporated under reduced pressure to give a viscous oil.

The oil is dissolved in DMSO (50 mL) and potassium t-butoxide (36 mmol) is added over 1 hour. The mixture is stirred at room temperature for 3 days and then heated at 50-55° C. for 3.5 hours. Standard isolation procedure with $CH_2Cl_2$ gives an oil. Distillation provides a semi-solid residue. The residue is chromatographed on silica gel (hexane and 95:5 hexane/$CH_2Cl_2$) to afford the mono-(D—C≡CH) and diethynylated higher diamondoid D—(C≡CH)$_2$.

Synthesis of Higher Diamondoidyl Ethers [D—(OR)$_n$] (n=1, 2, 3, 4, . . . ; R is alkyl, aryl, etc.)

Example 45

D—O—$CH_2$—$C_6H_5$ from D—Br

To a solution of benzyl alcohol $C_6H_5$—$CH_2$—OH (0.28 mole) containing 0.03 mole of sodium benzylate is added 0.01 mole of D—Br and the resulting mixture heated for about 4 hours, during which a copious precipitate NaBr formed. After cooling, the reaction mixture is poured into water and the aqueous phase extracted with ethyl ether and the later dried over sodium sulfate, then evaporated. Most of the benzyl alcohol is removed by distillation, leaving ca. 4 mL of oil which is chromatographed over alumina. Elution with petroleum ether affords the product.

Sequential Reactions of Higher Diamondoidyl Acetic Acid and Their Derivatives

As shown above, the higher diamondoidyl carboxylic acid, e.g. D—COOH, can be conveniently prepared by different methods. The corresponding acid chloride D—COCl is obtained by stirring a mixture of the acid and thioyl chloride diluted with petroleum ether at room temperature for about 50 hours. Treatment of the acid chloride D—COCl with an excess amount of ethereal diazomethane gives the higher diamondoidyl acetyl diazomethane D—$COCHN_2$. Reactions of the acid chloride D—COCl with such amines as ammonia and aniline give the corresponding amides, in those cases D—$CONH_2$ and D—$CONHC_6H_5$ respectively, in good yields.

The Hofmann reaction of D—$CONH_2$ with bromine and alkali affords D—NHCONHC(O)—D via the isocyanate intermediate D—NCO.

The acid chloride D—COCl and hydrazine hydrate hive the corresponding bishydrazide (D—CONH)$_2$, while methyl higher diamondoidylacetate D—$COOCH_3$ and hydrazine hydrate give monohydrazide D—$CONHNH_2$. The lithium aluminum hydride reduction of D—$COOCH_3$ gives D—$CH_2$—OH. Those reactions are summarized in FIG. 20.

Example 46

D—$CONH_2$ from D—COCl

Concentrated aqueous ammonia (11.0 mL) is, over a period of 30 min., stirred, drop by drop, into a stirred solution of D—COCl, prepared from 5.5 mmole of D—COOH, in 4.0 mL of dry THF under cooling with ice-water. The stirring is continued for about 6 hours, and then, the precipitates are filtered out washed with water and dried to give the title compound.

Example 47

Hofmann Reaction of D—$CONH_2$

Into an ice-cooled bromine-alkali reagent, freshly prepared from 1.0 g of bromine, 1.0 g of sodium hydroxide, and 10 mL of water, 0.5 g of D—$CONH_2$ is added and stirred. The temperature is then raised to about 80° C. over a 3.5-h period and kept there for about 10 min. after cooling, separated solids are filtered and washed with water. Recrystallization from chloroform-petroleum ether gives the pure product D—NHCONHC(O)—D.

Example 48

D—CONH—$C_6H_5$ from D—COCl

A mixture of D—COCl, prepared from 2.8 mmole of D—COOH, 0.5 g of aniline, and 20 mL of dry benzene, is refluxed for about 15 min. and cooled. The cooled reaction mixture is washed with 5% hydrochloride acid and then with water, and dried over anhydrous sodium sulfate. After the removal of the solvent, the residue is recrystallized from methanol to give the product D—CONH—$C_6H_5$.

Example 49

(D—CONH)$_2$ from D—COCl

Into an ice-cooled solution of 1.6 g of 80% hydrazine hydrate in 1.0 mL of THF is stirred and stirring is continued for about 7 hours at room temperature. The then the mixture is allowed to stand in a refrigertor overnight. Solids are then filtered and recrystallized from methanol to give the product (D—CONH)$_2$.

Example 50

D—$CON_3$, D—NCO, and D—NHCONH—$C_6H_5$ from D—COCl

Into a solution of D—COCl, prepared from 2.8 mmole of D—COOH, in 2 mL of acetone, a solution of 2.0 g of sodium azide in 5 mL of water is stirred. Stirring is continued for about 2 hours at room temperature. The reaction mixture is then diluted with 15 mL of water and extracted with ethyl ether (2×30 mL). The combined ether extracts are washed with water, dried over anhydrous sodium sulfate, and evaporated to give a compound which by an infrared analysis shows that the rearrangement has already occurred during the procedure. To complete the rearrangement, the crude azide D—$CON_3$ is heated in dry denzene for about 1 hour.

The crude azide D—$CON_3$ is treated with 0.30 mL of aniline in n-hexane at room temperature for about 13 hours. The precipitates are then filtered to give a crude D—NHCONH—$C_6H_5$.

Example 51

D—$CH_2$CONH—$C_6H_5$ from D—COCl via D—$COCHN_2$

A solution of D—COCl, prepared from 2.8 mmole of D—COOH, in 10 mL of ether is added to a solution of diazomethane in 100 mL of ether under ice-water cooling, after which the reaction mixture is allowed to stand for about two days at room temperature. The solvent is stripped off in vacuo, and the residual compound, D—$COCHN_2$, is characterized as having a diazoketone structure on the basis of the infrared absorptions, D—$COCHN_2$ and 0.7 g of aniline are dissolved in 100 mL of anhydrous benzene, and the mixture is irradiated with a 100-W high-pressure mercury lamp through a quartz cooler in a nitrogen stream at room temperature. After about 9 hours' irradiation, the solution is washed successively with 10% hydrochloric acid, 5% sodium hydroxide, and then water. The solution is dried over anhydrous sodium sulfate, and the benzene is distilled off in vacuo. The residue is triturated with 10 mL of n-hexane to give a purer compound. The isolated compound is dissolved in 50 mL of ethanol, and the solution is treated with active charcoal. The solvent is distilled off in vacuo, and the residue is recrystallized from methanol to afford the pure product D—$CH_2$CONH—$C_6H_5$.

Example 52

D—$CH_2$—OH from D—COOH via D—COOCH$_3$

To an etheral solution of diazomethane, a solution of 2.8 mmole of D—COOH in 20 mL of ether is gradually added. The solution is allowed to stand overnight at room temperature, and then the ether is removed in vacuo to give D—COOCH$_3$, which is then dissolved in 50 mL of dry ether, and then 1.1 g of lithium aluminum hydride is added to the solution. The reaction mixture is then stirred overnight at room temperature and diluted with 50 mL of water. The aqueous solution is acidified with concentrated hydrochloric acid and extracted with ether. The ether extract is washed with water and dried over anhydrous sodium sulfate. The ether is removed to give the product D—$CH_2$—OH.

Synthesis of Bi-Higher Diamondoids [e.g. D—D] and Some of Their Derivatives [e.g. R—D—D—R] (R=H, Br, CN, COOH, COCl, COOCH$_3$, $CH_3$OH, $C_6H_4$OCH$_3$, $C_6H_4$OH, $C_6H_5$, $CH_2NH_2$, $CH_2NH_2$HCl, OH, etc.)

Example 53

D—D from D—Br

A suitable monobrominated higher diamondoid D—Br (50 mmole) is dissolved in 30 mL of xylene and heated to reflux in a three-necked flask fitted with thermometer, nitrogen inlet, stirrer, and reflux condenser, under a slow stream of nitrogen. Then a total of 1.15 g of sodium metal is added to the stirred reaction mixture over a period of about 4 hours. After all the sodium has been added, the mixture is refluxed for about an additional hour and then filtered in the hot state. On cooling to room temperature, the product D—D is crystallized from the filtrate.

Example 54

Br—D—D—Br from D—D

D—D (14 mmole) is charged into a round-bottom flask fitted with a reflux condenser. Then 20 mL of bromine is added with stirring, and hydrogen bromide is formed. Hydrobromic acid evolution ceases after about 15 min. The reaction mixture is then heated to reflux (ca. 61° C. pot temperature) for about 2 hours. The cooled reaction product is diluted with 75 mL of $CCl_4$ and transferred to a separatory funnel, shaken with ice-water, and sodium bisulfite is added until excess bromine is destroyed. The organic layer is separated and the water layer is extracted twice with 50 mL of $CCl_4$. The combined organic solution is dried over sodium sulfate and the solvent is tripped under slight vacuum. The reaction product in the pot is precipitated with methanol, filtered off, and recrystallized from dioxane to give Br—D—D—Br product.

Example 55

NC—D—D—CN from Br—D—D—Br

To 15 g of cuprous cyanide charged into a round-bottom flask fitted with a distilling bead, thermometer, and stirrer, 75 mL of pyridine is added. To the pyridine-copper cyanide complex which has formed immediately, Br—D—D—Br (46 mmole) is added and the reaction mixture heated slowly to about 230° C., whereby most of the pyridine distilled. The reaction product is maintained at the above temperature for an additional 10 min. after cooling to room temperature, a crude product is collected which is purified by recrystallization from benzene to give a pure product NC—D—D—CN.

Example 56

HOOC—D—D—COOH from NC—D—D—CN

To 6.5 mmole of NC—D—D—CN is added a mixture of 15 mL of concentrated sulfuric acid, 15 mL of glacial acetic acid, and 15 mL of water. The mixture is then heated to reflux for about 1.5 hours (about 125° C. pot temperature) with stirring. The reaction product is filtered off, carefully washed with water and methanol, and then dried. Recrystallization from dimethylacetamide affords the pure product HOOC—D—D—COOH.

Example 57

$CH_3OC_6H_4$—D—D—$C_6H_4OCH_3$ from Br—D—D—Br

To Br—D—D—Br (11.5 mmole) is added 25 mL of anisole and the mixture is heated to reflux (about 155° C. pot temperature) for about 5 hours. After about 15 minutes refluxing, hydrogen bromide is evolved. The evolution of hydrogen bromide ceases after about 1 hour. The reaction product is filtered hot and on cooling to room temperature, a crude product is collected which is then recrystallized from xylene to give the pure product $CH_3OC_6H_4$—D—D—$C_6H_4OCH_3$.

Example 58

HClH$_2$NCH$_2$—D—D—$CH_2NH_2$HCl and H$_2$NCH$_2$—D—D—$CH_2NH_2$ from NC—D—D—CN Powdered lithium aluminum hydride (0.6 g) is charged into a three-neck flask fitted with a thermometer, nitrogen inlet, addition funnel, and reflux condenser together with 15 mL of anhydrous THF. A solution of NC—D—D—CN (7.8 mmole) in 20 mL of anhydrous THF is added over a period of about 20 min. the reaction product, after cooling to room temperature, is poured onto ice containing dilute hydrochloric acid. Recrystallization from dilute hydrochloric acid gives the dihydrochloride product HClH$_2$NCH$_2$—D—D—$CH_2NH_2$HCl. The free diamine H$_2$NCH$_2$—D—D—$CH_2NH_2$ is obtained from the dihydrochloride by reaction with ammonia.

Synthesis of Azido Higher Diamondoids [D—($N_3$)$_n$] (n=1, 2, 3, 4, . . . )

Direct substitution of brominated higher diamondoids with NaN$_3$ results in the formation of azido higher diamondoids, which are very good precursors of higher diamondoidylnitrenes. The azido derivative, e.g. D—$N_3$, is reduced by lithium aluminium hydride in ether to give the corresponding amine, e.g. D—$NH_2$.

Example 59

D—$N_3$ from D—Br

A mixture of D—Br (2 mmole) and sodium azide (1.3 g) in dry dimethyl sulfoxide (DMF, 20 mL) is heated with stirring at 100° C. for about two days. The mixture is poured onto ice-water to give a precipitate which can be purified by recrystallization from aqueous methanol to give the pure product.

Synthesis of N—R-Sulfonyl-N'-Higher Diamondoidyl Ureas (e.g. R—SO$_2$NHCONH—D, R=alkyl, aryl, alkaryl, etc.)

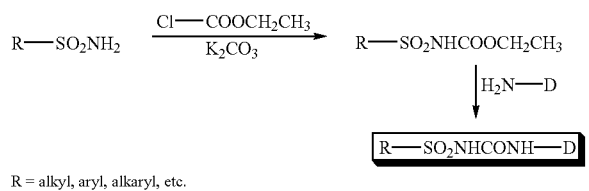

R = alkyl, aryl, alkaryl, etc.

Example 60

Aryl-SO$_2$NH$_2$ from Aryl-SO$_2$—Cl

Aryl-SO$_2$NH$_2$ (arylsulfonamide) is prepared by addition of Aryl-SO$_2$—Cl (arylsulfonyl chloride) to a large excess of aqueous ammonium hydroxide. It is better to dissolve the solid sulfonyl chlorides in a volume of dioxane equal to their weight.

Example 61

Aryl-SO$_2$NHCOOCH$_2$CH$_3$ from Aryl-SO$_2$NH$_2$

To a mixture of 0.5 mole of the sulfonamide Aryl-SO$_2$NH$_2$ and 1.3 moles of anhydrous potassium carbonate in 600 mL of acetone is added, during about 3 hours, with stirring, 0.66 mole of ethyl chlorocarbonate Cl—COOCH$_2$CH$_3$. The mixture is then stirred and refluxed for about 18 hours, then allowed to cool, and filtered. The solid residue is dissolved in about 1500 mL of water. Any insoluble material is removed by filtration. The solution is acidified with concentrated hydrochloride acid. If the product does not crystallize readily, decantation of the acidic supernatant liquid and stirring the carbamate with water promotes the crystallization. The crude product Aryl-SO$_2$NHCOOCH$_2$CH$_3$ (ethyl N-arylsulfonylcarbamate) is used for reaction with a suitable amine, e.g. D—NH$_2$.

Example 62

Aryl-SO$_2$NHCO—NHD from Aryl-SO$_2$NHCOOCH$_2$CH$_3$ and D—NH$_2$

A solution of 2 mmoles of D—NH$_2$ and 2.2 mmoles of aryl-SO$_2$NHCOOCH$_2$CH$_3$ (ethyl N-arylsulfonylcarbamate) in about 10 mL of dry toluene is heated to reflux for about 5 hours. The reaction mixture is allowed to cool to room temperature, and the product is collected by filtration and then dissolved in chloroform (the chloroform should not contain any trace amount of ethanol by shaking with alumina). The chloroform solution is washed with cold 5% hydrochloric acid solution, then with water until neutral, and dried over anhydrous magnesium sulfate. The chloroform solution is then concentrated under reduced pressure to about one-half its volume, warmed to about 50° C. Petroleum ether is added. After chilling the mixture overnight, the product aryl-SO$_2$NHCO—NHD (N-arylsulfonyl-N'-higher diamondoidyl urea) is collected by filtration.

Synthesis of Higher Diamondoidyl Chloroformates [D—(OCOCl)$_n$] (n=1, 2, 3, 4, . . . ) and the Subsequent Reactions and Derivatives [e.g. D—OCONH$_2$, D—OCO—NHNH$_2$, etc.]

Higher diamondoidyl chloroformates, e.g. D—OCOCl, are prepared from hydroxylated higher diamondoids, e.g. D—OH, and excess phosgene (COCl$_2$) in a suitable solvent, e.g. benzene, in the presence of an organic base, e.g. pyridine. The chloroformate is able to react with different nucleophiles, e.g. ammonia, hydrazine (H$_2$NNH$_2$), amines, amino acids, alcohols, thiols, etc., to give the corresponding higher diamondoidyloxycarbonyl derivatives, e.g. D—OCONH$_2$, D—OCONHNH$_2$, etc. The higher diamondoidyloxycarbonylamino acids, in turn, are readily cleaved by acid-catalyzed solvolysis with, e.g. trifluoroacetic acid to yield the free amino acids. In those cases, the higher diamondoidyloxycarbonyl group.

Example 63

D—OCOCl from D—OH

To a solution of liquid phosgene (COCl$_2$, 30 g) in anhydrous benzene (100 mL), a solution of D—OH (53 mmoles) and pyridine (7 g) in benzene (200 mL) is added dropwise and with stirring over a 1-h period, while maintaining the reaction temperature at about 4° C.

The reaction mixture is filtered and the filtrate is poured into ice water and shaken in a separatory funnel. The organic layer is dried with sodium sulfate and concentrated to about one-fifth of its original volume under reduced pressure at room temperature.

When a sample of the concentrate is evaporated to dryness at room temperature, the solid is obtained. Recrystallization from anhydrous petroleum may give crystals of the product.

Example 64

D—OCONHNH$_2$ from D—OCOCl and H$_2$NNH$_2$

A solution of D—OCOCl (9.3 mmoles) in anhydrous benzene (150 mL) is added slowly to a stirred solution of anhydrous hydrazine (2.5 g) in t-butyl alcohol (20 mL). After stirring for about 2 hours, the solvent is removed in vacuo. The residue is dissolved in a mixture of ether (150 mL) and water (10 mL). The ether layer is washed with 35 mL portions of water, 5 mL of 1% sodium carbonate solution, and 5 mL of water, and dried. Anhydrous hexane (10 mL) is added and the solution is concentrated to about 10 mL. Cooling the solution at about −10° C. gives the product D—OCONHNH$_2$.

Example 65

D—OCONH$_2$ from D—OCOCl

A solution of D—OCOCl (0.5 mmole) in anhydrous benzene (25 mL) is saturated with gaseous ammonia (ca. 1 hour). The flask is stoppered and maintained at ambient temperature for about 24 hours. The reaction mixture is filtered, and the filtrate is shaken with ice water and evaporated in vacuo to yield the product. Purification may be recrystallized from anhydrous ethanol.

Example 66

Higher Diamondoidyloxycarbonyl Amino Acids from D—OCOCl and Amino Acids

A suitable amino acid (5 mmoles) is suspended in water (about 20 mL). The mixture is stirred and cooled in an ice bath. Sodium hydroxide (1N, 5 mL) is added whereupon the amino acid usually dissolved. To this mixture, 0.8 g sodium carbonate (7.5 mmoles) is added. From a solution of D—OCOCl, the solvent is removed in vacuo on a flash evaporator at a bath temperature of about 30° C. To the residue which may be oily or semisolid, dry petroleum ether is added and removed in vacuo. This is repeated once more to remove traces of phosgene which may be left in the preparation of the chloroformate. The residue is dissolved in anhydrous dioxane (5 mL) and added to the solution of the amino acid over a period of about 1 hour with continued stirring and cooling. Since some solid may precipitate, ether is added (5 mL) after the first and last addition of the chloroformate. After stirring in ice for about 2 hours, the solution is extracted three times with ether or ethyl acetate, and under stirring and cooling acidified with 85% phosphoric acid or 10% sulfuric acid to a pH of about 2. The precipitated product is extracted into the organic layer and the aqueous phase is extracted with two more portions of fresh organic solvent. The combined extracts are dried over sodium sulfate and the solvent is removed in vacuo. The residue is recrystallized from a suitable solvent, e.g. ether-petroleum ether, ethyl acetate, ethyl acetate-petroleum ether.

Synthesis of Hydrazino Higher Diamondoids [e.g. D—(NH—NH$_2$)$_n$] Starting from Aminated Higher Diamondoids [e.g. D—(NH$_2$)$_n$] (n=1, 2, 3, 4, . . . )

D—(NH$_2$)$_n$ and D—(CONH$_2$)$_n$ (n=1, 2, 3, 4, . . . ) are very important precursors for the synthesis of a variety of higher diamondoid derivatives. Some representative pathways for such a derivatization of higher diamondoids starting from D—NH$_2$ and D—CONH$_2$ are shown in FIG. 18.

Example 67

D—NH—CH$_2$—CN from D—NH$_2$ 40.5 mmoles of monoamino higher diamondoid hydrochloride (D—NH$_2$HCl) is dissolved in 80 mL water, then 3.2 g aqueous CH$_2$O solution (37-40%) is added with stirring at room temperature. While stirring at room temperature, to the above mixture is added dropwise a solution of 2.6 g potassium cyanide (KCN) in 20 mL water. A solid precipitate is formed and the mixture is stirred over night. Usual workup by extracting the reaction mixture with chloroform and evaporating the solvent gives a crude product of D—NH—CH$_2$—CN (N-higher diamondoidyl aminoacetonitrile) and directly used for the next reaction without purification. Recrystallization from a little mixture of ethyl ether/light petroleum ether gives a pure sample for analysis.

Example 68

D—NH—CH$_2$—COOH from D—NH—CH$_2$—CN

About 40 mmoles of the above crude product of D—NH—CH$_2$—CN is mixed with 50 mL water, 50 mL glacial acetic acid and 50 mL concentrated hydrochloric acid and then the mixture is heated to reflux. A reaction solution (part A) and a crystalline sublimate (part B) formed in the reflux condenser are obtained.

Part A: after the reaction has lasted for about 6 hours, all the solvent is removed under vacuum until a dry residue is obtained, which is used directly for the next reaction. The product D—NH—CH$_2$—COOH can be easily isolated by dissolving the dry residue in water and adjusting the pH to 4.

Part B: the sublimate is dissolved in chloroform, dried, and the solvent evaporated to give, after recrystallizing from isopropanol and sublimating, a pure D—Cl as a major by-product.

Example 69

D—N(NO)—CH$_2$—COOH from D—NH—CH$_2$—COOH

The above crude product of D—NH—CH$_2$—COOH is dissolved in 100 mL 2 N hydrochloric acid and a solution of 5 g sodium nitrite (NaNO$_2$) in 20 mL water is added slowly drop by drop while stirring at room temperature. Solids precipitate and filtered out after the solution has been standing over night, washed well with water and dried to afford the product of D—N(NO)—CH$_2$—COOH.

Example 70

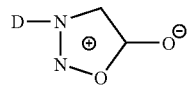

from D—N(NO)—CH$_2$—COOH 11.5 mmoles of D—N(NO)—CH$_2$—COOH are treated with 25 mL of (CF$_3$CO)$_2$O. The solution is warmed up slightly after the treatment. After standing for about 1 hour at room temperature, the solvent is removed under vacuum. The residue is then extracted with chloroform and washed well with 10% aqueous sodium bicarbonate solution. Evaporating the chloroform solvent affords a crude product. Recrystallization from methanol gives the product.

Example 71

D—NH—NH$_2$ from

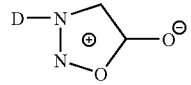

A suspension of about 39 mmoles of the above product in a mixture of 150 mL alcohol and 100 mL concentrated hydrochloric acid is heated on an oil bath to reflux for 15 min. The solution is refluxed for an additional around 45 minutes and then concentrated by evaporation. The residue is recrystallized from about 130 mL isopropanol to afford D—NH—NH$_2$HCl (monohydrazino higher diamondoid hydrochloride).

To produce the HCl free product D—NH—NH$_2$, the hydrochloride product is dissolved in water and a little saturated potassium carbonate solution is then added. A precipitate is filtered out with suction. Recrystallization from ether gives a pure product of D—NH—NH$_2$.

Synthesis of Higher Diamondoidyl Phosphonic Acid Dichlorides [e.g. D—(POCl$_2$)$_n$] and Subsequent Reactions and Derivatives Thereof (n=1, 2, 3, 4, ...)

FIG. 19 presents some representative pathways for the synthesis of a higher diamondoidyl phosphonic acid dichloride (e.g. D—POCl$_2$) and its subsequent reactions and the corresponding derivatives, such as D—PH$_2$, D—PO(OH)$_2$, and so on.

Example 72

D—POCl$_2$ from D—Br 0.1 mole of D—Br, 40 g (0.15 mol) of AlBr$_3$ and 200 mL of PCl$_3$ are heated for about 5 hours under reflux while being stirred. After cooling down and filtration, the residue is washed with 100 mL of benzene, suspended in 300 mL of CCl$_4$ and decomposed carefully with water while cooling with ice. The organic phase is separated out, washed with water, dried over CaCl$_2$ and concentrated in vacuum. Separation and purification of the product D—POCl$_2$ can be conducted by distilling the residue and recrystallization from acetone.

Example 73

D—PO(OH)$_2$ from D—POCl$_2$

Method A: 20 mmoles of D—POCl$_2$ is heated for about 6 hours with 100 mL water under reflux. The aqueous solution is filtered after cooling, and the residue is recrystallized from glacial acetic acid affording the product D—PO(OH)$_2$.

Method B: 0.1 mole of D—POCl$_2$ in 100 mL ethanol is treated with 200 mL concentrated hydrochloric acid and heated for about 5 hours under reflux. After cooling and filtration, the residue is recrystallized several times from glacial acetic acid to give a pure product of D—PO(OH)$_2$.

Example 74

D—PH$_2$ from D—POCl$_2$ via Reduction Reaction with LiAlH$_4$

Under nitrogen a solution of 0.1 mole of D—POCl$_2$ in 150 mL absolute ether is added dropwise over a period of about 2 hours to a suspension of 7 g LiAlH$_4$ in 400 mL absolute ether. After the addition, the mixture is stirred for an additional 1 hour under reflux. The excess LiAlH$_4$ is destroyed by adding about 200 mL dilute hydrochloric acid. The organic phase is separated out, washed with water, dried over MgSO$_4$ and concentrated under nitrogen. The residue is fractionated under nitrogen in vacuum to give the product D—PH$_2$.

Example 75

D—P(OH)$_2$ from D—PH$_2$ via Oxidation Reaction with H$_2$O$_2$

About 50 mmoles of D—PH$_2$ is heated carefully at approximately 50° C. with 50 mL of 30% hydrogen peroxide (H$_2$O$_2$) until the reaction starts. Then the reaction mixture is diluted to one and half with water, boiled briefly and filtered in hot. After cooling down it is possible to isolate some of the product D—P(OH)$_2$. The residue is extracted with CHCl$_3$ and then recrystallized from glacial acetic acid to give some additional amount of the product.

Example 76

D—PCl$_2$ from D—P(OH)$_2$ 0.05 mole of D—P(OH)$_2$ to 75 mL of PCl$_3$ within 10 minutes. After the addition, the reaction mixture is stirred for an additional 5 minutes. The phosphoric acid produced is separated out and the residue is concentrated under vacuum and distilled to give the product D—PCl$_2$. Purification can be carried out by sublimating several times to give a pure sample for analysis.

Example 77

D—P(OH)$_2$ from D—PCl$_2$ 0.01 mole of D—PCl$_2$ is stirred in 50 mL water for about 10 hours at room temperature. Then the mixture is filtered and the residue is recrystallized several times from acetonitrile to yield the product D—P(OH)$_2$.

Sulfur Containing Derivatives Directly Substituted on the Higher Diamondoids

Sulfur containing derivatives such as D—SOCl (higher diamondoidyl sulfinic acid chloride) are prepared by direct substitution on the higher diamondoids with SOCl$_2$ in the presence of AlCl$_3$ at low temperatures. By way of those higher diamondoidyl sulfinic acid chlorides, a variety of sulfur containing derivatives directly substituted on the higher diamondoids are prepared. FIG. 20 presents some representative pathways to derivatize the higher diamondoids via D—SOCl, D—SH, D—SO$_2$H, and D—SO$_2$Cl.

Example 78

D—SOCl from D 40 g (0.3 mole) of AlCl$_3$ and 200 mL of SOCl$_2$ are reacted at about −15° C. for about 2 hours with 0.3 mole of a higher diamondoid. The mixture is stirred for an additional 1 hour at this temperature. Then the clear solution is allowed to warm to room temperature, and the excess SOCl$_2$ is removed under vacuum. The residue is taken up in 300 mL of CCl$_4$ and carefully decomposed with water. The organic phase is separated out, washed with water, dried over CaCl$_2$ and concentrated in vacuum. The residue is distilled to give the product D—SOCl.

Example 79

Higher Diamondoidyl Sulfinic Acid Esters [e.g. D—SO$_2$CH$_3$] from D—SOCl 0.1 mole of D—SOCl is heated under reflux for about 6 hours with 200 mL of absolute methanol. The solvent is then removed in vacuum and the residue is distilled to give the product. For further purification can be carried out by sublimation under vacuum.

Example 80

D—SH from D—SO$_2$CH$_3$ via Reduction Reaction with LiAlH$_4$ 0.1 mole of LiAlH$_4$ is suspended in 100 mL of absolute ether and heated under reflux for about 1 hour. Then a solution of 0.02 mole of D—SO$_2$CH$_3$ in 100 mL of absolute ether is added dropwise over a period of about 2 hours. After about additional 17 hours of stirring under reflux, the excess LiAlH$_4$ is decomposed with a saturated Na$_2$SO$_4$ solution, and the ether phase is separated out after 100 mL of concentrated hydrochloric acid has been added. The aqueous phase is washed for an additional two times with ether. The extracts are combined and dried over $CaCl_2$ and concentrated under vacuum. The residue is sublimated to give D—SH.

Example 81

D—$SO_2H$ (Higher Diamondoidyl Sulfinic Acid) from D—SOCl

To 650 mL 5% sodium hydroxide solution is added about 0.25 mole of D—SOCl (crude product) at room temperature. After about 5 hours of stirring, the temperature is increased to about 50° C., then filtration. Chlorination products remain as residue. The filtrate is acidified with concentrated hydrochloric acid while cooling with ice, and extracted several times with ether. The combined extracts are washed with water, dried over $MgSO_4$ and concentrated to a dry product. Recrystallization from acetonitrile gives product D—$SO_2H$.

Example 82

D—$SO_3H$ (Higher Diamondoidyl Sulfonic Acid) from D—$SO_2H$ (Higher Diamondoidyl Sulfinic Acid) Via Oxidation Reaction with $H_2O_2$ 5 mmoles of D—$SO_2H$ is suspended in 25 mL water while adding 1 mL 30% hydrogen peroxide. Then the mixture is heated while stirring on a water bath and an additional 3 mL 30% hydrogen peroxide are added dropwise within 30 minutes. The solution is briefly boiled, filtered and concentrated under vacuum to dryness at about 30° C. to give the higher diamondoidyl sulfonic acid monohydrate D—$SO_3H$ $H_2O$.

Example 83

D—$SC_2H_5$ from D—SH 0.1 mole of D—SH dissolved in 100 mL ethanol is added while stirring into a solution of 8 g (0.2 mole) of NaOH in 200 mL water and treated for about 1 hour at 50° C. with 15.4 g (0.1 mole) of diethylsulfate. After an additional 1 hour stirring under reflux, the reaction mixture is cooled down and extracted several times with ether. The combined extracts are concentrated in vacuum and the residue is distilled over $CaCl_2$ to give the product D—$SC_2H_5$.

Example 84

D—$SO_2C_2H_5$ from D—$SC_2H_5$ Via Oxidation Reaction with $H_2O_2$ 0.05 mole of D—$SC_2H_5$ in 100 mL glacial acetic acid is heated to reflux with 17.5 g (0.15 mole) 30% hydrogen peroxide. After about 1 hour of stirring under reflux, the reaction mixture is poured onto ice and filtered. Recrystallization from ethanol/water gives the product D—$SO_2C_2H_5$.

Example 85

D—$SO_2H$ from D—$SO_2C_2H_5$ 0.02 mole of D—$SO_2C_2H_5$ and 12 g KOH are heated to 250° C. with 3-5 drops of water. Then the temperature is raised to 275° C. in the course of about 45 minutes, whereby a strong development of a gas takes place. After cooling down, the mixture is dissolved in a little water, acidified with concentrated hydrochloric acid while cooling with ice and extracted several times with ether. The distillation residue from the ether extract gives, after recrystallization from acetonitrile, product D—$SO_2H$.

Example 86

D—SOCl from D—$SO_2H$ 0.05 mole of D—$SO_2H$ is left standing over night with 100 mL freshly distilled $SOCl_2$ at room temperature. The excess $SOCl_2$ is removed under vacuum, and the residue is distilled, whereby the product D—SOCl solidifies in the receiver.

Example 87

Higher Diamondoidyl Sulfinic Acid Esters [e.g. D—$SO_2C_2H_5$] from D—SOCl 0.1 mole of D—SOCl together with 200-300 mL absolute alcohol and 7.9 g (0.1 mole) pyridine is heated for 8-12 h under reflux. The excess alcohol is then removed in vacuum and the residue is mixed with ether. The ether solution is washed twice with dilute hydrochloric acid and water, dried over $MgSO_4$ and concentrated. The residue is distilled in vacuum to give the corresponding ester.

Example 88

Higher Diamondoidyl Sulfinic Acid Amides [e.g. D—$SONH_2$ or D—$SON(CH_3)_2$] from D—SOCl 45 mmoles of D—SOCl is heated with 300 mL 25% aqueous ammonia or 150 mL 40% aqueous dimethylamine for about 2 hours while stirring under reflux. Then the reaction mixture is concentrated to dryness in vacuum and the residue is extracted with ether. The distillation residue from the ether extract is recrystallized from cyclohexane to afford the corresponding amide.

Example 89

D—$SO_2Cl$ (Higher Diamondoidyl Sulfonic Acid Chloride) from D—$SO_2H$

Into a clear solution of 0.05 mole D—$SO_2H$ and 2 g (0.05 mole) NaOH in 200 mL water is introduced a strong chlorine gas flow at approximately 5° C. temperature increase within 45 minutes. After filtration, the residue is extracted in ether. The ether solution is washed chlorine-free with $NaHSO_3$ solution, dried over $MgSO_4$ and concentrated to dryness in vacuum at room temperature. Recrystallization from ethanol gives the product D—$SO_2Cl$.

Example 90

D—SH from D—$SO_2Cl$ Via Reduction Reaction with $LiAlH_4$ 0.01 mole D—$SO_2Cl$ in 100 mL absolute ether is added dropwise within 1 hour to a suspension of 3 g $LiAlH_4$ in 100 mL absolute ether. After the addition, the reaction mixture is stirred for about 3 hours under reflux, then the excess $LiAlH_4$ is destroyed with dilute hydrochloric acid. The organic phase is separated out, dried over $MgSO_4$ and concentrated. The residue is sublimated several times to give D—SH.

Example 91

D—SO$_2$H from D—SO$_2$Cl 10 mmoles D—SO$_2$Cl and 100 mL 10% sodium hydroxide solution are heated on a water bath for about 4 hours while adding 1 g pyridine. After cooling and filtration, the filtrate is acidified with concentrated hydrochloric acid and perforated over night with ether. The ether extract is dried over MgSO$_4$ and concentrated to yield D—SO$_2$H.

Example 92

D—Cl from D—SO$_2$Cl 20 mmoles D—SO$_2$Cl together with 30 mL absolute methanol and 3 g pyridine is heated for about 4 hours at 50° C. while stirring. Then the reaction mixture is poured on ice and extracted with ether. The ether solution is washed with dilute hydrochloric acid, dried over MgSO$_4$ and concentrated. The residue is sublimated to give D—Cl.

Example 93

D—OH from D—SO$_2$Cl 10 mmoles D—SO$_2$Cl and 100 mL 25% aqueous ammonia are heated on a water bath for about 3 hours while stirring. The solution is concentrated in vacuum to dryness, and the residue is sublimated to give D—OH.

Example 94

Higher Diamondoidyl Sulfonic Acid Esters and Amides [e.g. D—SO$_2$OC$_2$H$_5$ and D—SO$_2$N(CH$_3$)$_2$] from the Corresponding Sulfinic Acid Esters and Amides [e.g. D—SO$_2$C$_2$H$_5$ and D—SON(CH$_3$)$_2$] Via Oxidation Reaction with KMnO$_4$ 0.02 mole of the corresponding higher diamondoidyl sulfinic acid ester or amide is treated in 150-400 mL acetone at reflux with a saturated solution of KMnO$_4$ in acetone. After 30 minutes of stirring under reflux, the reaction mixture is filtered from MnO$_2$ and the residue is extracted several times with acetone. The combined filtrates are then concentrated in vacuum to give the corresponding higher diamondoidyl sulfonic acid esters or amides.

Example 95

Formulations

The following are representative pharmaceutical formulations containing a compound of formula I.

Tablet Formulation

The following ingredients are mixed intimately and pressed into single scored tablets.

| Ingredient | Quantity per tablet mg |
|---|---|
| compound of this invention | 400 |
| corn starch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| compound of this invention | 0.4 mg |
| sodium acetate buffer solution | 0.4 M 2.0 ml |
| HCl (1N) or NaOH (1N) | q.s. to suitable pH |
| water (distilled, sterile) | q.s. to 20 ml |

Testing

In testing, the MT-2 cell line, a human T-cell leukemia line derived from isolated cord blood lymphocytes cocultured with cells from patients with adult T-cell leukemia, may be useful. The MT-2 cell line may be obtained from AIDS Research and Reference Reagent Programme of the NIAID, NIH (cat. no. 237, NIH, Bethesda, Md.). The MT-2 cell line can be successfully used as targets for HIV-1 infection and requires only 4 to 5 days for complete cytopathic effect (CPE). (Montefiori et al., J. Clin. Microbiol 1988, 26, 231-235; Pauwels et al., J. Virol. Meth. 1988, 20, 309-321; Harada et al., Science 1985, 229, 563-6)

The MT-2 cell line may be grown and maintained in RPMI 1640 containing 10% fetal calf serum and antibiotics.

Also in testing, the MN/H9 (HIV-1.sub.MN) (cat. no. 317) virus and VP6 may be used. The MN/H9 may be obtained from the AIDS repository. The AZT resistant strain (AZTR) of HIV-1 (cat. no. 629), which was isolated from an AIDS patient and developed by Douglas Richman, may also be used. The AZT resistant strain of HIV-1 may also obtained from the AIDS repository. (Larder et al., Science, 1989, 243, 1731-1734). VP6 is a primary HIV isolate obtained by culturing PBMC from a patient with full blown AIDS and kaposi sarcoma with normal phytohemagglutinin (PHA) stimulated PBMC.

Virus-infected cells may be grown in RPMI 1640 medium, supplemented with 10% fetal bovine serum and 10% interleukin-2. Cell-free supernatant fluid may be collected when the cultures showed peak infectivity titer and may be used as the virus stock. AZTR and VP6 stocks may be grown in MT-2 cells. MN may be grown in H9 cells. The cell free virus stocks may be prepared as per the standard (HIV Research Protocol). The virus stocks may be titrated by tissue culture infective dose (50%) $TCID_{50}$ by inoculating tissue culture and determining observable effects in 50% of the cultures per Reed and Muench, Amer. J. Hyg., 1938, 27, 493-7.

Cytotoxicity Assay

An effective anti-viral drug must be non-toxic to cells. Any antiviral assays must first confirm the testing candidate is not cytotoxic to the cells used in the assay. Because viruses use cellular machinery for replication, cytotoxic compounds would inhibit viruses by definition. The microliter cytotoxicity assay used may based on the ability of living cells to reduce the tetrazolium salt MTT (3[4,5-dimethylthiazol-2-yl]-2,5-diphenyltetrazolium bromide) and form a blue product (Tada, H, et al., J. Immuno. Meth. 1986 93, 157-165; Carmichael et al., Cancer Research 1987, 47, 936). Precisely, when the MT-2 cells are in log phase and $2 \times 10^4$ cells are distributed in each well along with separate 100 µl aliquots of diluted compounds to be tested. The test compounds are soluble in ethyl alcohol (EtOH). Ethanol and medium are incubated in some wells with the cells as an ethanol control. A cell control is also included (wells containing only cells and medium). The plates are incubated for 5 days at 37° C. in 5% $CO_2$ and humidified conditions. Cell viability is determined in each well by the MTT assay. The $OD_{570}$ (optical density at 570 nm) of cells without test compound is taken as 0% killing and is compared to the $OD_{570}$ of cells with test compound. The toxicity profile for different compounds is then scored. In the MTT dye reduction assay, toxicity is indicated as yellow in the wells, with blue color indicating the compound is non-toxic.

The toxicity of the test compounds is tested at concentrations up to 500 g/mi.

Anti-HIV Assay

Stock solutions of different test compounds are appropriately diluted to give final concentration of 2.5, 5, 10 and 20 µg/ml in RPMI medium when 100 µl of each dilution is added to three replicate wells in 96-well flatbottomed microtiter plates. MT-2 cells are inoculated with 100 TCID 50 of HIV-1/MN, the AZT resistant isolate or the VP6 isolate in Ti-25 flasks and are incubated for two hours at 37° C. The cells are then washed to remove any remaining free virus, and $2 \times 10^4$ cells are distributed to each of the wells. In cell control only, uninfected cells are distributed. Virus control wells have only infected cells and medium. The plates are incubated at 37° C. for 5 days. HIV-1 induced syncytia are observed after 48 hours. Pictures may be taken. After day 5, when maximum CPE is observed in virus control wells, the MTT assay is performed and percent protection is calculated for each test compound by applying the following formula:

$$\frac{(OD\tau)HIV - (ODc)HIV}{(ODc)mock - (ODc)HIV}(\%)$$

in which $(OD_\tau)HIV$ is the optical density measured in HIV-infected cells treated with a given concentration of the test compound; $(OD_c)HIV$ is the optical density measured for the control untreated HIV-infected cells. $(OD_c)mock$ is the optical density measured for the control untreated mock infected cells. All O.D. values are determined at 570 nm. For pretreatment experiments, cells are incubated with test compounds for 1 hour at 37° C. prior to infection with the virus. After the adsorption of virus, these cells are washed, the wells replenished with medium containing test compound. The remaining part of the assay is continued as above. Pictures may be taken on day 5. The percent protection from these tests may be plotted.

Virus Neutralization Assay

50 µl of cell free virus (100 TCID50) are mixed with 50 µl of different concentrations of test compounds. Virus-compound mixtures are incubated at 37° C. for 1 hour, then are added to the wells of a 96-well flat-bottomed microtiter plate containing $6 \times 10^4$ MT-2 cells/well. The plates are incubated at 37° C. in 5% $CO_2$ humidified atmosphere for 5 days. MTT reduction assay is performed on day 5. The neutralization pattern is assessed.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. A composition comprising at least 10% by weight of functionalized higher diamondoids having at least one functional group and having the following Formula I:

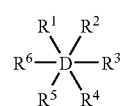

I wherein

D is a higher diamondoid nucleus with the higher diamondoid being selected from the group consisting of substituted and unsubstituted tetramantanes; substituted and unsubstituted pentamantanes; substituted and unsubstituted hexamantanes; substituted and unsubstituted heptamantanes; substituted and unsubstituted octamantanes; substituted and unsubstituted nonamantanes; substituted and unsubstituted decamantanes; substituted and unsubstituted undecamantanes; and mixtures, isomers and stereoisomers thereof; and $R^1$, $R^2$, $R^3$, $R^4$, $R^5$ and $R^6$ are each independently selected from a group consisting of hydrogen, halo, thio, oxide, hydroxyl, nitro, sulfonylhalide, sulfonate, phosphine, added alkyl, alkenyl, alkynyl and aryl, with or without substitution; provided that there is at least one functional group.

2. The functionalized higher diamondoid composition of claim 1 wherein one of $R^1$, $R^2$, $R^3$, $R^4$, $R^5$ and $R^6$ is selected from the group consisting of halo, thio, oxide, hydroxyl, nitro, sulfonylhalide, sulfonate, phosphine, added alkyl, alkenyl, alkynyl and aryl, with or without substitution and the remaining are hydrogen in the higher diamdondoids.

3. The functionalized higher diamondoid composition of claim 1 wherein one at least two of $R^1$, $R^2$, $R^3$, $R^4$, $R^5$ and $R^6$ are selected from the group consisting of halo, thio, oxide, hydroxyl, nitro, sulfonylhalide, sulfonate, phosphine, added alkyl, alkenyl, alkynyl and aryl, with or without substitution and the remaining are hydrogen in the higher diamondoids.

4. The functionalized higher diamondoid composition of claim 3 wherein two of $R^1$, $R^2$, $R^3$, $R^4$, $R^5$ and $R^6$ that are not hydrogen are the same in the higher diamondoids.

5. The functionalized higher diamondoid composition of claim 3 wherein two of $R^1$, $R^2$, $R^3$, $R^4$, $R^5$ and $R^6$ that are not hydrogen are different in the higher diamondoids.

6. The functionalized higher diamondoid composition of claim 1 comprising a higher diamondoid halide wherein at least one R is halo and the remaining R's are hydrogens.

7. The higher diamondoid composition of claim 6 wherein the halo is bromo in the higher diamondoid halide.

8. The higher diamondoid halide composition of claim 6 wherein the halo is chloro in the higher diamondoid halide.

9. The higher diamondoid halide composition of claim 6 wherein the halo is iodo in the higher diamondoid halide.

10. The functionalized higher diamondoid composition of claim 1 comprising a higher diamondoid hydroxide wherein at least one R is OH and the remaining R's are hydrogens.

11. The higher diamondoid composition of claim 10 wherein one R is OH in the higher diamondoid hydroxide.

12. The functionalized higher diamondoid composition of claim 1 comprising a higher diamondoid oxide wherein two R's form an oxide.

13. A functionalized higher diamondoid having at least one functional group and having the following Formula I:

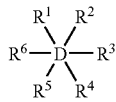

I wherein

D is a higher diamondoid nucleus with the higher diamondoid being selected from the group consisting of substituted and unsubstituted tetramantanes; substituted and unsubstituted pentamantanes; substituted and unsubstituted hexamantanes; substituted and unsubstituted heptamantanes; substituted and unsubstituted octamantanes; substituted and unsubstituted nonamantanes; substituted and unsubstituted decamantanes; substituted and unsubstituted undecamantanes; and mixtures, isomers and stereoisomers thereof; and $R^1$, $R^2$, $R^3$, $R^4$, $R^5$ and $R^6$ are independently selected from the group consisting of hydrogen; nitrate; haloalkyl; haloalkenyl; haloalkynyl; hydroxyalkyl; heteroaryl; alkylthio; alkoxy; aminoalkyl; aminoalkoxy; heterocycloalkoxy; cycloalkyloxy; aryloxy; heteroaryloxy; cyano; cyanoalkyl; cyanoaryl; and cyanoalkylamino; provided that there is at least one functional group.

14. The functionalized higher diamondoid of claim 13, wherein at least one of $R^1$, $R^2$, $R^3$, $R^4$, $R^5$ and $R^6$ is independently selected from a group consisting of alkoxy; aminoalkyl, aminoalkoxy, heterocycloalkoxy, cycloalkyloxy, aryloxy, and heteroaryloxy.

15. A composition comprising at least 10% by weight of functionalized higher diamondoids having at least one functional group and having the following Formula I:

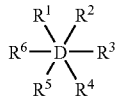

I wherein

D is a higher diamondoid nucleus with the higher diamondoid being selected from the group consisting of substituted and unsubstituted tetramantanes; substituted and unsubstituted pentamantanes; substituted and unsubstituted hexamantanes; substituted and unsubstituted heptamantanes; substituted and unsubstituted octamantanes; substituted and unsubstituted nonamantanes; substituted and unsubstituted decamantanes; substituted and unsubstituted undecamantanes; and mixtures, isomers and stereoisomers thereof; and $R^1$, $R^2$, $R^3$, $R^4$, $R^5$ and $R^6$ are independently selected from the group consisting of hydrogen; —C(O)Z wherein Z is hydrogen, alkyl, halo, haloalkyl, halothio, amino, monosubstituted amino, disubstituted amino, cycloalkyl, aryl, or heteroaryl; —$CO_2$Z wherein Z is as defined previously; —$R^7$COZ wherein $R^7$ is alkyl, aminoalkyl, or haloalkyl and Z is as defined previously; and —$R^7$COOZ wherein $R^7$ and Z are as defined previously; provided that there is at least one functional group.

16. A functionalized higher diamondoid having at least one functional group and having the following Formula I:

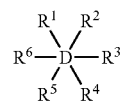

I wherein

D is a higher diamondoid nucleus with the higher diamondoid being selected from the group consisting of substituted and unsubstituted tetramantanes; substituted and unsubstituted pentamantanes; substituted and unsubstituted hexamantanes; substituted and unsubstituted heptamantanes; substituted and unsubstituted octamantanes; substituted and unsubstituted nonamantanes; substituted and unsubstituted decamantanes; substituted and unsubstituted undecamantanes; and mixtures, isomers and stereoisomers thereof; and $R^1$, $R^2$, $R^3$, $R^4$, $R^5$ and $R^6$ are independently selected from the group consisting of hydrogen; —$NH_2$; —$NHNH_2$; —NHR', —NR'R", and —$N^+$R'R"R'" wherein R', R", and R'" are independently alkyl, amino, thio, thioalkyl, heteroalkyl, aryl, or heteroaryl; —$R^8$NHCOR$^9$ wherein $R^8$ is selected from the group consisting of —$CH_2$, —$OCH_2$, —$NHCH_2$, —$CH_2CH_2$, and —$OCH_2CH_2$ and $R^9$ is selected from the group consisting of alkyl, aryl, heteroaryl, aralkyl, and heteroaraylkly; and —$R^{10}$CONHR$^{11}$ wherein $R^{10}$ is selected from the group consisting of —$CH_2$, —$OCH_2$, —$NHCH_2$, —$CH_2CH_2$, and —$OCH_2CH_2$, and $R^{11}$ is selected from the group consisting of alkyl, aryl, heteroaryl, aralkyl, and heteroaralkyl; provided that there is at least one functional group.

17. A functionalized higher diamondoid having at least one functional group and having the following Formula I:

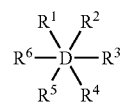

I wherein

D is a higher diamondoid nucleus with the higher diamondoid being selected from the group consisting of substituted and unsubstituted tetramantanes; substituted and unsubstituted pentamantanes; substituted and unsubstituted hexamantanes; substituted and unsubstituted heptamantanes; substituted and unsubstituted octamantanes; substituted and unsubstituted nonamantanes; substituted and unsubstituted decamantanes; substituted and unsubstituted undecamantanes; and mixtures, isomers and stereoisomers thereof; and $R^1$, $R^2$, $R^3$, $R^4$, $R^5$ and $R^6$ are independently selected from the group consisting of hydrogen;

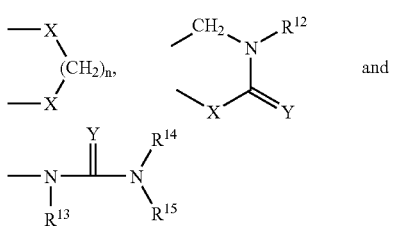

wherein:

n is 2 or 3;

X is oxygen, sulfur, carboxy, or COOZ' where Z' is hydrogen or alkyl;

Y is oxygen or sulfur; and $R^{12}$, $R^{13}$, $R^{14}$, and $R^{15}$ are independently selected from the group consisting of hydrogen, alkyl, heteroalkyl, aryl, and heteroaryl; provided that there is at least one functional group.

18. A composition comprising at least 10% by weight of functionalized higher diamondoids having at least one functional group and having the following Formula I:

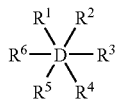

I wherein

D is a higher diamondoid nucleus with the higher diamondoid being selected from the group consisting of substituted and unsubstituted tetramantanes; substituted and unsubstituted pentamantanes; substituted and unsubstituted hexamantanes; substituted and unsubstituted heptamantanes; substituted and unsubstituted octamantanes; substituted and unsubstituted nonamantanes; substituted and unsubstituted decamantanes; substituted and unsubstituted undecamantanes; and mixtures, isomers and stereoisomers thereof; and $R^1$, $R^2$, $R^3$, $R^4$, $R^5$ and $R^6$ are independently selected from the group consisting of hydrogen and =N—Z", wherein Z" is hydrogen, —NH$_2$, —OH, alkyl,

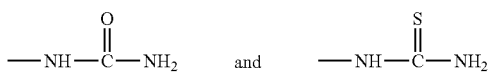

provided that there is at least one functional group.

19. The functionalized higher diamondoid of claim 13, wherein at least one of $R^1$, $R^2$, $R^3$, $R^4$, $R^5$ and $R^6$ is independently selected from the group consisting of cyano, cyanoalkyl, cyanoaryl, and cyanoalkylamino.

20. A composition comprising at least 10% by weight of functionalized higher diamondoids having at least one functional group and having the following Formula I:

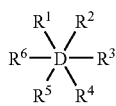

I wherein

D is a higher diamondoid nucleus with the higher diamondoid being selected from the group consisting of substituted and unsubstituted tetramantanes; substituted and unsubstituted pentamantanes; substituted and unsubstituted hexamantanes; substituted and unsubstituted heptamantanes; substituted and unsubstituted octamantanes; substituted and unsubstituted nonamantanes; substituted and unsubstituted decamantanes; substituted and unsubstituted undecamantanes; and mixtures, isomers and stereoisomers thereof; and $R^1$, $R^2$, $R^3$, $R^4$, $R^5$ and $R^6$ are independently selected from the group consisting of hydrogen; —NHR'; —NR'R"; —N$^+$R'R"R'"; —NHQ", aryl; heteroaryl; alkyl; alkenyl; and alkynyl, wherein R', R", and R'" are independently selected from the group consisting of hydrogen; aryl; heteroaryl; alkyl; alkenyl; and alkynyl; or R' and R" together with the nitrogen atom form a heterocyclic group with up to 7 ring members; and Q" is thio, thioalkyl, amino, monosubstituted amino, disubstituted amino, or trisubstituted provided that there is at least one functional group.

21. A functionalized higher diamondoid having at least one functional group and having the following Formula I:

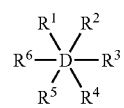

I wherein

D is a higher diamondoid nucleus with the higher diamondoid being selected from the group consisting of substituted and unsubstituted tetramantanes; substituted and unsubstituted pentamantanes; substituted and unsubstituted hexamantanes; substituted and unsubstituted heptamantanes; substituted and unsubstituted octamantanes; substituted and unsubstituted nonamantanes; substituted and unsubstituted decamantanes; substituted and unsubstituted undecamantanes; and mixtures, isomers and stereoisomers thereof; and $R^1$, $R^2$, $R^3$, $R^4$, $R^5$ and $R^6$ are independently selected from the group consisting of hydrogen;

—COOR$^{16}$ wherein R$^{16}$ is alkyl, aryl, or aralkyl;

—COR$^{17}$ wherein R$^{17}$ is alkyl, aryl, heteroalkyl;

—NHNH$_2$;

—R$^{18}$NHCOR$^{19}$ wherein R$^{18}$ is a bond or is selected from the group consisting of alkylene, arylene, alkarylene, and aryalkylene and R$^{19}$ is selected from the group consisting of hydrogen, alkyl, —N$_2$, aryl, amino, and —NHR$^{20}$ wherein R$^{20}$ is selected from the group consisting of hydrogen, —SO$_2$-aryl, —SO$_2$-alkyl, —SO$_2$-aralkyl, —CONHR$^{21}$ wherein R$^{21}$ is selected from the group consisting of hydrogen, alkyl, and aralkyl, and —CSNHR$^{21}$ wherein R$^{21}$ is as defined above; and —COOR$^{22}$, wherein R$^{22}$ is alkyl or aryl; and —NR$^{23}$—(CH$_2$)$_n$—NR$^{24}$R$^{25}$ wherein R$^{23}$, R$^{24}$, and R$^{25}$ are independently selected from the group consisting of hydrogen, alkyl, and aryl, and n is from 1 to 20;

provided that there is at least one functional group.

22. A functionalized higher diamondoid having at least one functional group and having the following Formula I:

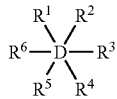

wherein

D is a higher diamondoid nucleus with the higher diamondoid being selected from the group consisting of substituted and unsubstituted tetramantanes; substituted and unsubstituted pentamantanes; substituted and unsubstituted hexamantanes; substituted and unsubstituted heptamantanes; substituted and unsubstituted octamantanes; substituted and unsubstituted nonamantanes; substituted and unsubstituted decamantanes; substituted and unsubstituted undecamantanes; and mixtures, isomers and stereoisomers thereof; and $R^1$, $R^2$, $R^3$, $R^4$, $R^5$ and $R^6$ are independently selected from the group consisting of hydrogen; —N=C=N—; —N=C=S; —N=C=O; —R—N=C=O, —R—N=C=S; —N=S=O; —R—N=S=O wherein R is alkyl; —$PH_2$; —$PDX_2$ wherein X is halo; —$PO(OH)_2$; —$SO_2H$; —SOX wherein X is halo; —$SO_2R$ wherein R is alkyl; —$SO_2OR$; —$OSO_3H$ wherein R is alkyl; —$SONR^{26}R^{27}$ wherein $R^{26}$ and $R^{27}$ are independently hydrogen or alkyl; and —$N_3$; —OC(O)Cl; and —OC(S)Cl;

provided that there is at least one functional group.

23. The functionalized higher diamondoid of claim 13 which is a higher diamondoid nitrate.

24. The composition of claim 1, comprising at least 50% by weight of the functionalized higher diamondoids.

25. The composition of claim 15, comprising at least 50% by weight of the functionalized higher diamondoids.

26. The composition of claim 18, comprising at least 50% by weight of the functionalized higher diamondoids.

27. The composition of claim 20, comprising at least 50% by weight of the functionalized higher diamondoids.

28. A composition comprising at least 10% by weight of functionalized higher diamondoids defined in claim 13.

29. A composition comprising at least 10% by weight of functionalized higher diamondoids defined in claim 16.

30. A composition comprising at least 10% by weight of functionalized higher diamondoids defined in claim 17.

31. A composition comprising at least 10% by weight of functionalized higher diamondoids defined in claim 21.

32. A composition comprising at least 10% by weight of functionalized higher diamondoids defined in claim 22.

* * * * *